US011655461B2

(12) United States Patent
Hume et al.

(10) Patent No.: US 11,655,461 B2
(45) Date of Patent: May 23, 2023

(54) ANTIGEN PURIFICATION

(71) Applicant: KBIO HOLDINGS LIMITED, London (GB)

(72) Inventors: Steven D. Hume, Owensboro, KY (US); Leigh Burden, Owensboro, KY (US); Joshua Morton, Evansville, IN (US); Greg Pogue, Austin, TX (US); Barry Bratcher, Owensboro, KY (US); Hugh A. Haydon, Louisville, KY (US); Carrie A. Simpson, Evansville, IN (US); Nick Partain, Owensboro, KY (US); John W. Shepherd, Owensboro, KY (US); Kelsi Swope, Maceo, KY (US)

(73) Assignee: KBIO HOLDINGS LIMITED, London (GB)

( * ) Notice: Subject to any disclaimer, the term of this patent is extended or adjusted under 35 U.S.C. 154(b) by 24 days.

(21) Appl. No.: 17/063,022

(22) Filed: Oct. 5, 2020

(65) Prior Publication Data
US 2021/0017502 A1    Jan. 21, 2021

Related U.S. Application Data

(63) Continuation of application No. 16/437,770, filed on Jun. 11, 2019, now Pat. No. 10,822,591.

(60) Provisional application No. 62/683,865, filed on Jun. 12, 2018.

(51) Int. Cl.
| | | |
|---|---|---|
| *A61K 39/00* | (2006.01) | |
| *B01D 15/34* | (2006.01) | |
| *B01D 15/36* | (2006.01) | |
| *B01D 15/38* | (2006.01) | |
| *C07K 1/16* | (2006.01) | |
| *C07K 1/18* | (2006.01) | |
| *C07K 1/22* | (2006.01) | |
| *C12N 7/00* | (2006.01) | |
| *A61K 39/145* | (2006.01) | |
| *A61K 47/69* | (2017.01) | |
| *A61K 38/36* | (2006.01) | |

(52) U.S. Cl.
CPC ............... *C12N 7/00* (2013.01); *A61K 38/36* (2013.01); *A61K 39/0001* (2013.01); *A61K 39/145* (2013.01); *A61K 47/6901* (2017.08); *B01D 15/34* (2013.01); *B01D 15/361* (2013.01); *B01D 15/3809* (2013.01); *B01D 15/3847* (2013.01); *C07K 1/16* (2013.01); *C07K 1/18* (2013.01); *C07K 1/22* (2013.01); *A61K 2039/5254* (2013.01); *C12N 2770/00051* (2013.01); *C12N 2770/00061* (2013.01); *C12N 2770/40051* (2013.01); *C12N 2770/40061* (2013.01)

(58) Field of Classification Search
None
See application file for complete search history.

(56) References Cited

U.S. PATENT DOCUMENTS

| | | | |
|---|---|---|---|
| 6,037,456 | A | 3/2000 | Garger et al. |
| 6,261,823 | B1 | 7/2001 | Tang et al. |
| 7,901,921 | B2 | 3/2011 | Coffey |
| 7,939,318 | B2 | 5/2011 | McCormick et al. |
| 8,124,106 | B2 | 2/2012 | Weggeman et al. |
| 8,771,703 | B2 | 7/2014 | Couture et al. |
| 9,169,491 | B2 | 10/2015 | Truan et al. |
| 10,052,370 | B2 | 8/2018 | Savelyeva et al. |
| 2006/0188991 | A1 | 8/2006 | McCormick et al. |
| 2006/0288449 | A1 | 12/2006 | Garger et al. |
| 2007/0172846 | A1 | 7/2007 | Zhang et al. |
| 2009/0053261 | A1 | 2/2009 | Lindbo et al. |
| 2009/0117144 | A1 | 5/2009 | Rasochova et al. |
| 2010/0068175 | A1 | 3/2010 | Gillies et al. |
| 2010/0297174 | A1 | 11/2010 | Garcia-Sastre et al. |
| 2011/0086058 | A1 | 4/2011 | Jiang et al. |
| 2011/0104753 | A1 | 5/2011 | Couture et al. |
| 2013/0280298 | A1 | 10/2013 | Leclerc |
| 2016/0296617 | A1 | 10/2016 | Jiang et al. |
| 2017/0002332 | A1 | 1/2017 | Genethon et al. |
| 2017/0258886 | A1 | 9/2017 | Ivanov et al. |
| 2018/0119110 | A1 | 5/2018 | Schlegl et al. |
| 2020/0368341 | A1 | 11/2020 | Dutta et al. |

FOREIGN PATENT DOCUMENTS

| | | |
|---|---|---|
| CN | 101268192 A | 9/2008 |
| CN | 101646772 A | 2/2010 |
| CN | 102271704 A | 12/2011 |

(Continued)

OTHER PUBLICATIONS

Doonan, Essential Guides For Isolation/Purification of Enzymes and Proteins; published 2002, Academic Press. (Year: 2002).*
Datar and Rosen, Biotechnology Second Edition, 1993, Edited by H.-J. Rehm and G. Reed. (Year: 1993).*
Wang et al., Journal of Separation Science, 2008, 31: 2032-2039. (Year: 2008).*

(Continued)

*Primary Examiner* — Nicole Kinsey White
(74) *Attorney, Agent, or Firm* — Wyatt, Tarrant & Combs, LLP; Max E. Bridges; Stephen C. Hall

(57) ABSTRACT

Disclosed herein are methods and exemplary compositions associated with antigen purification, exemplary aspects of which may include harvesting viral and antigenic substances from source organisms; and a purification platform comprising chemical separation and size-difference separation for the removal of contaminants, debris and impurities from the viral and protein (e.g. antigenic, including influenza hemagglutinin antigens) substances, as well as their concentration and collection.

11 Claims, 39 Drawing Sheets

(56) References Cited

FOREIGN PATENT DOCUMENTS

| CN | 102397559 | A  | 4/2012  |
|----|-----------|----|---------|
| CN | 104845945 | A  | 8/2015  |
| EP | 1561758   | B1 | 10/2005 |
| WO | 03103605  | A2 | 12/2003 |
| WO | 03103605  | A3 | 12/2003 |
| WO | 2005091753| A2 | 10/2005 |
| WO | 2005091753| A3 | 10/2005 |
| WO | 2007038145| A2 | 4/2007  |
| WO | 2008073490| A1 | 6/2008  |
| WO | 2012128628| A1 | 9/2012  |
| WO | 2013010797| A1 | 1/2013  |
| WO | 2015105551| A1 | 7/2015  |
| WO | 2016156613| A1 | 10/2016 |
| WO | 2017011826| A1 | 1/2017  |

OTHER PUBLICATIONS

United States Patent and Trademark Office; Notification of Transmittal of the International Search Report and the Written Opinion of the International Searching Authority, or the Declaration for PCT/US20/63902; dated May 7, 2021; pp. 1-15; United States Patent and Trademark Office Searching Authority; US.

Lindbo, John A., TRBO: A High-Efficiency Tobacco Mosaic Virus RNA-Based Overexpression Vector, Journal, Dec. 2007, pp. 1232-1240, vol. 145, Plant Physiology http://www.plantphysiol.org/content/plantphysiol/145/4/1232.full.pdf, www.plantphysiol.org, 2007 American Society of Plant Biologists.

Akerblom, Anna and Peter Bergvall (2012). Constraints on Vaccine Production. BioProcess International, Industry Yearbook 2012-2013.

Altintoprak et al. "Bioengineered viral nanorings for the insertion into bio-hybrid systems," University of Stuttgart, Thesis, Apr. 12, 2016 (Apr. 12, 2016), pp. 113-140 of 199. Retrieved from the Internet:<https:f/d-nb.info/1161409939/34> t>n Aug. 12, 2019 (Aug. 12, 2019). entire document.

Arnaboldi, P. M., D'Arco, C., Peters, L. A., Seegers, J. F., Mayer, L., McCormick, A. A., Dattwyler, R. J. (2016) Intranasal delivery of a protein subunit vaccine using a Tobacco Mosaic Virus platform protects against pneumonic plague. Vaccine. 34(47):5768:5776. PMID: 27745954.

Banik, S., Mansour, A. A., Suresh, R. V., Wykoff-Clary, S., Malik, M., McCormick, A. A., Bakshi, C. S. (2015) Development of a Multivalent Subunit Vaccine against Tularemia Using Tobacco Mosaic Virus (TMV) Based Delivery System. PLoS One. 10(6):1-22. PMID: 26098553.

Bergmann, Katherin (Nov. 20, 2014), UV-C Irradiation: A New Viral Inactivation Method for Biopharmaceuticals. American Pharmaceutical Review. https:f/www.americanpharmaceuticalreview.com/Featured-Articles/169257-UV-Crradiation-A-New-Viral-Inactivation-Method-for-Biopharmaceuticals/.

Blom H, Akerblom A, Kon T, Shaker S, van der Pol L, Lundgren M. 2014. Efficient chromatographic reduction of ovalbumin for egg-based influenza virus purification. Vaccine 32:3721-3724.

Boon A, Finkelstein D, Zheng M, Liao G. H5N1 influenza virus pathogenesis in genetically diverse mice is mediated at the level of viral load. MBio [Internet]. 2011 ;2(5):1-10. Available from: http://mbio.asm.org/content/2/5/e00171-11. Short.

Bruckman, et al. Tobacco mosaic virus rods and spheres as supramolecular high-relaxivity MRI contrast agents. NIH Public Access Author Manuscript. National Institutes of Health, pp. 1-17. Also published as J Mater Chem B. 2013;1(10):1482-1490. doi:10.1039/C3TB00461A. https://pubmed.ncbi.nlm.nih.gov/23589767.

Zhao D. et al. . Enterovirus71 virus-like particles produced from insect cells and purified by multistep chromatography elicit strong humoral immune responses in mice. J. Appl. Microbiol. 119, 1196-1205 (2015).

Chahal P. S. et al. . Validation of a high-performance liquid chromatographic assay for the quantification of Reovirus particles type 3. J. Pharm. Biomed. Anal. 45, 417-421 (2007).

Chen Q, Lai H. Plant-derived virus-like particles as vaccines. Hum Vaccin Immunother. 2013;9(1):26-49. doi:10.4161/hv.22218 https://www.ncbi.nlm.nih.gov/pmc/articles/PMC3667944/.

Chu, et al.; Enhanced Stability of Inactivated Influenza Vaccine Encapsulated in Dissolving Microneedle Patches; Author Manuscript; HHS Public Access; Pharm Res.; Apr. 2016; pp. 868-878; 33(4); available in PMC Apr. 1, 2017; doi: 10.1007/s11095-015-1833-9.

Coenen, et al.; Stability of influenza sub-unit vaccine; Journal; Vaccine; 2006; pp. 525-531; 24; www.elsevier.com/locate/vaccine; www.sciencedirect.com; copyright 2005 Elsevier Ltd; available online Aug. 15, 2005.

Dai, et al.; Advances and challenges in enveloped virus-like particle (VLP)-based vaccines; Journal/Minireview; Journal of Immunological Sciences; 2018; pp. 36-41; 2(2); China.

De Boer et al. "Acid-Activated Structural Reorganization of the Rift Valley Fever Virus Gc Fusion Protein," Journal of Virology, Oct. 3, 2012 (Oct. 3, 2012), vol. 86, No. 24, pp. 13642-13652. entire document.

Dorokhov YL, Sheveleva M, Frolova OY, Komarova T V., Zvereva AS, Ivanov PA, et al. Superexpression of tuberculosis antigens in plant leaves. Tuberculosis. 2007;87(3):218-24.

Fernandes P, Peixoto C, Santiago VM, Kremer EJ, Coroadinha AS, Alves PM. 2012. Bioprocess development for canine adenovirus type 2 vectors. Gene Ther 20:353-360.

Gasanova, Genetically Modified TMV Particles May Serve as Carrier for Chemical Conjugation of Influenza Antigens to Produce Multivalent Nanovaccines; Jun. 10, 2017; https://eventscribe.com/2017/sivb/ajaxcalls/PresentationInfo.asp?efp=SkpOQ0JVWEczODE5&PresentationID=285003&md=0.1628216.

GE Healthcare Life Sciences, Purification of influenza A/H1 N1 using CAPTO Core 700; Mar. 2012; Application note 29-0003-34 AA: pp. 1-6: www.gelifesciences.com/captocore: Sweden.

James et al., Novel High-throughput Approach for Purification of Infectious Virions; Sci Rep. 2016; 6:36826 DOI:100.1038/srep36826. https://www.ncbi.nlm.nih.gov/pmc/articles/PMC5101806/.

Kemnade, J.O., Seethammagari, M., Collinson-Pautz, M., Kaur, H., Spencer, D. M., McCormick, A. A. (2014) Tobacco mosaic virus efficiently targets DC uptake, activation and antigen-specific T cell responses in vivo. Vaccine 32 (33)4228-4233. PMID: 24923637.

Klimyuk V, Pogue G, Herz S, Butler J, Haydon H. Production of recombinant antigens and antibodies in Nicotiana benthamiana using 'magnifection' technology: GMP-compliant facilities for small- and large-scale manufacturing. Curr Top Microbiol Immunol. 2014;375:127-154. doi:10.1007/82_2012_212 https://pubmed.ncbi.nlm.nih.gov/22527176/.

Kumru, et al.; Vaccine instability in the cold chain: Mechanisms, analysis and formulation strategies; Journal; Biologicals; 2014; pp. 237-259; 42; www.elsevier.com/locate/biologicals.

Kwon, et al.; Oral delivery of bioencapsulated exendin-4 expressed in chloroplasts lowers blood glucose level in mice and stimulates insulin secretion in beta-TC6 cells; Journal; Plant Biotechnology Journal; 2013; pp. 77-86; 11; doi: 10.1111/pbi.12008.

Mallajosyula et al. "Single-Dose Monomeric HA Subunit Vaccine Generates Full Protection From Influenza Challenge," Human Vaccines & Immunotherapeutics, Dec. 30, 2013 (Dec. 30, 2013), vol. 10, Iss. 3, pp. 586-595. entire document.

Mallajosyula, I. K., Hiatt, E., Hume, S. Johnson, A., Jeevan, T., Chikwamba, R, Webby, R J., Pogue, G. P., Bratcher, B., Haydon, H., McCormick, A. A. (2014) Single dose monomeric HA subunit vaccine generates full protection from influenza challenge. Hum. Vaccin. Immunother. 10:58695. PMID: 24378714.

Mallajosyula, J. K., Jeevan, T., Chikwamba, R., Webby, R. J., McCormick, A. A. (2016) A Single Dose TMV-HA Vaccine Protects Mice from H5N1 Influenza Challenge. Int. J. Vaccine. Res. 1(2):6. DOI:10.15226/2473-2176/1/2/00106.

Mansour AA, Banik S, Suresh R V., Kaur H, Malik M, McCormick AA, et al. An improved tobacco mosaic virus (TMV)-conjugated multiantigen subunit vaccine against respiratory tularemia. Front Microbiol. 2018;9(JUN).

Manuel-Cabrera, et al.; Immune response to a potyvirus with exposed amino groups available for chemical conjugation; Virology Journal; 2012; pp. 9:75; http://www.virologyj.com.content/9/1/75.

(56) References Cited

OTHER PUBLICATIONS

McCormick AA, Corbo TA, Wykoff-Clary S, Nguyen L V., Smith ML, Palmer KE, et al. TMV-peptide fusion vaccines induce cell-mediated immune responses and tumor protection in two murine models. Vaccine. 2006;24(40-41):6414-23.

McCormick AA, Corbo TA, Wykoff-Clary S, Palmer KE, Pogue GP. Chemical conjugate TMV—Peptide bivalent fusion vaccines improve cellular immunity and tumor protection. Bioconjug Chem. 2006;17(5):1330-8.

McCormick AA, Shakeel A, Yi C, Kaur H, Mansour AM, Bakshi CS. Intranasal administration of a two-dose adjuvanted multi-antigen TMV-subunit conjugate vaccine fully protects mice against Francisella tularensis LVS challenge. PLoS One. 2018;13(4).

Nestola, Piergiuseppe (2015). Improving Downstream Processing for Viral Vectors and Viral Vaccines. Dissertation Presented to Obtain the Ph.D degree in Chemical Engineering from the University of Lisbon.

Nikitin NA, Zenin VA, Trifonova EA, Ryabchevskaya EM, Kondakova OA, Fedorov AN, et al. Assessment of structurally modified plant virus as a novel adjuvant in toxicity studies. Regul Toxicol Pharmacol. 2018;97:127-33.

Nuzzaci, et al.; In vitro stability of Cucumber mosaic virus nanoparticles carrying a Hepatitis C virus-derived epitope under simulated gastrointestinal conditions and in vivo efficacy of an edible vaccine; Journal; Journal of Virological Methods; 2010; pp. 211-221; 165; www.elsevier.com/locate/jviromet.

Palmer KE, Benko A, Doucette SA, Cameron TI, Foster T, Hanley KM, et al. Protection of rabbits against cutaneous papillomavirus infection using recombinant tobacco mosaic virus containing L2 capsid epitopes. Vaccine. 2006;24(26):5516-25.

Pogue, G. P., Lindbo, J. A., Garger, S. J., Fitzmaurice, W. P. 2002. Making an ally from an enemy: plant virology and the new agriculture. Ann. Rev. Phytopathol. 40:45 74.

Rohovie, et al.; Virus-like particles: Next-generation nanoparticles for targeted therapeutic delivery; Journal Review; AICHE Bioengineering & Translational Medicine; 2017; pp. 43-57; 2; wileyonlinelibrary.com/journal/btm2; DOI 10.1002/btm2.10049.

Rybicki, E.; Plant-based vaccines against viruses; Virology Journal; 2014; pp. 1-20; 11:205; http://www.virologyj.com/content/11/1/205.

Segura M. M., Kamen A. A. & Garnier A. Overview of current scalable methods for purification of viral vectors. Methods Mol. Biol. 737, 89-116 (2011).

Smith ML, Lindbo JA, Dillard-Telm S, Brosio PM, lasnik AB, McCormick M, et al. Modified Tobacco mosaic virus particles as scaffolds for display of protein antigens for vaccine applications. Virology. 2006;348(2):475-88.

Smith, M. L., Corbo, T., Bernales, J., Lindbo, J. A., Pogue, G. P., Palmer, K. E., McCormick, A. A. 2007. Assembly of trans encapsidated recombinant viral vectors engineered from Tobacco mosaic virus and Semliki Forest virus and thei1 Valuation as immunogens. Virology 358:321-33.

Soema, et al.; Current and next generation influenza vaccines: Formulation and production strategies; Journal; European Journal of Pharmaceutics and Biopharmaceutics; 2015; pp. 251-263; 94; www.elsevier.com/locate/ejpb.

Stegmann et al. "Effects of Low pH on Influenza Virus," The Journal of Biological Chemistry, Dec. 25, 1987 (Dec. 25, 1987), vol. 262, No. 36, pp. 17744-17749. entire document.

Transfiguracion J., Bernier A., Arcand N., Chahal P. & Kamen A. Validation of a high-performance liquid chromatographic assay for the quantification of adenovirus type 5 particles. J. Chromatogr. B Biomed. Sci. Appl. 761, 187-194 (2001).

Tseng et al., A fast and efficient purification platform for cell-based influenza viruses by flow-through chromatography; Mar. 22, 2017.; Vaccine 26 (2018) 3146-3152; http://dx.doi.org/10.1016/j.vaccine.2017.03.016; pii: S0264-410X(17) 30322-5.

United States Patent and Trademark Office; The International Search Report and the Written Opinion of the International Searching Authority; dated Sep. 3, 2019; PCT/US2019/036559; pp. 1-10; United States Patent and Trademark Office; US.

World Health Organization (2014), Guidelines on viral inactivation and removal procedures intended to assure the viral safety of human blood plasma products. WHO Technical Report, Series No. 924. https://www.who.int/bloodproducts/publications/WHO_TRS_924_A4.pdf.

Wu M, Shi J, Fan D, Zhou Q, Wang F, Niu Z, et al. Biobehavior in normal and tumor-bearing mice of tobacco mosaic virus. Biomacromolecules. 2013;14(11):4032-7.

Xiong, et al. (Posh A. (eds) 2D Page: Sample Preparation and Fractionation. Methods in Molecular Biology, vol. 424. Humana Press (2008)).

Pillet, S., et al. (2015). Plant-derived H7 VLP vaccine elicits protective immune response against H7N9 influenza virus in mice and ferrets. Vaccine, 33(46), 6282-6289. https://doi.org/10.1016/j.vaccine.2015.09.065.

Pillet, Stéphane, et al. (2019). Immunogenicity and safety of a quadrivalent plant-derived virus like particle influenza vaccine candidate—Two randomized Phase II clinical trials in 18 to 49 and 50 years old adults. PLoS ONE, 14(6). https://doi.org/10.1371/journal.pone.0216533.

Wen, Jianxin, Veterinary Immunology Laboratory Guide, China Agricultural University Press, Dec. 2016, pp. 29-30.

The United States Patent and Trademark Office; The International Search Report and the Written Opinion of the International Searching Authority; dated Jun. 11, 2021; PCT/US2021/021087; pp. 1-15; United States Patent and Trademark Office; US.

Lu, et al. (2014) Production and stabilization of the trimeric influenza hemagglutinin stem domain for potentially broadly protective influenza vaccines, PNAS, Jan. 7, 2014, vol. 111, No. 1, pp. 125-130; www.pnas.org/cgi/doi/10.1073/pnas.1308701110.

Yang et al. "Harnessing an RNA-Mediated Chaperone for the Assembly of Influenza Hemagglutinin in an Immunologically Relevant Conformation," The FASEB Journal, Apr. 26, 2018 (Apr. 26, 2018), vol. 32, No. 5, pp. 2658-2675. entire document.

Yin et al. Tobacco Mosaic Virus as a New Carrier for Tumor Associated Carbohydrate Antigens. NIH Public Access Author Manuscript. National Institutes of Health, pp. 1-20. Also Published in Bioconjug Chem. Aug. 15, 2012; 23(8): 1694-1703. doi:10.1021/bc300244a. https://www.ncbi.nlm.nih.gov/pmc/articles/PMC3426870/.

Zhang, et al, Mixed-mode chromatography in pharmaceutical and biopharmaceutical applications, Journal of Pharmaceutical and Biomedical Analysis, 2016, 128:73-88.

United States Patent and Trademark Office; Invitation to Pay Additional Fees and, Where Applicable, Protest Fee; from The International Searching Authority; Feb. 17, 2021; PCT/US20/63902; pp. 1-24; United States Patent and Trademark Office; US.

Author Not Found—Research on Immunization and Prevention of Major Livestock and Poultry Diseases, pp. 167-168, China Agricultural Science and Technology Press, Dec. 1996 (English Translation).

* cited by examiner

ANTIGEN PURIFICATION

CROSS-REFERENCE TO RELATED APPLICATIONS

This continuation patent application claims the benefit of and priority to T U.S. Pat. No. 10,822,591, which issued on Nov. 3, 2020, which claims the benefit of and priority to U.S. Provisional Patent Application Ser. No. 62/683,865, filed on Jun. 12, 2018, the teachings and entire disclosure of both are fully incorporated herein by reference.

FIELD OF INVENTION

The embodiments described herein include use of a multi-set process for producing highly purified, recombinant antigens and recombinant viruses as antigen carriers, and still further various embodiments relate to vaccine production using a purified virus and a purified antigen.

BACKGROUND

Viruses have a nucleic acid molecule in a protein coat and replicate only inside the living cells of other organisms. Often thought of as harmful, a wide range of viruses are capable of infecting all types of life forms such as humans, livestock, and plants. Yet on the positive side, there is growing interest to use viruses for a range of therapeutic purposes, including without limitation vaccine creation, gene therapy, and cancer treatments, to name a few. However, to study viruses, understand their structure, and adapt viruses for molecular tools and for disease therapy vectors and carriers, viruses first must be purified to remove any cell debris, macro-molecular fibers, organelles, lipids, and other impurities that would interfere with the intended function of the virus.

Once purified, viruses are suitable for a number of uses. One that is relevant to the current disclosure is the traditional notion of using the virus (considered a pathogen in this context) for study and development of genetic strategies against viruses. But discussed at further length in the present disclosure is the use of purified viruses as antigen carriers to prepare a vaccine. Antigens are molecules that, when appropriately delivered to an organism, are capable of producing an immune response in that organism, by stimulating the production of antibodies through binding with an antibody within the organism that matches the molecular structure of the antigen. Recombinant antigens are produced from recombinant DNA, which through known techniques is cloned into vectors which are then introduced into specific host cells, such as bacteria, mammalian cells, yeast cells, and plant cells, to name some. The recombinant antigen is then expressed using the host cell's translational apparatus. After expression, the recombinant antigen can be harvested and attached to a virus via covalent bonds, through a process known as conjugation. Following conjugation of the antigen to the virus, the virus can serve as a carrier to deliver the antigen to an organism and activate the immune system response. In this way, a virus-antigen conjugate can provide a therapeutic use. Proper virus-antigen conjugation is needed for the antigen to activate an immune response that produces antibodies in the host cells of a source organism. Purification of both the virus and antigen fosters this proper conjugation.

Current methods to purify viruses generally are limited for use in small biochemical quantities, e.g., on the order of nanograms to milligrams, and have not been proven in industrial quantities, which are on the order of grams to kilograms. For example, a previously-used method known as "Crude Infected Cell Lysate" utilizes crude cell lysates or cell culture media from virus-infected cells. Infected mammalian cells are lysed by freeze-thaw or through other known methods, the debris is removed by low-speed centrifugation, and supernatants are then used for experimentation. The intact infected organisms are ruptured or ground physically, and the resulting extract is clarified using centrifugation or filtration to produce crude virus preparations. However, this method suffers from high contamination with many non-virus factors that impact the ability to conduct experimentation and manipulate the virus.

A second example of prior purification steps is high-speed ultracentrifugation, by which viruses are pelleted, or further purified through pelleting, via a low-density sucrose solution, or suspended in between sucrose solutions of various densities. Limitations of this method include production of purified viruses in only small quantities due to the limited size and scalability of high velocity separations, and poor virus purity due to additional host proteins often co-purifying with virus samples.

A third method previously used to enhance virus purity is density gradient ultracentrifugation. In this method, gradients of cesium chloride, sucrose, iodixanol or other solutions are used for separation of assembled virus particles or for removal of particles lacking genetic content. Limitations of this method include the time required to purify the virus (often 2-3 days), the limited number of samples, the amount of samples that can be analyzed at a time (generally 6 per rotor), and the small quantity of virus that can be purified (generally micrograms to milligrams of final product).

Organic extraction and poly-ethylene glycol precipitation also have been used to purify viruses, including viruses from plants, such as by removing lipids and chloroplasts. Again, however, these known methods suffer from poor purity, with products typically still attached to host proteins, nucleic acids, lipids, and sugars which result in significant aggregation of resulting virus products. These limitations reduce the utility of the final product for compliance with the Current Good Manufacturing Practice (cGMP) regulations enforced by the US Food and Drug Administration (FDA).

Current cGMP regulations promulgated by FDA contain minimum requirements for the methods, facilities, and controls used in manufacturing, processing, and packing of a drug product. These regulations are aimed at safety of a product and ensuring that it has the ingredients and strength it claims to have. Accordingly, for viruses to be utilized in vaccine creation, gene therapy, cancer treatments, and other clinical settings, the final viral product must comply with the cGMP regulations. If a final viral product does not comply with the cGMP regulations, like the product from the polyethylene glycol precipitation method, its utility for use in the clinical setting either does not exist or is greatly diminished.

Scalability refers to a process that consistently and reproducibly produces the same product even as the quantity of product increases, e.g, going from laboratory scale (<0.1 square meters) to at least systems >20 square meters. The methods previously used as identified above all suffer from a lack of consistency, low scalability (i.e., creates product only in biochemical quantities), and a lack of compliance with the cGMP regulations.

In terms of large scale production, plant-based production has garnered attention, although prominent limitations exist with their use. Plant-based production systems are capable of producing industrial scale yields at much less cost than animal cell production systems such as Chinese Hamster Ovary (CHO). However, certain conventional purification methods, which have been appropriate at some scale for non-plant viruses, will not work for plant-made viruses and antigens. These limitations arise because of myriad differences in purifying plant viruses, as opposed to the purification of viruses from animal cell cultures. While animal cells produce primary protein and nucleic acid impurities, plants are also sources of significant and additional impurities not found in animal cells. Some of these include lipid composition of chloroplast membranes and vacuolar membranes, simple and complex carbohydrate impurities, and nanoparticulate organellar impurities. Indeed, crude plant extracts will often foul the equipment used in processing and purifying the viral and antigen matter obtained from plants, for example due to accumulation of impurities on the separation membranes of the equipment or media beds leading. Such fouling inevitably leads to pressure flow failure, poor filtration and ultimately poor yield of product. Another problem is these impurities have a tendency to aggregate and become capable of co-purifying within any protein, virus, or other "product" desired from a plant. Accordingly, current methods for purifying viruses will not adequately remove all or even a sufficient amount of impurities, including but not limited to impurities found in plant extracts and have not been shown to adequately produce purified viruses.

Accordingly, there is a significant need for virus and antigen purification platforms consistently capable of producing highly purified viruses on the commercial scale, i.e. grams to kilograms and higher, and in a manner that complies with the cGMP regulations. Such improvements would allow for the clinical development for using tools in vaccine creation, gene therapy, and for cancer treatments. Along with other features and advantages outlined herein, the platforms described herein according to multiple embodiments and alternatives meet this and other needs.

SUMMARY OF EMBODIMENTS

In some embodiments according to the present disclosure, a virus purification method is directed to a multi-set process that comprises harvesting from a source organism virus material containing at least one virus; removing cellular debris from the at least one virus thereby clarifying the structure of the at least one virus; concentrating the separated and clarified virus which in some embodiments is performed with a filtration device comprising a membrane with pores of a size not to exceed a predetermined limit as selected by a user; and processing the concentrated virus by subjecting it to a series of separation procedures and collecting the virus after each separation procedure, wherein at least one separation procedure includes ion-exchange chromatography to separate host cell contaminants from the virus, and at least one separation procedure includes a multi-modal chromatography to separate residual impurities from the virus on the basis of at least size differences between the virus and the impurities, and chemical interaction occurring between the impurities and one or more chromatography ligands. In some embodiments, a plant is the source organism undergoing recombinant expression of a virus, with *Nicotiana benthamiana* and *Lemna minor* as non-limiting examples. When the source organism is a plant, harvesting may include seed production and plant germination with inducement of transient gene expression to from a desired protein, as discussed below. Alternatively, the source organism undergoing recombinant expression of a virus is a non-plant host such as, without limitation, bacterial, algal, yeast, insect, or mammalian organisms.

Additionally, various aspects of multiple embodiments described herein are directed to producing or purifying, or both, an antigen which can be conjugated with a virus. In some embodiments, a plant is the source organism undergoing recombinant expression of antigen; alternatively, the source organism undergoing recombinant expression of antigen is a non-plant host such as, without limitation, bacterial, algal, yeast, insect, or mammalian organisms.

Advantageously, a multi-set process practiced according to various embodiments described herein produces highly purified viruses or recombinant antigens, or both, on a commercial scale. Various steps are employed to improve the upstream purification processes, such as enriching plant viruses. Some embodiments utilize size exclusion chromatography, as well as other features, to produce purified recombinant viruses and recombinant antigens. Accordingly, various embodiments described herein provide one or more viruses and one or more antigens suitable for the preparation of one or more vaccines of conjugated virus and antigen.

With regard to viruses, through the practice of some embodiments of an inventive virus purification platform described herein, purification of rod-shaped plant viruses (such as tobacco mosaic virus, i.e., "TMV") and icosahedral plant viruses (such as red clover mosaic virus) has been achieved. According to multiple embodiments herein, purification of TMV and red clover mosaic virus was achieved, representing two structurally diverse viruses in terms of size and structure. For example, a smaller icosahedral virus like red clover mosaic virus has T=3 symmetry, dimensions of approximately 31-34 nm, and approximately 180 capsid proteins. Conversely, TMV is approximately 18 nanometers in diameter, 300 nm in length and contains 2160 capsid proteins. In view of this diversity, the inventive process has worked based on two structurally different viruses to allow virus passage into the permeate while retaining unwanted cellular debris. In use, operational parameters can be controlled so all types of viruses both pass into the permeate, while chlorophyll/cellular debris are retained, and the tangential flow (TFF) system continues to operate efficiently without unduly or untimely becoming fouled. Additional TFF steps are designed to retain virus while allowing smaller proteins to pass into the permeate, and dual chromatography steps are controlled to exclude viruses both large and small, while capturing host cell proteins, host cell DNA, endotoxin, and plant polyphenolics.

Based upon the successful purification of red clover mosaic virus and TMV, it is expected that the virus purification platform according to multiple embodiments and alternatives can successfully purify a wide array of viruses including: viruses comprising a range of genetic materials (e.g. double- and single-stranded DNA viruses, and RNA viruses), geometries (e.g. rod-shaped, flexious rods, and icosahedral), and families (Caulimoviridae, Geminiviridae, Bromoviridae, Closteroviridae, Comoviridae, Potyviridae, Sequiviridae, Tombusviridae).

Non-limiting viruses upon which the embodiments described herein are expected to succeed include those of the genuses *Badnavirus* (e.g. commelina yellow mottle virus); *Caulimovirus* (e.g. cauliflower mosaic virus); SbCMV-like viruses (e.g. Soybean chlorotic mottle virus); CsVMV-like viruses (e.g. Cassava vein mosaicvirus); RTBV-like viruses (e.g. rice tungro bacilliformvirus); petunia vein clearing-like viruses (e.g. petunia vein clearing virus); *Mastrevirus* (Subgroup I Geminivirus) (e.g. maize streak virus) and *Curtovirus* (Subgroup II Geminivirus) (e.g. beet curly top virus)

and *Begomovirus* (Subgroup III Geminivirus) (e.g. bean golden mosaic virus); *Alfamovirus* (e.g. alfalfa mosaic virus); *Ilarvirus* (e.g. tobacco streak virus); *Bromovirus* (e.g. brome mosaic virus); *Cucumovirus* (e.g. cucumber mosaic virus); *Closterovirus* (e.g. beet yellows virus); *Crinivirus* (e.g. Lettuce infectious yellows virus); *Comovirus* (e.g. cowpea mosaic virus); *Fabavirus* (e.g. broad bean wilt virus 1); *Nepovirus* (e.g. tobacco ringspot virus); *Potyvirus* (e.g. potato virus Y); *Rymovirus* (e.g. ryegrass mosaic virus); *Bymovirus* (e.g. barley yellow mosaic virus); Sequivirus (e.g. parsnip yellow fleck virus); *Waikavirus* (e.g. rice tungro spherical virus); *Carmovirus* (e.g. carnation mottle virus); *Dianthovirus* (e.g. carnation ringspot virus); *Machlomovirus* (e.g. maize chlorotic mottle virus); *Necrovirus* (e.g. tobacco necrosis virus); *Tombusvirus* (e.g. tomato bushy stunt virus); *Capillovirus* (e.g. apple stem grooving virus); *Carlavirus* (e.g. carnation latent virus); *Enamovirus* (e.g. pea enation mosaic virus); *Furovirus* (e.g. soil-borne wheat mosaic virus); *Hordeivirus* (e.g. barley stripe mosaic virus); *Idaeovirus* (e.g. raspberry bushy dwarf virus); *Luteovirus* (e.g.barley yellow dwarf virus); *Marafivirus* (e.g. maize rayado fino virus); *Potexvirus* (e.g. potato virus X and clover mosaic viruses); *Sobemovirus* (e.g. Southern bean mosaic virus); *Tenuivirus* (e.g. rice stripe virus); *Tobamovirus* (e.g. tobacco mosaic virus); *Tobravirus* (e.g. tobacco rattle virus); *Trichovirus* (e.g. apple chlorotic leaf spot virus); *Tymovirus* (e.g. turnip yellow mosaic virus); and *Umbravirus* (e.g. carrot mottle virus).

The successful virus purification has been accomplished on the commercial scale, and in a manner that complies with the cGMP regulations. In some embodiments, the source organism is a plant, but while some variations of present embodiments include production of plant-based viruses, the embodiments described herein are not limited to the manufacture or the purification of viruses in plants. In some embodiments, a virus purification platform begins by growing plants in a controlled growth room, infecting the plants with virus replication, recovering the viruses by rupturing the cells with a disintegrator and removing the plant fiber from the liquid via a screw press.

In some embodiments, involving both plant-based and non-plant viruses, purification steps include concentrating the clarified extract using tangential flow system, wherein the cassette pore size, transmembrane pressure, and load of clarified extract per square meter of membrane surface area are controlled. Transmembrane pressure (TMP) is the pressure differential between the upstream and downstream sides of the separation membrane and is calculated based on the following formula: ((feed pressure+retentate pressure)/2)–permeate pressure. To ensure passage of the viruses through the ceramic to create a clarified extract, in some embodiments the feed pressure, the retentate pressure, and the permeate pressure are each controlled to obtain an appropriate TMP. The clarified extract is concentrated further with an ion-exchange column volume and washed with ion-exchange chromatography equilibration buffer. In some embodiments, a CAPTO™ Q ion-exchange column is equilibrated and the feed is loaded and collected in the flow-through fraction. The column is then washed to baseline and the host cell contaminants are stripped from the column with high salt.

In some embodiments associated with plant-based viruses, an extraction buffer is added before removing chlorophyll and other large cellular debris such as macromolecular fibers, organelles, lipids, etc. using tangential flow ceramic filtration. In some embodiments, ceramic filtration promotes the retention of chlorophyll from plant hosts, cell debris, and other impurities while optimizing for virus passage. Whether for plant-based or non-plant viruses, this approach—wherein the desirable matter (virus or antigen) passes through as permeate and impurities are retained as retentate—promotes the scalability of the process. Additionally, parameters such as transmembrane pressure, ceramic pore size, and biomass loaded per square meter are all controlled to ensure passage of the virus through the ceramic to create a clarified extract. Ceramic TFF systems are highly scalable and parameters such as TMP, cross flow velocity, pore size, and surface area can be scaled readily to accept larger amounts of biomass. Additional ceramic modules are easily added to the system. Feed, retentate, and permeate pressure can also be controlled to maintain efficient cross flow velocity allowing little to no fouling of system. In some embodiments, cross velocity and pressure differential are set and controlled to produce a TMP of approximately 10-20 psi allowing for efficient passage of virus at smaller and larger scales. Ceramic TFF systems are amenable to using highly efficient cleaning chemicals such as nitric acid, bleach, and sodium hydroxide allowing for cleaning studies to be performed addressing GMP requirements.

Whether for plant-based or non-plant viruses, a purification method according to multiple embodiments and alternatives, and otherwise consistent with the development of scalable and high-throughput methods for purifying viruses, utilizes at least one separation procedure using multi-modal chromatography to separate residual impurities from a virus on the basis of at least size differences between the virus and the impurities, and chemical interaction occurring between the impurities and one or more chromatography ligands. For example, conducting the at least one separation procedure with CAPTO® Core 700 chromatography resin (GE Healthcare Bio-Sciences) is included within the scope of embodiments. The CAPTO® Core 700 'beads' comprises octylamine ligands designed to have both hydrophobic and positively charged properties that trap molecules under a certain size, e.g. 700 kilodaltons (kDA). Because certain viruses are fairly large (e.g. greater than 700 kDA), and the bead exteriors are inactive, CAPTO® Core 700 chromatography permits purification of viruses by size exclusion, wherein the desirable matter (virus or antigen) passes through as permeate and impurities are retained as retentate.

In some embodiments, again for plant-based and non-plant viruses alike, prior to the multi-modal chromatography column, equilibration is performed with five column volumes of equilibration buffer. In some embodiments, the combined flow-through and wash fractions from CAPTO™ Q ion-exchange chromatography are loaded onto the multi-modal chromatography column and the virus is collected in the void volume of the column. The column is washed to baseline and stripped with high conductivity sodium hydroxide. Aspects of some embodiments provide for controlling the loading ratio, column bed height, residence time, and chromatography buffers during this step.

The purified virus is sterile filtered, for example with diafiltration, and stored.

With regard to antigens, through the practice of some embodiments of an inventive antigen purification platform described herein, the recombinant antigens H5 recombinant influenza hemagglutinin (rHA), H7 rHA, domain III of West Nile virus (WNV rDIII), and lassa fever virus recombinant protein 1/2 (LFV rGP1/2) have been produced and purified. Antigens for various embodiments herein can be from many sources, and may be produced using traditional recombinant protein manufacturing strategies, including bacterial, yeast, insect, mammalian or plant-based expression approaches.

In some embodiments, an antigen manufacturing platform begins by growing plants in a controlled growth room, infecting the plants for recombinant antigen replication, then antigen recovery using a disintegrator followed by removal of fiber from the aqueous liquid via a screw press. An extraction buffer is added to assist in removal of chlorophyll (in the plant context) and large cellular debris by filtration. Whether for plant-based or non-plant antigen, feed pressure, filtrate pore size, clarifying agent, and biomass loaded per square meter of membrane surface are controlled) to facilitate passage of the antigens through the filter. A description (though non-limiting) of various in-process controls suitable for achieving large scale virus and antigen purification is expressed in further detail in the Examples section.

In some embodiments, both plant-based and non-plant antigens alike, clarified extract is next concentrated with a tangential flow system. During this optional step, factors including cassette pore size, transmembrane pressure, and load of clarified extract per square meter of membrane surface are controlled. In some embodiments, the optional step is skipped entirely. Following this, clarified extract is next concentrated and washed with an ion-exchange chromatography equilibration buffer. One way for this step to be undertaken is by loading feed onto an equilibrated CAPTO™ Q ion-exchange column, followed by washing with equilibration buffer and eluting/stripping with salt. Antigen fractions are then collected in the elution and prepared for cobalt immobilized metal affinity chromatography (IMAC). The IMAC is equilibrated, the feed is loaded, then washed with equilibration buffer and eluted. The elution fraction is diluted and checked for pH, then loaded onto a multi-modal ceramic hydroxyapatite (CHT) chromatography column. The CHT resin is equilibrated with equilibration buffer and the antigens are eluted. Loading ratio, column bed height, residence time, and chromatography buffers are among factors being controlled. Lastly, the antigen is concentrated and diafiltered with a saline buffer. The recombinant antigen is sterile filtered and then stored.

Still further, in accordance with various embodiments disclosed herein, H7 rHA and TMV, H1N1 (Influenza A/Michigan) to TMV, H3N2 (Influenza A/Singapore) to TMV, and TMV to two Influenza B viruses (B/Colorado and B/Phuket), have been successfully conjugated. In some embodiments, the protein consists of any type of therapeutic agent capable of being conjugated to a virus to create a vaccine, and then delivered to a source organism to produce an immune response according to multiple embodiments and alternatives. Accordingly, the disclosures herein provide compositions comprising an array of virus-protein conjugates, including virus-antigen conjugates. In some embodiments, the virus selected is TMV, or any of a number of viruses identified and/or indicated by the teachings herein. Additionally, in some embodiments the protein can be an antigen, such as but not limited to influenza hemagglutinin antigen (HA), including without limitation ones listed in this paragraph. In some embodiments, the HA exhibits at least about 50% trimer formation. HAs are clinically important because they tend to be recognized by certain antibodies an organism produces, providing the main thrust of protection against various influenza infections. Because HA antigenicity and, therefore, HA immunogenicity are tied to conformation, it is known that HA trimerization is advantageous over the monomeric form in terms of triggering immune responses.

In some embodiments, conjugation begins by concentrating and diafiltering purified antigen and virus into a slightly acidic buffer. The antigen and virus are then combined based upon molarity and mixed. A freshly prepared water-soluble carbodiimide, such as 1-ethyl-3-(3-dimethylaminopropyl) carbodiimide (also known as EDC) is added to the mixture while mixing based upon molarity. A chemical reagent for converting carboxyl groups to amine reactive N-hydroxysulfosuccinimide esters, such as ThermoFisher's Sulfo-NHS, is then added based upon molarity. The reaction is continued until a predetermining stop time. The reaction is then quenched, with one exemplary involving the addition of an amine group (e.g., liquid containing free amines) and any chemical linker(s) used in facilitating the reaction (e.g., EDC, Sulfo-NHS) is removed through a multi-modal chromatography step or diafiltration, with the mixture then being diluted to target concentration. In some embodiments, the conjugated and purified virus particles that are decorated with proteins and antigens may be used for vaccines and/or diagnostic tools. These particles may be used as diagnostic tools because of their ability to track antigens in the host organism.

In some embodiments, the purified virus—antigen fusion may be derived from genetic fusion, in addition to the various embodiments disclosed herein. The antigen and virus structural proteins (located in the coat) form a single continuous open reading frame. In some embodiments, the reading frame produces an antigen-coat protein in a plant such that the coat protein self assembles into virus particles. Next, the plant materials are harvested and the virus particles are purified according to the embodiments disclosed herein. The virus particles decorated with the fusion-coat proteins may then be used as a vaccine and/or a diagnostic tool according to the various embodiments disclosed.

Some viruses (such as icosahedral viruses as a non-limiting example) swell under certain pH conditions and in some embodiments this "swelling" may be used for conjugation. According to multiple embodiments and alternatives, the purified virus may be conjugated to a therapeutic agent by subjecting the virus structure to acidic pH conditions that cause the virus to "swell." By treating the virus structure with neutral pH conditions, the virus structure relaxes and creates pores between pentamer or other structural subunits of the virus. Next, a therapeutic agent (such as a chemotherapeutic agent), is added to the buffer and allowed to diffuse into the relaxed virus particle. By changing the pH again, the virus particles tighten and remove the pore structures packing the pentamer or structural submits together such that chemical diffusion in or out of the virus particle is prevented. Next, the plant materials are harvested, the virus particles are purified, and the virus particles containing a therapeutic agent are used for drug delivery, according to the embodiments disclosed herein.

Accordingly, multiple embodiments and alternatives encompass production of one or more highly purified viruses. Still further, multiple embodiments and alternatives encompass production or purification or both of a recombinant antigen. Still further, multiple embodiments and alternatives encompass conjugation of purified antigens and viruses for use as vaccines. The purification of viruses may be practiced by itself in accordance with the present embodiments. Likewise, the production or purification of recombinant antigens may be practiced alone in accordance with the present embodiments. Optionally, as well, different aspects of these multiple embodiments can be combined, in which combining embodiments would include, among other ways of practicing these embodiments, starting with one or more source organisms, from which are produced one or more viruses and one or more antigens, then purifying such viruses and antigens, then forming vaccines which are conjugates between at least one antigen and at least one virus.

BRIEF DESCRIPTION OF THE FIGURES

The drawings and embodiments described herein are illustrative of multiple alternative structures, aspects, and features of the multiple embodiments and alternatives disclosed herein, and they are not to be understood as limiting the scope of any of these embodiments and alternatives. It will be further understood that the drawing figures described and provided herein are not to scale, and that the embodiments are not limited to the precise arrangements, depictions, and instrumentalities shown.

MULTIPLE EMBODIMENTS AND ALTERNATIVES

A multi-set process according to multiple embodiments and alternatives herein improves upstream purification processes, further enriching plant viruses, and facilitates the conjugation of virus and antigen to form a vaccine. Steps for producing and purifying a virus in accordance with multiple embodiments and alternatives are listed and discussed in connection with Table 1 and FIG. 1. Likewise, steps for producing and purifying an antigen are listed and discussed in connection with Table 2. Although the various platforms have a specific embodiment described for them below, the scope of the embodiments contained herein are not limited to any one specific embodiment.

Virus Production and Purification

Figure 1:
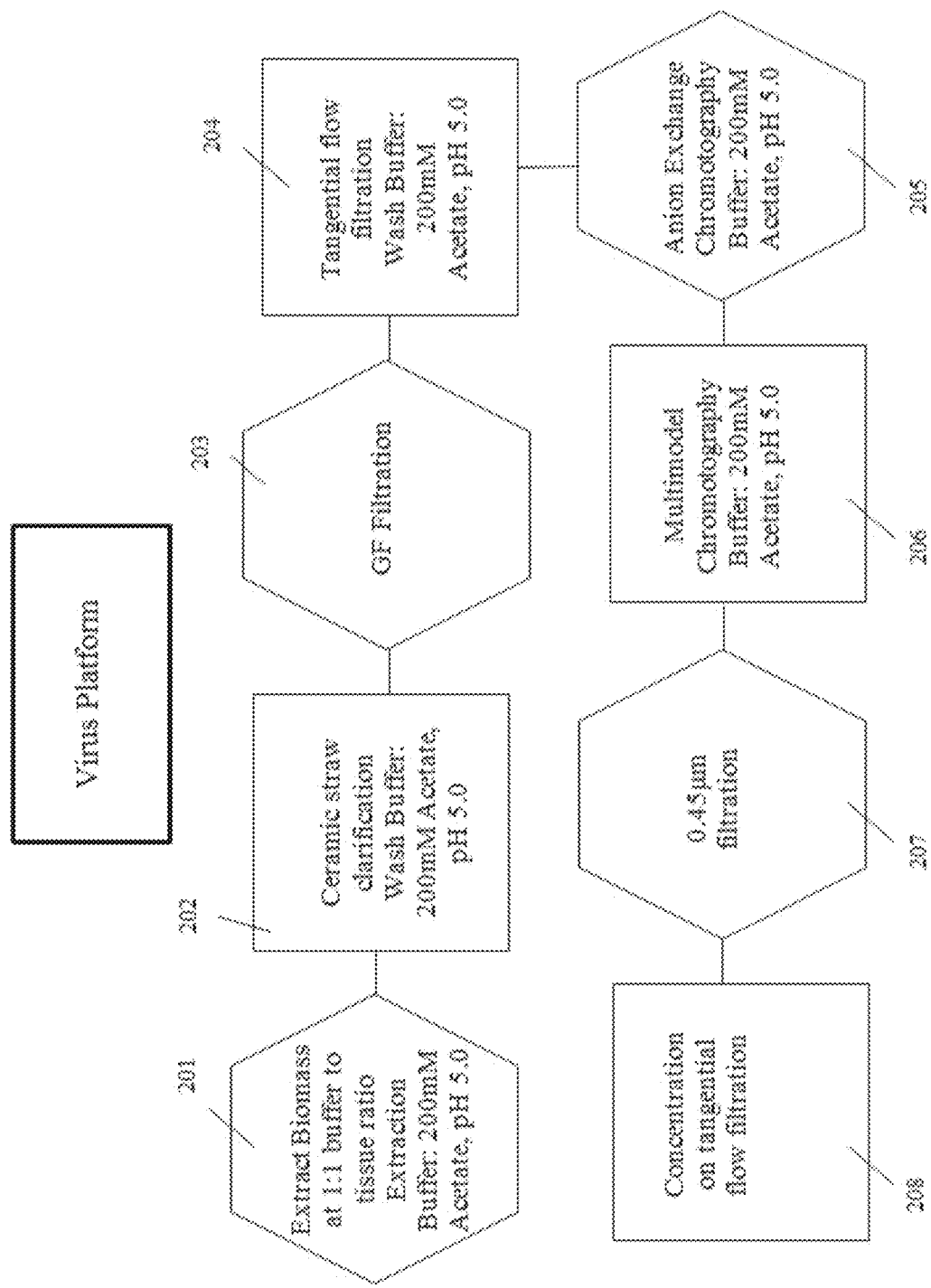
FIG. 1 is a flow chart showing the steps in a certain virus purification platform within the scope of the present disclosure, according to multiple embodiments and alternatives.

Table 1 and FIG. 1 illustrate the steps of the virus purification platform according to multiple embodiments and alternatives.

TABLE 1

Production and Purification of Virus

| Operative Steps | Unit Operations | In-Process Controls | In-Process Analytics |
| --- | --- | --- | --- |
| 1 | Plant Growth (25 DPS) Nb | Irrigation, Light Cycle, Fertilizer, Media, Humidity, Temperature | Plant Height, structure and leaf quality |
| 2 | Infection with virus | Inoculum Concentration, Rate of Application | N/A |
| 3 | Viral Replication (7 DPI) Plant Growth | Irrigation, Light Cycle, Humidity, Temperature | N/A |
| 4 | Harvest of Aerial Tissue | Visual Inspection of Plants | N/A |
| 5 | Disintegration of Plant Cells (Extraction) | Blade Type and RPM, Screen Sizes, Buffer:Tissue Ratio | pH, Conductivity, SDSPage, Endotoxin, Nicotine |
| 6 | Clarification of Plant Extract | Ceramic Size, TMP, kg/m$^2$ | pH, Conductivity, SDSPage, Endotoxin, Nicotine |
| 7 | Concentration of Clarified Plant Extract | Pore Size, TMP, Pore Material, kg/m$^2$ | pH, Conductivity, SDSPage, Endotoxin, Nicotine |
| 8 | Ion-Exchange Chromatography | kg/L, Bed Height, Residence Time | pH, Conductivity, SDSPage, Endotoxin, Nicotine |
| 9 | Multi-Modal Chromatography | kg/L, Bed Height, Residence Time | pH, Conductivity, SDSPage, Endotoxin, Nicotine |
| 10 | Concentration of Purified Virus | Pore Size, TMP, Pore Material, kg/m$^2$ | UV260, TEM, DLS, SDSPage, Endotoxin, Nicotine, Amino Acid |

This purification platform is designed for commercial scalability and compliance with the cGMP regulations and utilizes one buffer throughout the entire purification process. According to multiple embodiments and alternatives, the steps of the virus purification platform are given in connection with plant expression. However, steps after the aerial tissue harvesting and cell rupture as described below also would apply to non-plant viruses (except where context is clearly related to plants, e.g., reference to removal of plant fiber).

In accordance with multiple embodiments and alternatives described herein, virus expression is accomplished through methods that are appropriate for a particular host. In some embodiments, virus-based delivery of genes to a plant host is accomplished with a modified TMV expression vector that causes tobacco plants to recombinantly form the virus. One such available alternative is the GENEWARE® platform described in U.S. Pat. No. 7,939,318, "Flexible vaccine assembly and vaccine delivery platform." This transient plant-based expression platform described in this patent employs the plant virus TMV to harness plant protein production machinery, which expresses a variety of viruses in a short amount of harvest time post inoculation (e.g., less than 21 days). Tobacco plants inoculated with the virus genes express the particular virus in infected cells, and the viruses are extracted at harvest. Inoculation occurs by, as examples to be selected by a user of the methods herein described, hand inoculation of a surface of a leaf, mechanical inoculation of a plant bed, a high pressure spray of a leaf, or vacuum infiltration.

Besides *Nicotiana benthamiana*, other plant and non-plant hosts are contemplated by this disclosure, including those mentioned in the Summary. Besides the GENEWARE® platform, other strategies can be employed to deliver genes to plant (*Lemna gibba* or *Lemna minor* as non-limiting examples) and non-plant organisms (algae as a non-limiting example). These other strategies include Agro-infiltration, which introduces the viral gene via an *Agrobac-*

*terium* bacterial vector to many cells throughout the transfected plant. Another is electroporation to open pores in the cell membranes of the host to introduce the genes that recombinantly produce the viruses and antigens such as but not limited to those described in Examples 1 and 3 below. Another is TMV RNA-based overexpression (TRBO) vector, which utilizes a 35S promotor-driven TMV replicon that lacks the TMV coat protein gene sequence, as described in John Lindbo, "TRBO: A High-Efficiency Tobacco Mosaic Virus RNA-Based Overexpression Vector," Plant Physiol. Vol 145, 2007.

In some embodiments, growth of *Nicotiana benthamiana* wild type plants occurs in a controlled growth room. Plant growth is controlled via irrigation, light, and fertilized cycles. Plants are grown in a soilless media and temperature is controlled throughout the process.

After an appropriate number of days post sow (DPS), for example 23-25 DPS, the plants are infected with the virus replication. After infection, the plants are irrigated with water only and controlled via light cycle and temperature for a certain number of days post infection (DPI) depending on the type of virus.

Plants are inspected for height, infection symptoms, and the aerial tissue is harvested.

Virus recovery/cell rupture involves a disintegrator configured with an optimized blade/screen size followed by removal of residual cellulosic plant fiber from aqueous liquid (such as through a screw press, as one example).

An appropriate extraction buffer (e.g., 200 mM Sodium Acetate, pH 5.0; step 201 of FIG. 1 as a non-limiting example) is added to the resulting extract at a 1:1 buffer: tissue ratio. Removal of chlorophyll and large cellular debris at pilot scale involves the use of tangential flow (TFF) ceramic filtration (1.4 micron/5.0 micron). Transmembrane pressure, ceramic pore size and biomass loaded per square meter of membrane surface are all controlled to ensure passage of the virus through the ceramic. In some embodiments, the feed pressure, retentate pressure, and permeate pressure are set and controlled to produce a resulting transmembrane pressure in a range of about 1.5-2 Bar TMP.

Ceramic permeate is further clarified via the use of glass fiber depth filtration (step 203 of FIG. 1 as a non-limiting example).

Clarified extract is concentrated with a TFF system (available from Sartorius AG). Cassette pore size (100-300 kDa), an appropriate TMP as described herein, and load of clarified extract per square meter of membrane surface area are controlled.

The clarified extract is concentrated to NMT 2× the ion-exchange column volume and washed 7× with ion-exchange chromatography equilibration buffer (200 mM Sodium Acetate, pH 5.0, step 204 of FIG. 1 provides a non-limiting example). The CAPTO™ Q ion-exchange column is equilibrated for five column volumes with 200 mM Sodium Acetate, pH 5.0 (step 205 of FIG. 1 provides a non-limiting example), and the feed is loaded and collected in the flow-through fraction. The column is washed to baseline and host cell contaminants are stripped from the column with high salt.

The flow through and wash fractions are collected, combined and prepared for multi-modal CAPTO® Core 700 chromatography. The multi-modal chromatography column is equilibrated with five column volumes of equilibration buffer (200 mM Sodium Acetate, pH 5.0; step 206 of FIG. 1 provides a non-limiting example).

The combined flow-through and wash fractions from CAPTO™ Q ion-exchange chromatography are loaded onto the column and the virus collected in the void volume of the column. The column is washed to baseline and stripped with high conductivity sodium hydroxide. Loading ratio, column bed height, residence time and chromatography buffers are all controlled. Formulation and concentration of virus (step 208, FIG. 2) takes place in some embodiments with a TFF System (such as the Sartorius AG system). Pore size (30-300 kDa), an appropriate TMP as described herein, load per square meter of membrane surface area and pore material are all controlled. Virus is concentrated to an appropriate concentration, such as 10 mg/ml, and in some embodiments is diafiltered with an appropriate buffer, such as Sodium Phosphate. Formulated virus is sterilized and stored appropriately. In some embodiments, sterilization is provided via a PES filter.

All examples provided herein are meant as illustrative of various aspects of multiple embodiments and alternatives of any or all of virus production, virus purification, antigen production, antigen purification, and virus-antigen conjugation. These examples are non-limiting and merely characteristic of multiple alternative embodiments herein.

EXAMPLE 1

Purification of Icosahedral Red Clover Mosaic Virus

Figure 2:
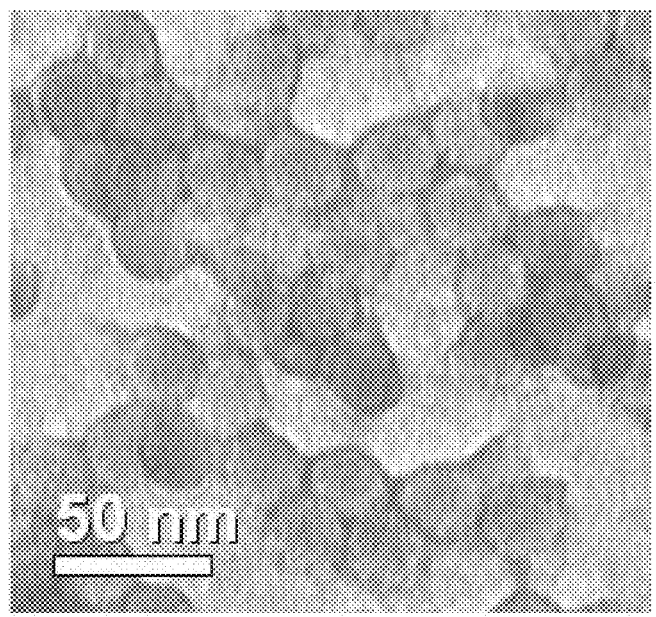
FIG. 2 is purified icosahedral red clover mosaic virus, according to multiple embodiments and alternatives.
Figure 3:
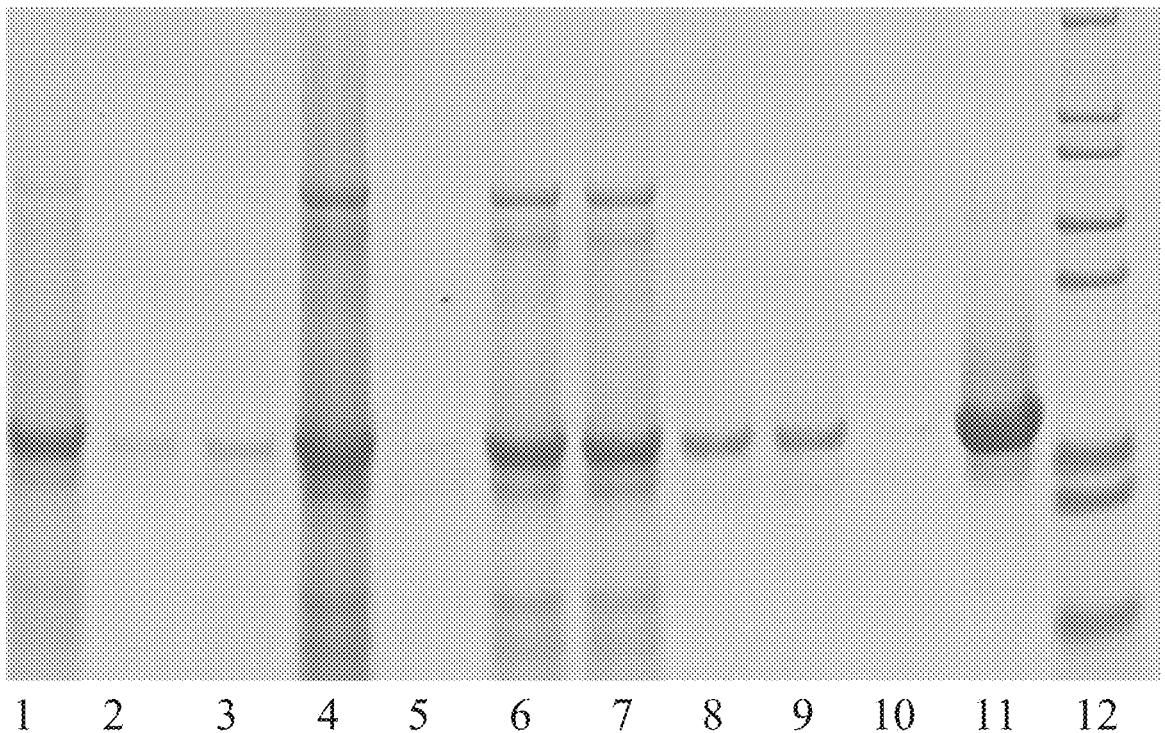
FIG. 3 is a western blot analysis of the purification of the icosahedral red clover mosaic virus, according to multiple embodiments and alternatives.
Figure 4:
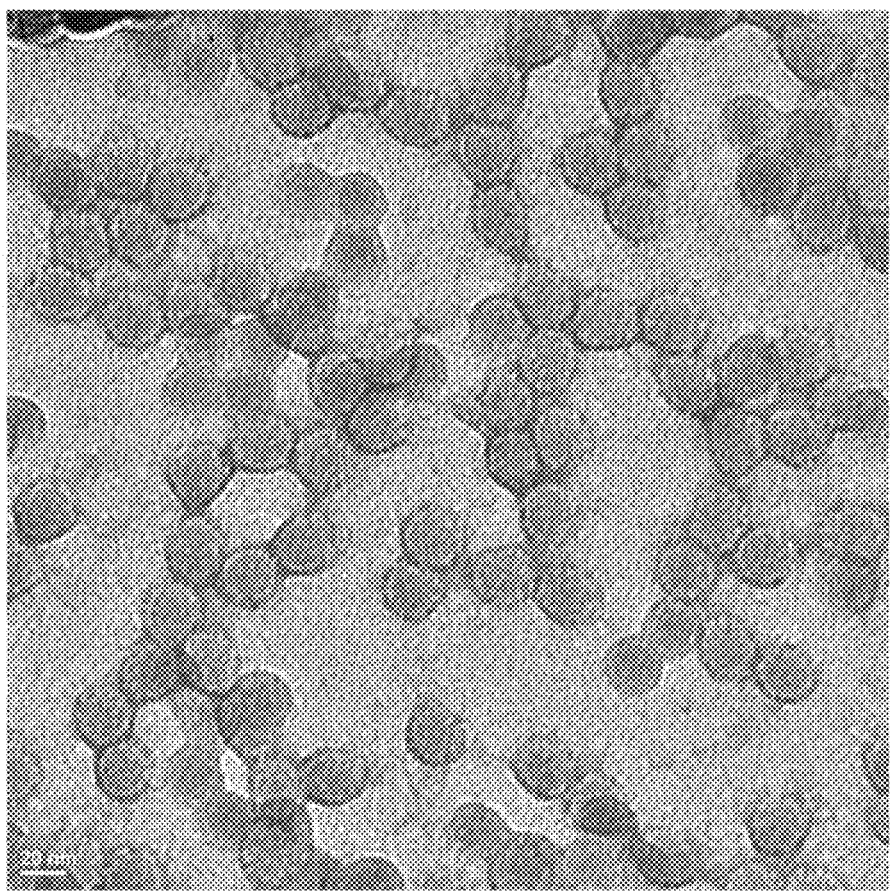
FIG. 4 is purified icosahedral red clover mosaic virus, according to multiple embodiments and alternatives.
Figure 5:
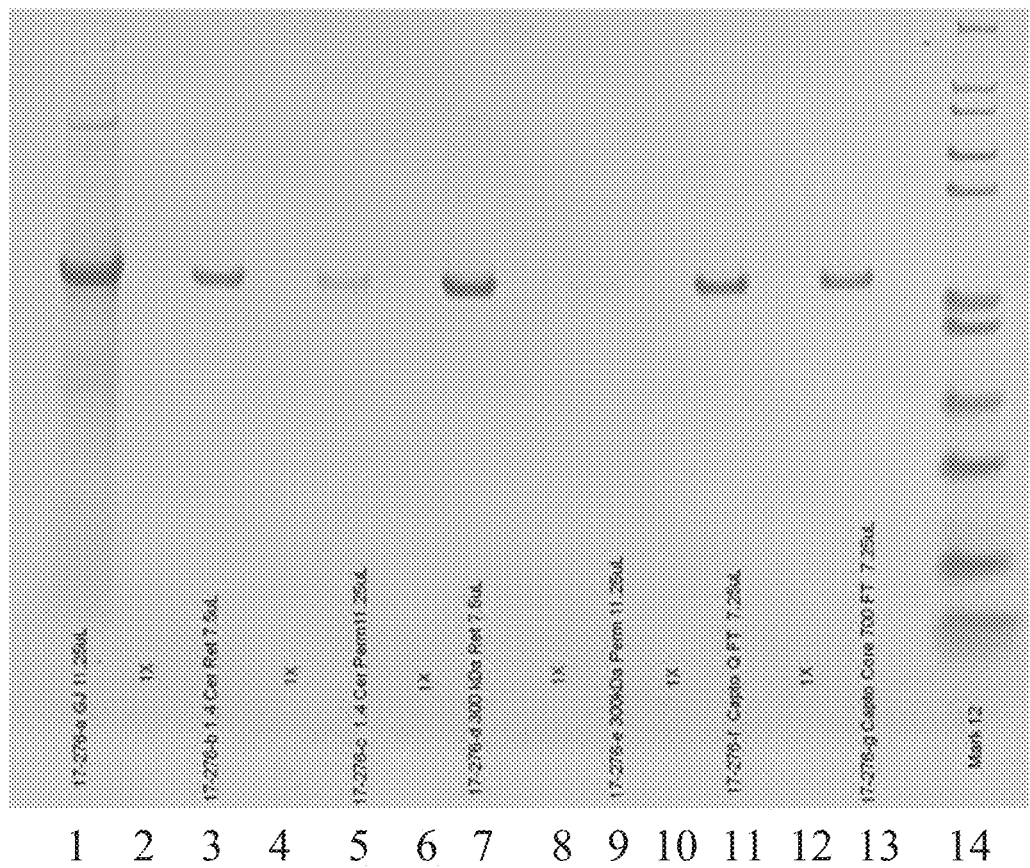
FIG. 5 is a western blot analysis of the purification of the icosahedral red clover mosaic virus, according to multiple embodiments and alternatives.

The Western Blot, provided in FIG. 3 as a known technique for detecting various proteins in a mixture, shows successful purification of the icosahedral red clover mosaic virus illustrated in FIG. 2. Similarly, the Western Blot in FIG. 5 shows successful purification of the icosahedral red clover mosaic virus illustrated in FIG. 4. Both viruses were purified according to the embodiments described herein. In accordance with the known detection technique, target proteins were extracted from the tissue. Then proteins of the sample were separated using gel electrophoreses based on their isoelectric point, molecular weight, electrical charge, or various combinations of these factors. Samples were then loaded into various lanes in the gel, with a lane reserved for a "ladder" containing a mixture of known proteins with defined molecular weights. For example, in FIG. 3, lane 12 serves as the ladder. A voltage was then applied to the gel, causing the various proteins to migrate through the gel at different speeds based on the aforementioned factors. The separation of the different proteins into visible bands within each lane occurred as provided in FIGS. 3 and 5, respectively. With the Western Blot, a more pure product is characterized by a clear and visible band, and such is characterized in these figures.

FIGS. 3 and 5 illustrate the virus purification platform successfully purifying the icosahedral red clover mosaic virus. Each lane of the western blot shows the purity of the virus after the conclusion of a different step in the virus purification platform. In FIG. 3, the lanes include: lane 1—green juice, lane 2—TFF Ceramic Clarification Retentate, lane 3—TFF Ceramic Clarification Permeate, lane 4—TFF Cassette Retentate, lane 5—TFF Cassette Permeate, lane 6—Ion Exchange, lane 7—Ion Exchange, lane 8—multimodal, lane 9—multimodal, lane 10—30K TFF Permeate, lane 11—30K Retentate, lane 12—marker. In FIG. 5. the lanes of the western blot include the following: lane 1—Green Juice, lane 3—TFF Ceramic Clarification Retentate, lane 5—TFF Ceramic Clarification Permeate, lane 7—TFF Cassette Retentate, lane 9—TFF Cassette Permeate, lane 11—Ion Exchange, lane 13—Multimodal, and Lane 14—Marker.

Once the final step has occurred in the virus purification platform, the resulting viral product is highly purified, as shown by the visible band in lane 11 of FIG. 3 and lane 13 of FIG. 5.

EXAMPLE 2

Purification of Rod-Shaped TMV

Figure 6:
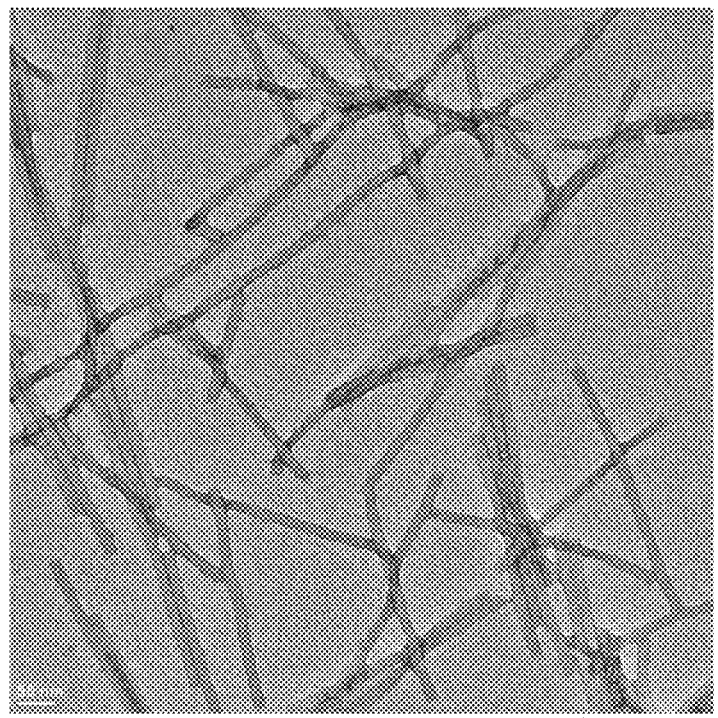
FIG. 6 is purified rod-shaped tobacco mosaic virus, according to multiple embodiments and alternatives.
Figure 7:
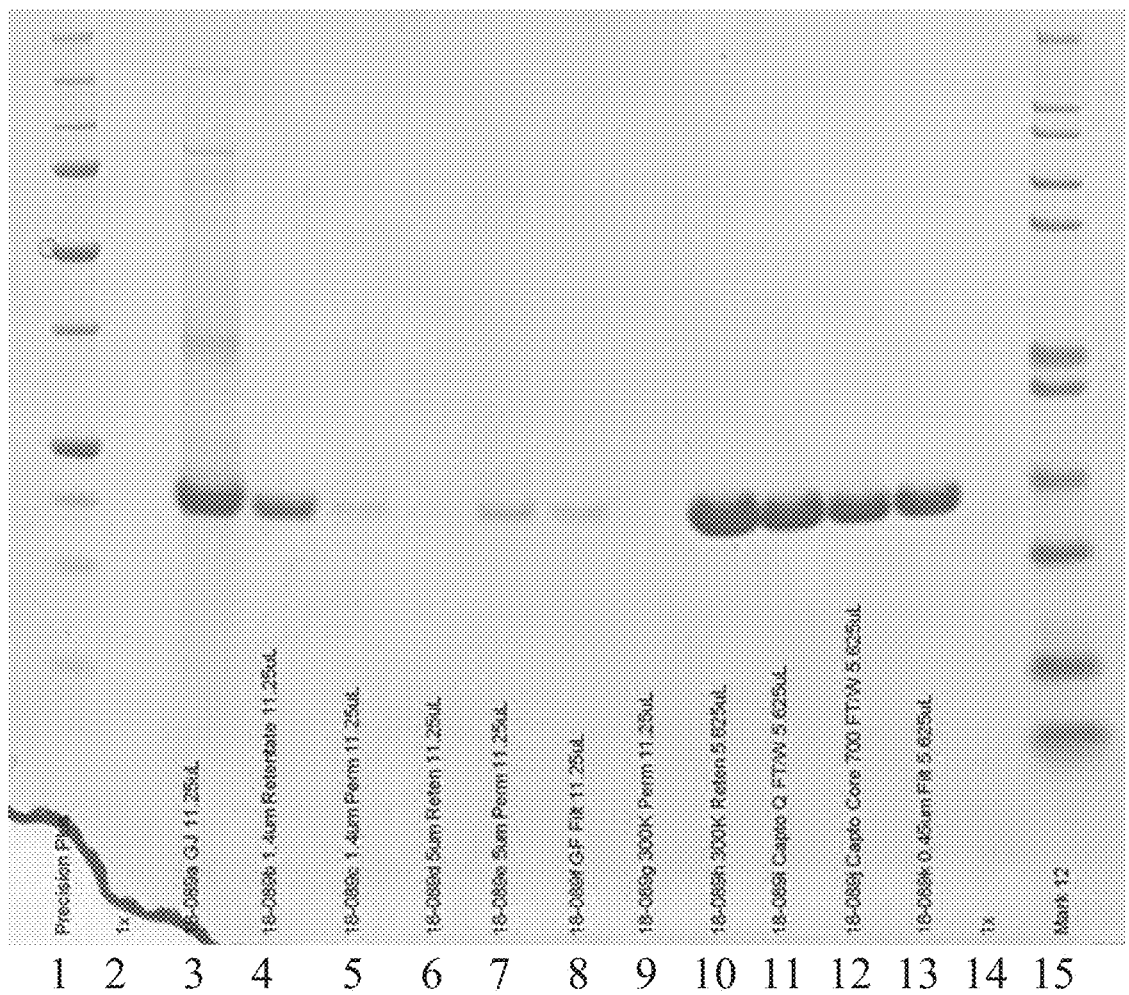
FIG. 7 is a western blot analysis of the purification of the rod-shaped tobacco mosaic virus, according to multiple embodiments and alternatives.

FIG. 6 shows a purified rod-shaped TMV, and FIG. 7 illustrates a virus purification platform used in achieving this purified TMV, within the scope of multiple embodiments and alternatives disclosed herein. Similar to FIGS. 3 and 5, FIG. 7 illustrates the purity of the virus product after the conclusion of the various steps of the current virus purification platform. After the final purification step, the resulting product is highly purified virus product consistent with a clear and visible band in lane 13 of FIG. 7.

Accordingly, an inventive virus purification platform has successfully purified every virus on which the inventors have applied these methods, including both an icosahedral virus and a rod-shaped virus, and this platform is expected to be reproducible and consistently purify on a commercial scale virtually any type (if not all types) of virus.

Production and Purification of Recombinant Antigen

Figure 8:
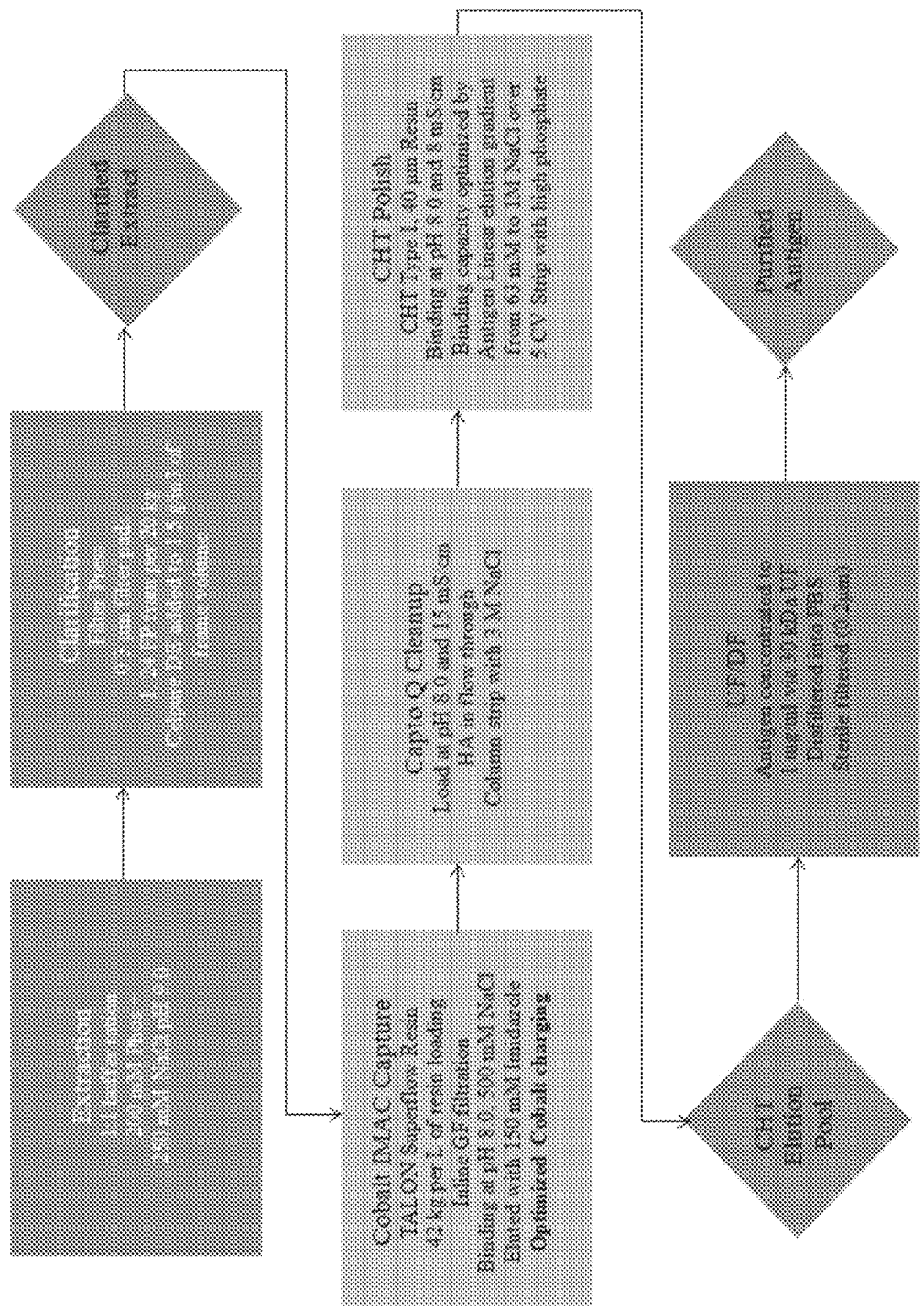
FIG. 8 is a flow chart showing the steps of an antigen manufacturing platform, according to multiple embodiments and alternatives.

Table 2 and FIG. 8 illustrate the steps of the antigen purification platform according to multiple embodiments and alternatives.

TABLE 2

Production and Purification of Recombinant Antigen

| Operative Steps | Unit Operations | In-Process Controls | In-Process Analytics |
|---|---|---|---|
| 1 | Plant Growth (25 DPS) Nb | Irrigation, Light Cycle, Fertilizer, Media, Humidity, Temperature | Plant height, structure and leaf quality |
| 2 | GENEWARE ® Infection with Target Antigen | Inoculum Concentration, Rate of Application | |
| 3 | Replication (7-14 DPI) Plant Growth | Irrigation, Light Cycle, Humidity, Temperature | |
| 4 | Harvest of Aerial Tissue | Visual Inspection of Plants | |
| 5 | Disintegration of Plant Cells (Extraction) | Blade Type and RPM, Screen Sizes, Buffer:Tissue Ratio | pH, Conductivity, SDSPage, Endotoxin, Nicotine |
| 6 | Clarification of Plant Extract | Filter Press Pore Size, Feed Pressure, kg/m2 | pH, Conductivity, SDSPage, Endotoxin, Nicotine |
| 7 | Concentration of Clarified Plant Extract | Pore Size, TMP, Pore Material, kg/m$^2$ | pH, Conductivity, SDSPage, Endotoxin, Nicotine |
| 8 | CAPTO ™ Q Chromatography | kg/L, Bed Height, Residence Time | pH, Conductivity, SDSPage, Endotoxin, Nicotine |
| 9 | ColMAC or ConA | kg/L, Bed Height, Residence Time | pH, Conductivity, SDSPage, Endotoxin, Nicotine |
| 10 | Ceramic Hydroxyapatite | kg/L, Bed Height, Residence Time | pH, Conductivity, SDSPage, Endotoxin, Nicotine |
| 11 | Concentration/Formulation of Purified Antigen | Pore Size, TMP, Pore Material, kg/m$^2$ | UV260, TEM, DLS, SDSPage, Endotoxin, Nicotine, Amino Acid |

This purification platform is designed for commercial scalability and compliance with the cGMP regulations and utilizes one buffer throughout the entire purification process. According to multiple embodiments and alternatives, the steps of the antigen purification platform are as follows:

Growth of Nicotiana benthamiana wild type plants in a controlled growth room. Plant growth is controlled via irrigation, light and fertilizer cycles. Plants are grown in a soilless media and temperature is controlled throughout the process. After an appropriate number of DPS, for example 23 to 25, plants are infected for protein replication of a selected antigen. Once tagged, the protein is sufficient for retention in the ER of the transgenic plant cell. After infection plants are irrigated with water only and controlled via light cycle and temperature for an appropriate number of days post infection, such as 7-14 days depending on the type of antigen. Plants are inspected for height and infection symptoms, and the aerial tissue is harvested.

Recovery of antigen produced by the plants involves a disintegrator configured with an optimized blade/screen size followed by removal of residual cellulosic plant fiber from aqueous liquid (such as through a screw press, as one example).

A suitable extraction buffer is added to the resulting extract at an appropriate ratio, such as a 1:1 buffer:tissue ratio or a 2:1 buffer:tissue ratio. In some embodiments, the extraction buffer may be 50-100 mM Sodium Phosphate+2 mM EDTA+250 mM NaCl+0.1% Tween80, pH 8.5. Removal of chlorophyll and large cellular debris involves the use of filtration. Celpure300 is added at a ratio of 33 g/L and mixed for 15 minutes. Feed pressure (<30 PSI), filtrate pore size (0.3 microns), clarifying agent (Celpure300) and biomass loaded per square meter of membrane surface are all controlled to ensure passage of the antigens.

Clarified extract is concentrated with a TFF system (such as the Sartorius AG system). In some embodiments, the cassette pore size (for e.g., 30 kDa), an appropriate TMP as described herein, and load of clarified extract per square meter of membrane surface area are controlled.

The clarified extract is concentrated and washed 7× with an appropriate ion-exchange chromatography equilibration buffer (such as 50 mM Sodium Phosphate+75 mM NaCl, pH 6.5). The CAPTO™ Q ion-exchange column is equilibrated for five column volumes with 50 mM Sodium Phosphate+75 mM NaCl, pH 6.5, the feed is loaded, washed with equilibration buffer, and the column eluted/stripped with high salt.

Antigen fractions are collected in the elution for preparation for Cobalt IMAC chromatography. IMAC is equilibrated for five column volumes with 50 mM Sodium Phosphate+500 mM Sodium Chloride, pH 8.0, feed is loaded, washed with equilibration buffer and eluted using imidazole.

The elution fraction is diluted to conductivity, pH is checked and loaded onto a multi-modal ceramic hydroxyapatite (CHT) chromatography column. The CHT resin is equilibrated with five column volumes of equilibration buffer (5 mM Sodium Phosphate, pH 6.5). Antigens are eluted using a gradient of phosphate and NaCl. Loading ratio, column bed height, residence time and chromatography buffers are all controlled. Formulation and concentration of the antigens takes place using a TFF system (such as the Sartorius AG system). Pore size (in kDa), TMP, load per square meter of membrane surface area and pore material are all controlled, as further discussed herein.

Antigen is next concentrated to a suitable concentration, such as 3 mg/ml, and diafiltered with a suitable buffer (for example, phosphate buffered saline, pH 7.4). Formulated antigen is sterilized and stored appropriately. In some embodiments, sterilization is provided via a PES filter.

Figure 9:
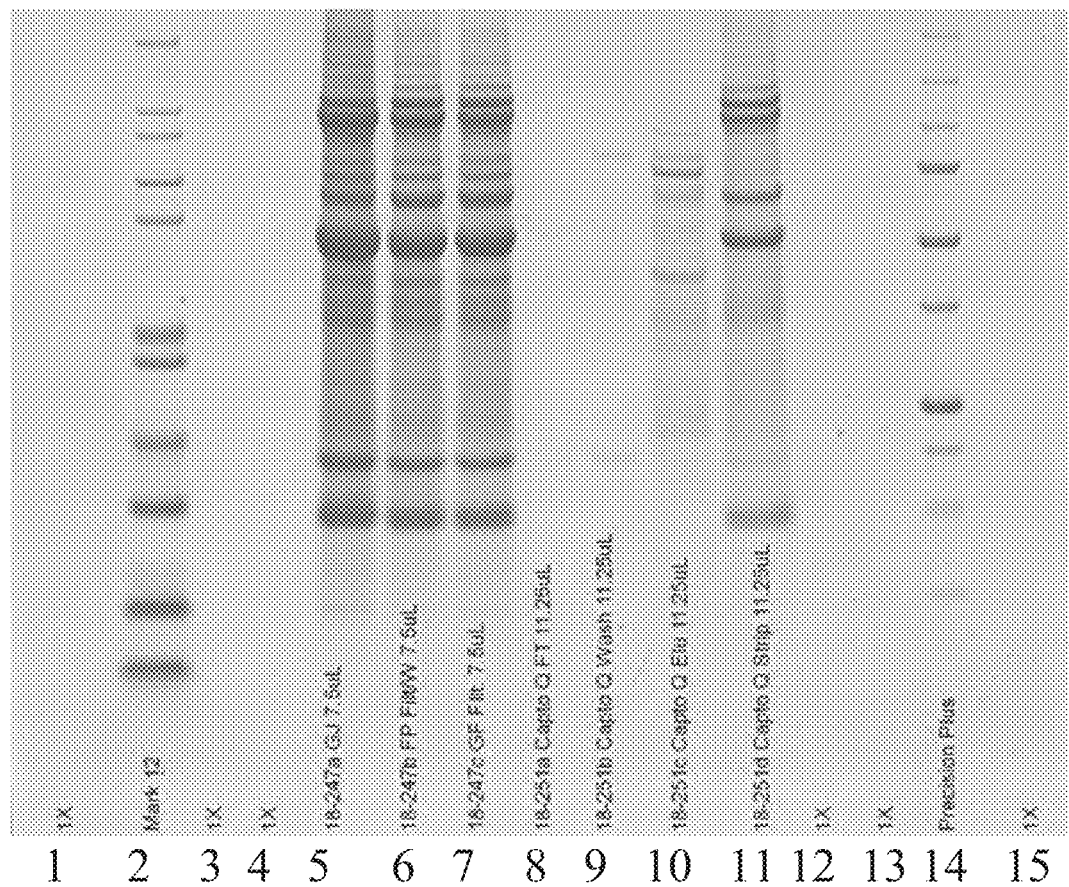
FIG. 9 is a western blot analysis of some of the steps of an antigen manufacturing platform, according to multiple embodiments and alternatives.
Figure 10:
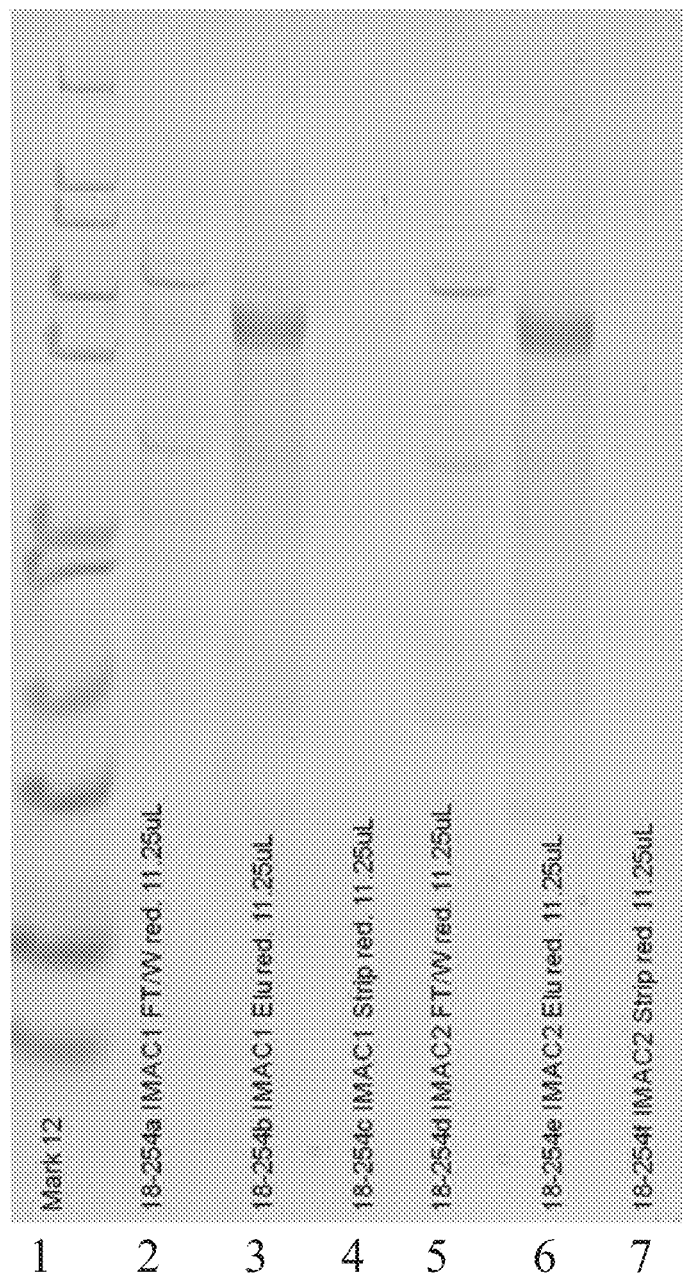
FIG. 10 is a western blot analysis of some of the steps of an antigen manufacturing platform, according to multiple embodiments and alternatives.
Figure 11:
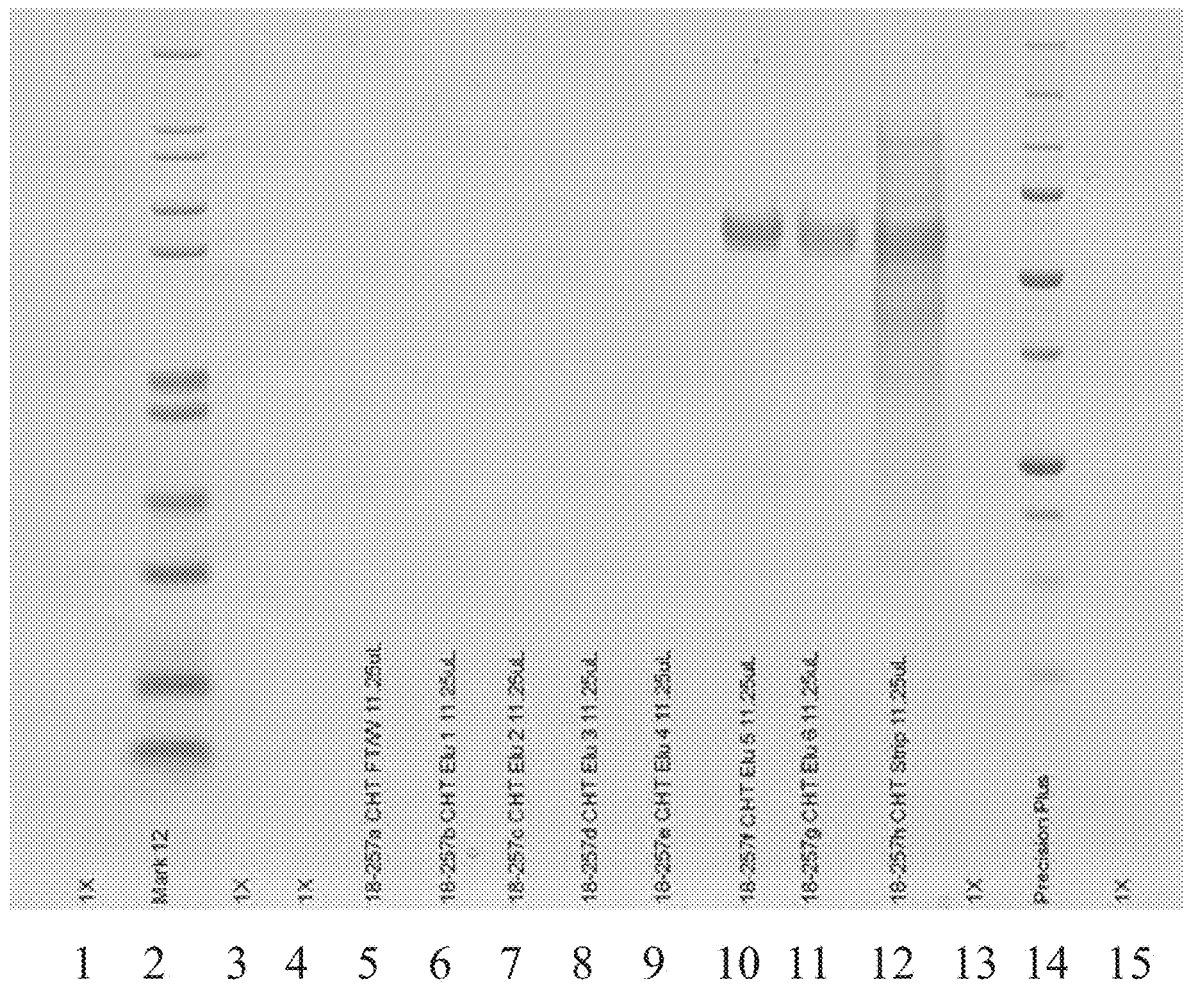
FIG. 11 is a western blot analysis of some of the steps of an antigen manufacturing platform, according to multiple embodiments and alternatives.

FIGS. 9, 10, and 11 illustrate the various steps of the antigen purification platform according to multiple embodiments and alternatives. FIG. 9 shows the purity of the antigen product after the CAPTO™ Q chromatography step has concluded, FIG. 10 shows the purity of the antigen product after the affinity chromatography step, and FIG. 11 shows the purity after the CHT chromatography column.

EXAMPLES 3, 4, 5, AND 6

H5 rHA, H7 rhA, WNV rDIII, and LFV rGP1/2

Figure 12:
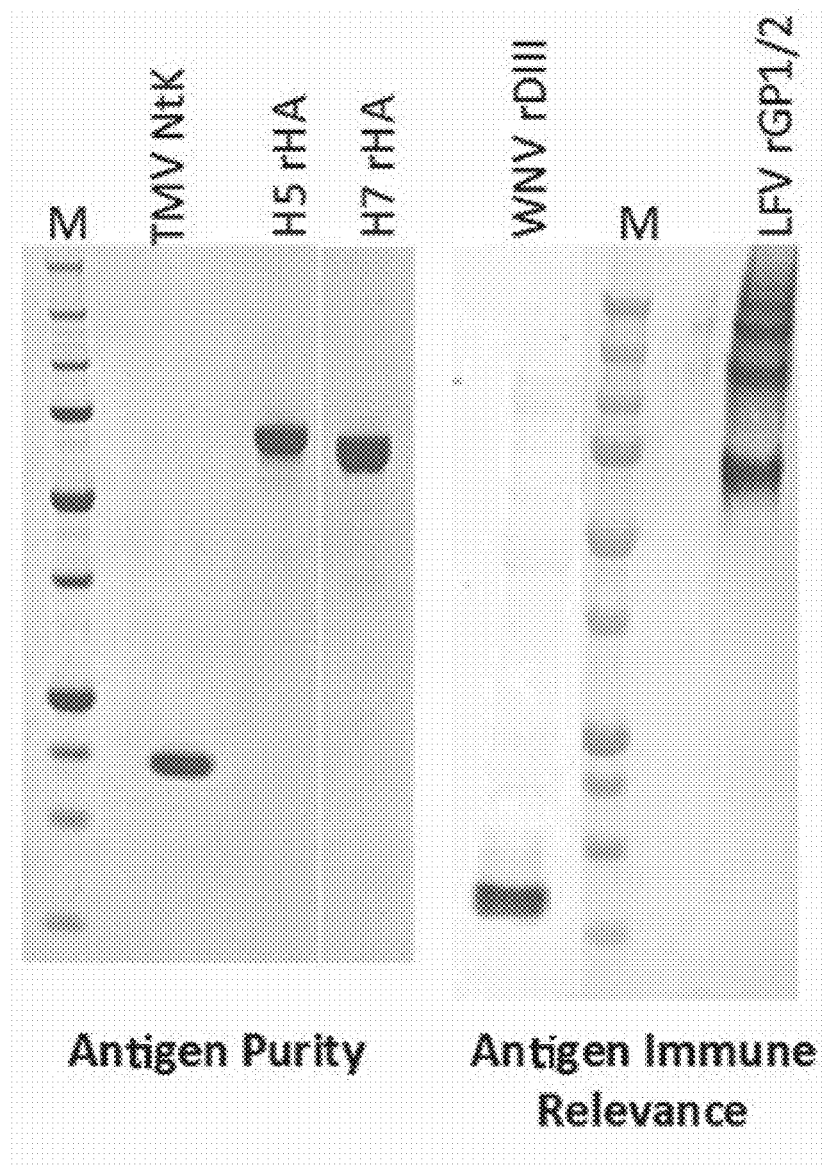
FIG. 12 is a western blot analysis of the purification of various antigens through the antigen manufacturing platform, according to multiple embodiments and alternatives.

As shown in FIG. 12, the antigen purification platform according to multiple embodiments and alternatives has successfully purified H5 rHA, H7 rhA, WNV rDIII, and LFV rGP1/2. FIG. 12 contains two images taken from the conclusion of the antigen purification platform: the image on the left contains a SDS Page gel indicating purity for the viral vector TMV NtK (where NtK is an abbreviation for N-terminal lysine) and influenza antigens, and the image on the right contains a western blot indicating the immunoreactivity for West Nile and Lassa Fever antigens. As shown by the clear and visible bands in FIG. 12, each antigen product is highly pure. Therefore, the antigen purification platform according to multiple embodiments and alternatives consistently purified each type of antigen on a commercial scale it was used with in a manner that is also compliant with cGMP regulations. In the same manner, this platform is expected to be reproducible to purify virtually any type (if not all types) of antigen.

Production of Recombinant Antigen—Virus Conjugates

Table 3 illustrates the steps of the conjugation of recombinant antigen according to multiple embodiments and alternatives.

TABLE 3

Production and Purification of Recombinant Antigen

| Operative Steps | Unit Operations | In-Process Controls | In-Process Analytics |
|---|---|---|---|
| 1 | Concentration/Diafiltration of Antigen | Pore Size, TMP, Pore Material, kg/m$^2$ | UV280 or BCA, SDSPage, pH, Conductivity |
| 2 | Concentration/Diafiltration of TMV 1295.10 | Pore Size, TMP, Pore Material, kg/m$^2$ | UV260, SDSPage, pH, Conductivity |
| 3 | Formulation of EDC Concentrate | Mixing, Weight Check | |

TABLE 3-continued

Production and Purification of Recombinant Antigen

| Operative Steps | Unit Operations | In-Process Controls | In-Process Analytics |
| --- | --- | --- | --- |
| 4 | Formulation of Sulfo-NHS Concentrate | Mixing, Weight Check | |
| 5 | Combine Antigen and TMV 1295.10 | Molar Ratio, Mixing, Volume | pH, Conductivity, SDSPage |
| 6 | Addition of EDC | EDC Molarity, Mixing, Volume | pH, Conductivity, SDSPage |
| 7 | Addition of Sulfo-NIIS | Sulfo-NHS Molarity, Mixing Volume | pH, Conductivity, SDSPage |
| 8 | Conjugation Reaction | Time, Temperature, Mixing | |
| 9 | Reaction Quenching | Time, Temperature, Mixing, Molarity of Amine Group | |
| 10 | Diafiltration to Remove Reactants | Pore Size, TMP, Pore Material, kg/m$^2$ | pH, Conductivity, SDSPage, Reactants (EDC/NHS) |
| 11 | Concentration/Formulation of Purified Vaccine (Drug Substance) | Pore Size, TMP, Pore Material, kg/m$^2$ | Certificate of Analysis |

In an embodiment, the steps of a conjugation platform are as follows:

Purified antigen and virus are separately concentrated and diafiltered into a slightly acidic buffer, such as a 2-(N-morpholino) ethanesulfonic acid (MES) buffer containing NaCl.

A water soluble carbodiimide, such as 1-ethyl-3-(3-dimethylaminopropyl) carbodiimide (known as EDC) is formulated in purified water to a molarity of 0.5 M.

A chemical reagent for converting carboxyl groups to amine reactive N-hydroxysulfosuccinimide esters, such as ThermoFisher's Sulfo-NHS, is formulated in purified water to a molarity of 0.1 M.

Antigen and virus are combined based upon weight or molarity and mixed to homogeneity (e.g. a 1:1 mg:mg addition).

The freshly prepared water soluble carbodiimide (such as EDC) is added to the mixture while mixing based upon molarity.

A chemical reagent for converting carboxyl groups to amine reactive esters (such as Sulfo-NHS) is added based upon molarity within one minute of EDC addition. The conjugation reaction begins and is continued until a predetermined mixing stop time, such as four hours, and the room temperature is controlled.

The reaction is quenched by adding free amines, and the chemical linker (for example EDC and Sulfo-NHS) is removed through a multi-modal chromatography step, such as CAPTO® Core 700 chromatography, or diafiltration into a phosphate buffered saline. According to multiple embodiments and alternatives, the residual impurities are removed from the conjugate mixture based on sized differences between impurities as the retentate, and the conjugate mixture as the permeate.

The conjugate mixture is diluted to target concentration. At this point, the virus-antigen conjugate is prepared for use as a purified vaccine/drug substance. A suitable delivery mechanism of the vaccine would include a liquid vial or lyophilized material to be reconstituted with physiologic buffering for project injection. Injection could be intramuscular or sub-cutaneous. Other delivery methods are contemplated, including without limitation intra-nasal.

EXAMPLE 7

Conjugation of H7 rhA to TMV

Figure 13:
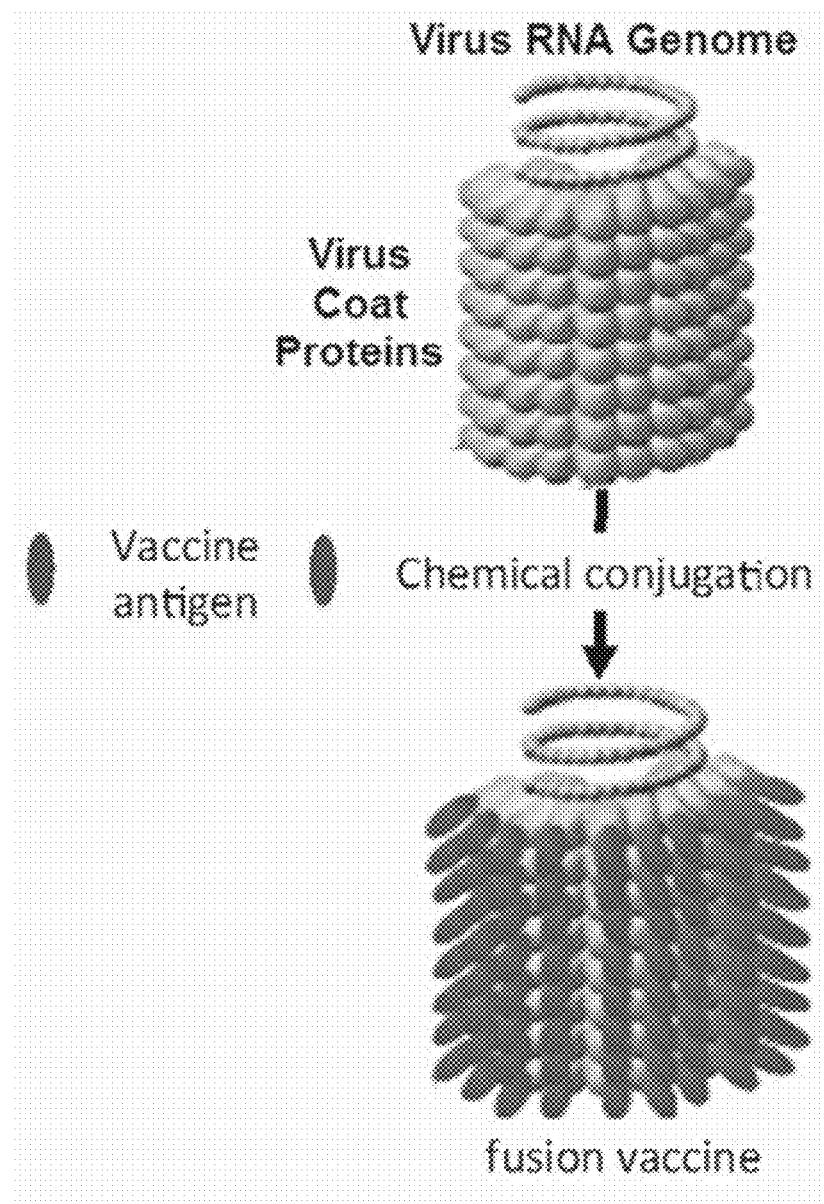
FIG. 13 is an illustration of the conjugation of recombinant antigen to a virus, according to multiple embodiments and alternatives.

FIG. 13 provides an illustration of the conjugation of a recombinant antigen (denoted by the "vaccine antigen") to a virus, with lighter- and darker-shaded ovals representing the extent of conjugation for the vaccine antigen depicted in the example. The lighter shade represents free virus, while the darker shade represents antigen conjugated to the protein coat of the virus. Also, as indicated in FIG. 13, some viruses contain coat positioned proteins around the RNA genome. For example, the viral vector TMV NtK includes N-terminal lysines that serve as connector points to the coat proteins. In some embodiments, portions of the virus associated with N-terminal lysine residues are modified to enhance presentment for binding of recombinant antigen providing amine-targeted conjugation of the protein, for example antigen to virus. In connection with the discussion of radial measurement herein, the viral radius greatly increases following conjugation of the recombinant antigens to the viral coat proteins. In some embodiments, modification is performed when enveloped viruses are changed to allow enhanced presentment of their residues.

Figure 14:
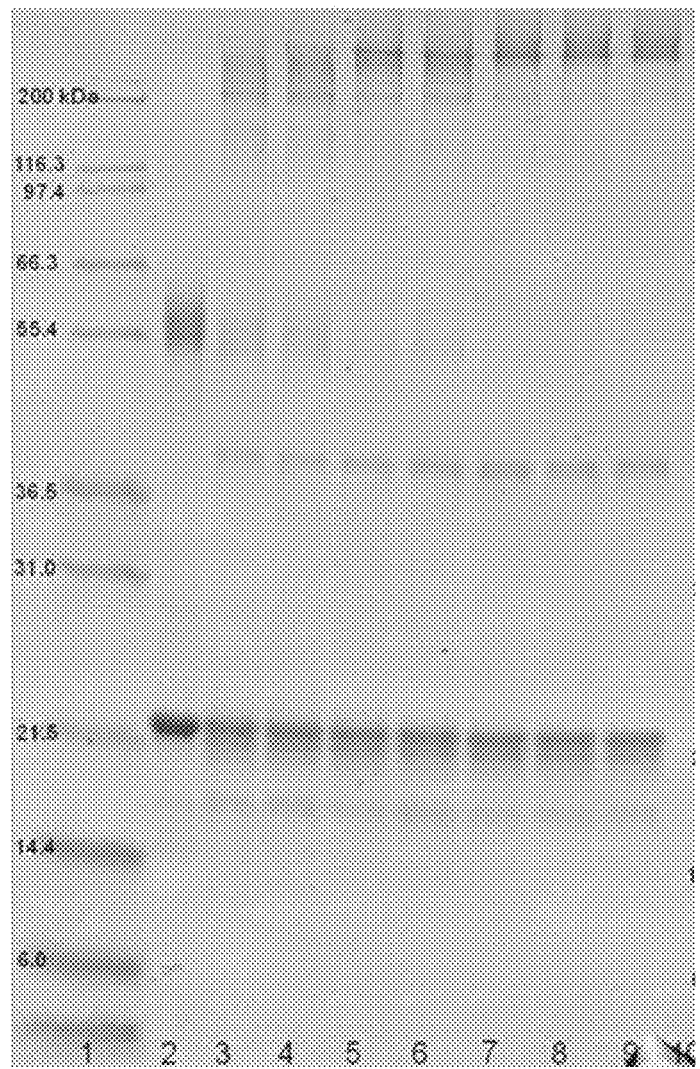
FIG. 14 is a SDS-PAGE analysis of the conjugation of an antigen to a virus, according to multiple embodiments and alternatives.
Figure 15:
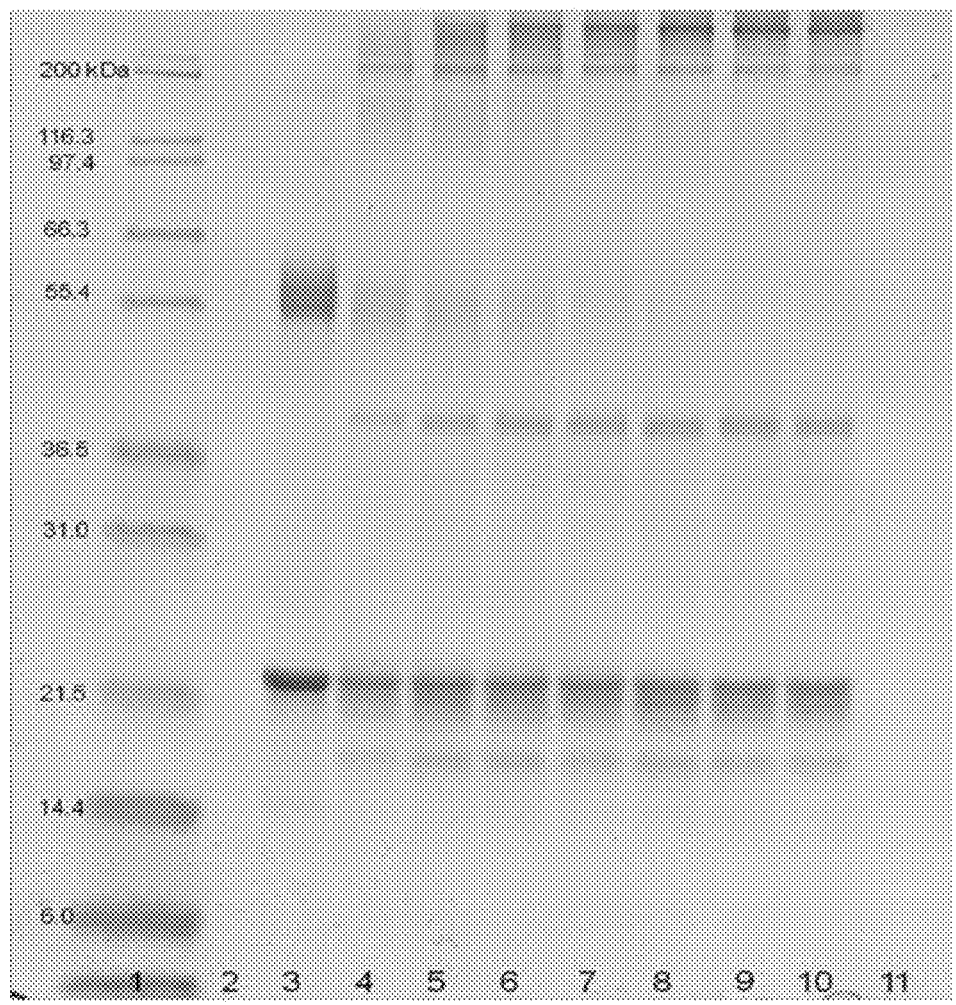
FIG. 15 is a SDS-PAGE analysis of the conjugation of an antigen to a virus, according to multiple embodiments and alternatives.
Figure 16:
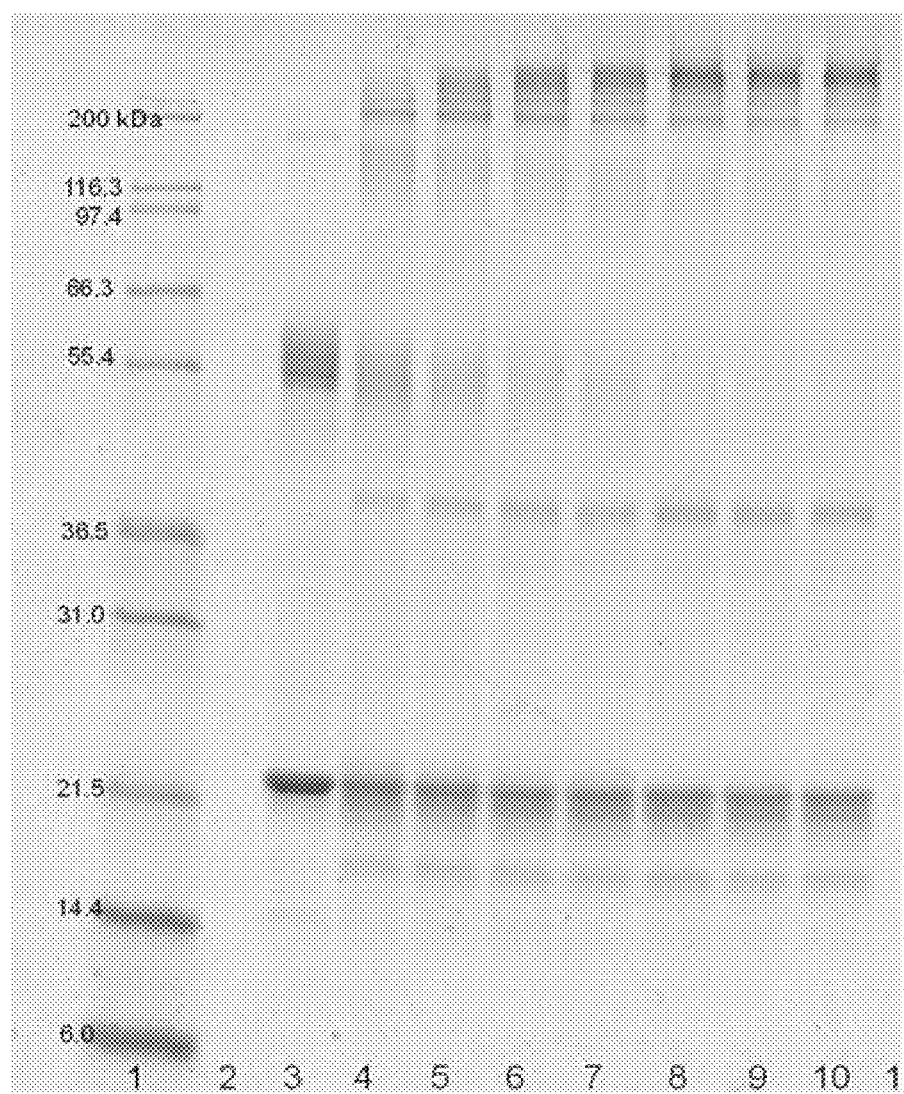
FIG. 16 is a SDS-PAGE analysis of the conjugation of an antigen to a virus, according to multiple embodiments and alternatives.

As shown in FIGS. 14-20, the conjugation platform of recombinant antigen to virus has successfully conjugated H7 rHA to TMV. FIGS. 14-16 show an analysis based on sodium dodecyl sulfate-polyacrylamide gel electrophoresis ("SDS-PAGE") of the conjugation between H7 rHA to TMV at pH 5.50. As illustrated in these figures, nearly all of the H7 rHA was conjugated to the TMV within 2 hours. The disappearance of the rHA protein band and simultaneous appearance of complexes staining above the 200KDa marker indicates the complex formation. The reactivity of the bands with HA-specific antibodies further establishes this conclusion.

Figure 17:
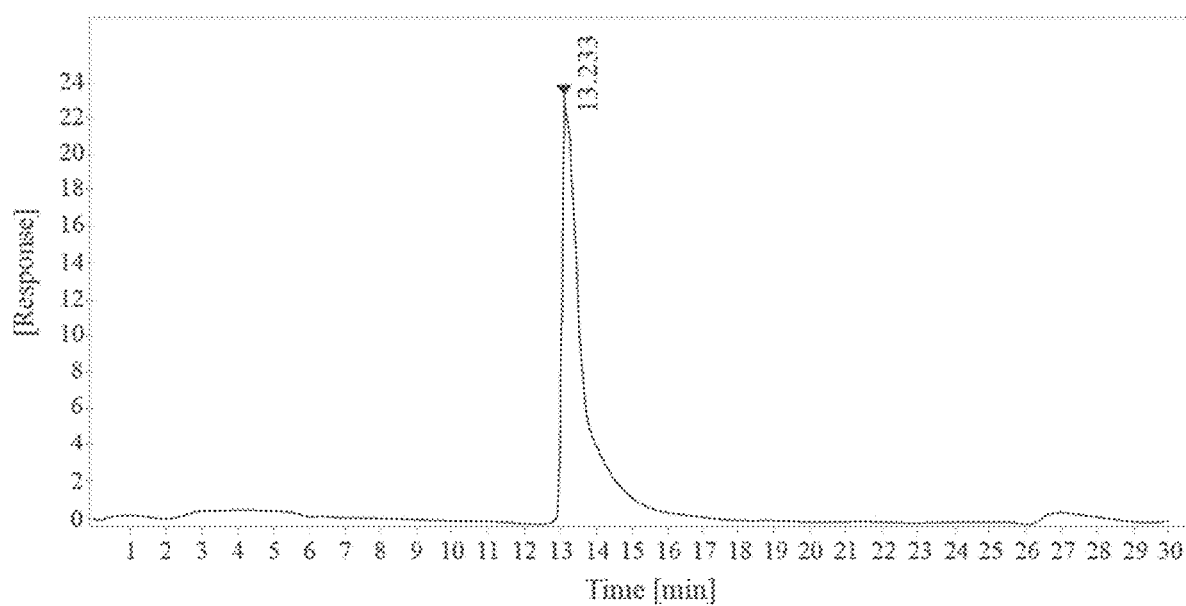
FIG. 17 is a report of size exclusion-high-performance liquid chromatography (SEC-HPLC) of a free TMV product, according to multiple embodiments and alternatives.

SEC-HPLC reports also indicated successful conjugation of H7 rHA to TMV in accordance with the current embodiments of the conjugation platform. FIG. 17 shows a SEC-HPLC report of free TMV product. In FIG. 17, the SEC-HPLC report of the free TMV product produced the signal data detailed in Table 4 below.

TABLE 4

SEC-HPLC Data of Free TMV

| RT [min] | Width [min] | Area | Height | Area % | Peak Symmetry |
|---|---|---|---|---|---|
| 13.233 | 0.77 | 1078.39 | 23.41 | 100 | 0.39 |

Figure 18:
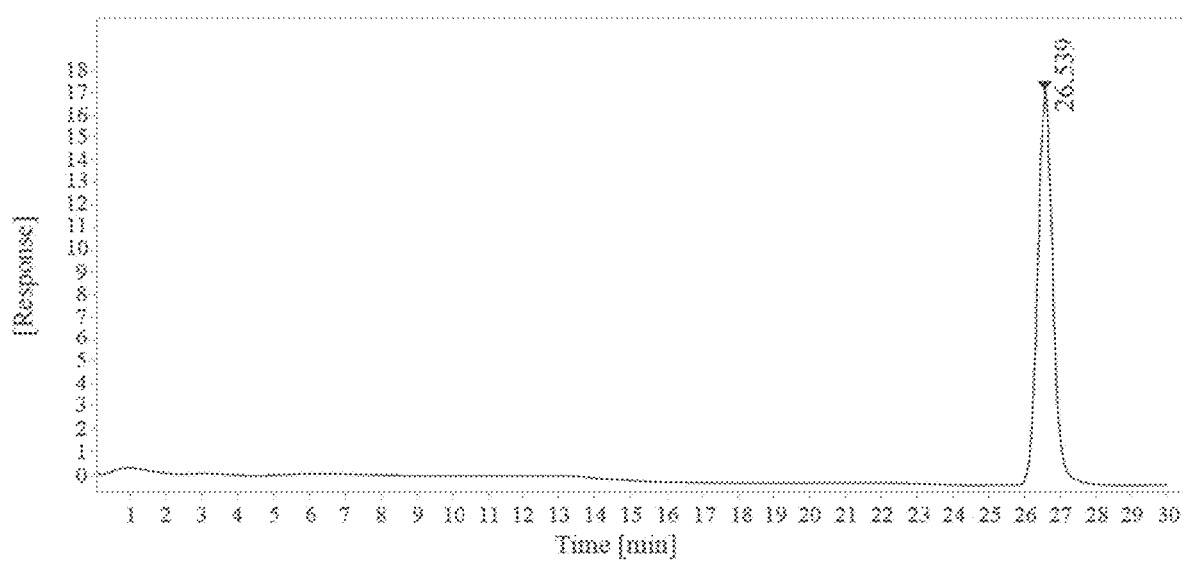
FIG. 18 is a report of SEC-HPLC of conjugation between a virus and an antigen for fifteen minutes, according to multiple embodiments and alternatives.

FIG. 18 shows a SEC-HPLC report after H7 rHA is conjugated to TMV for fifteen minutes according to current embodiments of the conjugation platform. In FIG. 18, the SEC-HPLC report after H7 rHA is conjugated to TMV for fifteen minutes produced the signal data detailed in Table 5.

TABLE 5

SEC-HPLC Data After H7 rHA is conjugated to TMV for 15 Minutes

| RT [min] | Width [min] | Area | Height | Area % | Peak Symmetry |
|---|---|---|---|---|---|
| 26.539 | 0.52 | 553.75 | 17.65 | 100 | 0.83 |

Figure 19:
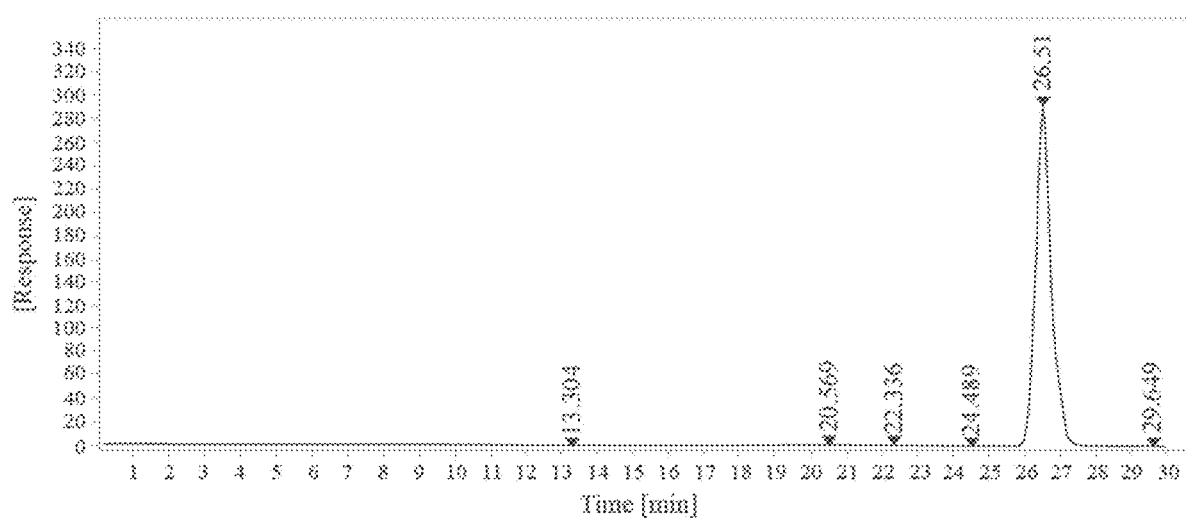
FIG. 19 is a report of SEC-HPLC of conjugation between a virus and an antigen two hours, according to multiple embodiments and alternatives.

FIG. 19 shows a SEC-HPLC report after H7 rHA is conjugated to TMV for two hours according to current embodiments of the conjugation platform. In FIG. 19, the SEC-HPLC report taken after H7 rHA is conjugated to TMV for two hours according to current embodiments of the conjugation platform produced the signal data detailed in Table 6 below.

TABLE 6

SEC-HPLC Data After H7 rHA is conjugated to TMV for 2 Hours

| RT [min] | Width [min] | Area | Height | Area % | Peak Symmetry |
|---|---|---|---|---|---|
| 13.304 | 0.73 | 37.30 | 0.86 | 0.36 | 0.43 |
| 20.569 | 1.83 | 167.16 | 1.52 | 1.59 | 0.00 |
| 22.336 | 1.17 | 62.55 | 0.89 | 0.59 | 0.64 |
| 24.489 | 2.05 | 73.35 | 0.60 | 0.70 | 1.34 |
| 26.510 | 0.54 | 10153.91 | 316.30 | 96.56 | 0.80 |
| 29.649 | 0.83 | 21.16 | 0.42 | 0.20 | 2.15 |

Figure 20:
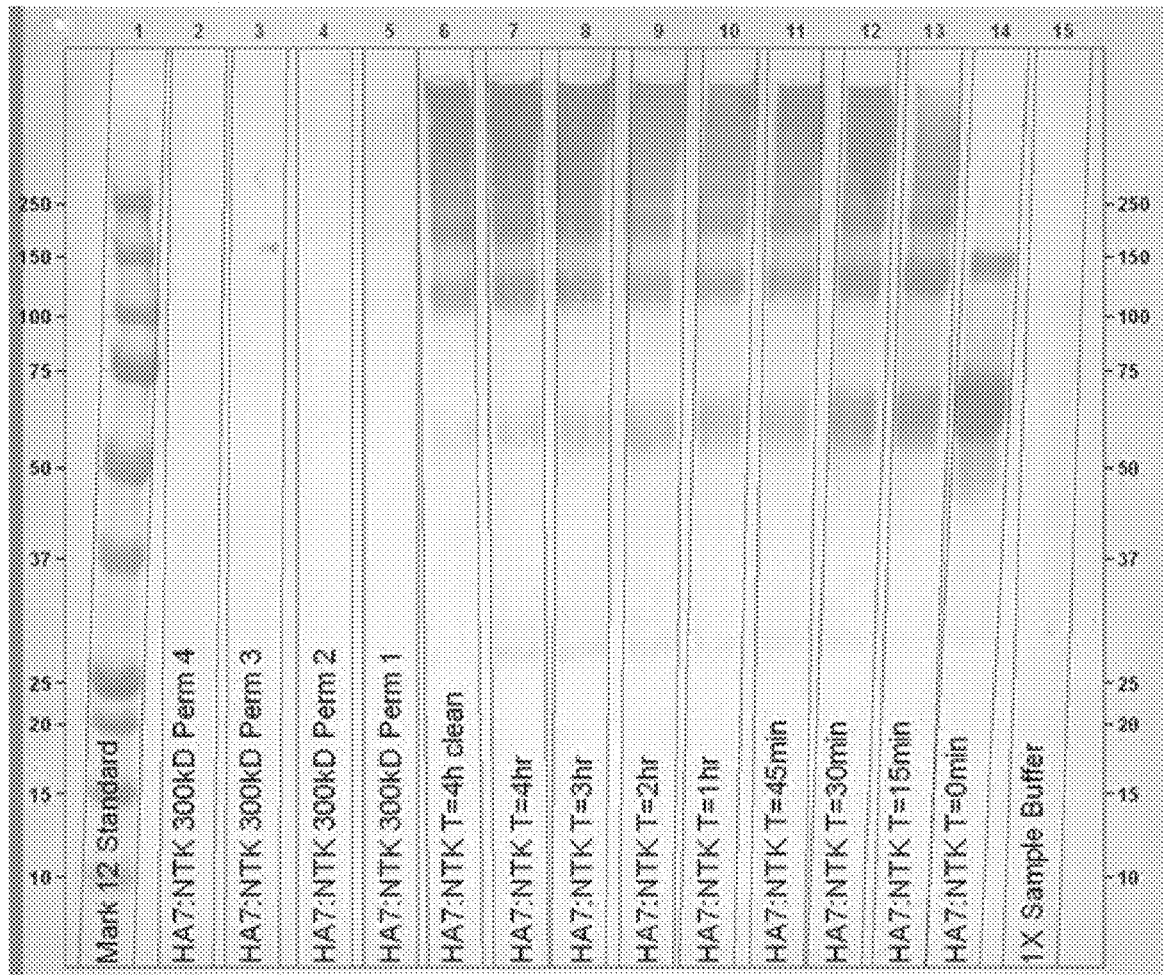
FIG. 20 is a western blot analysis of conjugation between a virus and an antigen, according to multiple embodiments and alternatives.

As illustrated in FIGS. 19 and 20, the SEC-HPLC reports indicated that all TMV rods were coated with some H7 rhA after conjugation for fifteen minutes, and more H7 rhA was added to the rods for up to two hours. After two hours, no additional conjugation was detected. According to multiple embodiments and alternatives, the SEC-HPLC reports indicate that the conjugation reaction achieves at least about 50% reduction in non-conjugated, native molecular weight, virus coat protein, and that approximately 3% free TMV remained after conjugation took place for four hours.

As illustrated in FIG. 20, western blot analysis of the conjugate product indicated successful conjugation of H7 rhA to TMV via covalent attachment. FIG. 20 shows a western blot analysis of the various steps of the conjugation platform according to current embodiments, wherein all samples were loaded at 10 µL. The various lanes illustrate different conjugation reaction times between the antigen and the virus. Lanes 14 and 13 show that all the TMV rods were coated with the antigen after fifteen minutes. After two hours, lanes 6-9 illustrate that no additional conjugation took place.

EXAMPLE 8

UV Inactivation of TMV NtK

In order to avoid viral contamination of biopharmaceutical products, it is often necessary to inactivate (or sterilize) the virus to ensure the virus is no longer infectious. In addition, many regulatory agencies have enacted rules (such as the cGMP regulations) that require at least one effective inactivation step in the purification process of viral products. While UV-C radiation has been used in water treatment systems for many years, its use with biopharmaceutical products remains unexplored and there are limited studies regarding its ability to effectively inactivate viruses.

Accordingly, following virus production and purification but prior to conjugation with recombinant antigen, various UV-C conditions (i.e. energy density and wavelength) and various TMV concentrations were evaluated in order to effectively inactivate and sterilize TMV NtK. While many energy densities were tested, only the higher levels of energy densities successfully inactivated TMV NtK. In addition, it was determined that successful virus inactivation is concentration dependent because when the TMV solution was not diluted to an appropriate concentration, the UV-C irradiation did not effectively sterilize every virus in the sample. Therefore, the TMV solution must be appropriately dilute to permit the UV-C irradiation to interact with and effectively inactivate each virus.

Figure 21:
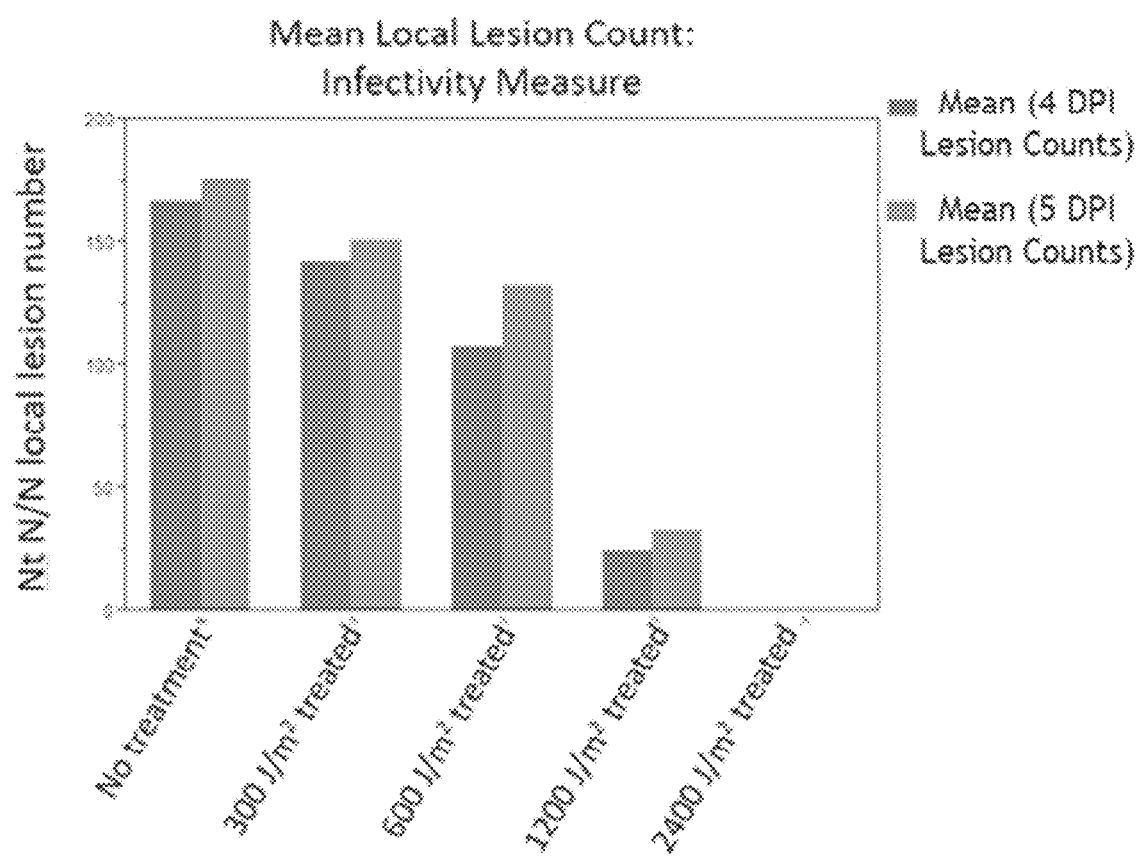
FIG. 21 is a graph illustrating the infectivity of viruses treated with various levels of UV irradiation, according to multiple embodiments and alternatives.

As shown in FIG. 21, various amounts of UV-C irradiation (with energy densities between 300 J/m$^2$ and 2400 J/m$^2$) were tested on *Nicotiana tabacum* plants to evaluate infectivity. As shown in FIG. 21, the lesions were reduced to zero after an UV-C energy dosage of 2400 J/m$^2$, therefore indicating successful inactivation of the virus. In addition, energy dosages at much higher levels were also tested, and it was determined that successful inactivation of TMV NtK also occurred at energy densities ranging between 4800 J/m$^2$ and 5142 J/m$^2$.

According to multiple embodiments and alternatives, the steps of the viral inactivation (following purification but before conjugation) are as follows:

Dilution of the TMV NtK solution to a concentration less than 50 micrograms/ml, as measured by A260 (which is a common method of quantifying nucleic acids by exposing a sample to UV light at a wavelength of 260 nm and measuring the amount of light that passes through the sample).

0.45 micron filtration of the TMV solution to remove bacteria and any other large species that might interfere with UV line of sight.

Inactivating the TMV NtK by exposing the virus to light in the UV spectrum with an energy density between about 2400 J/m$^2$ and about 5142 J/m$^2$. In some embodiments, the energy density of the UV light is between about 4800 J/m$^2$ and about 5142 J/m$^2$. According to multiple embodiments and alternatives, the wavelength of the UV light is 254 nm.

Next, the inactivated TMV NtK is ready to be conjugated to the recombinant antigen.

These viral inactivation steps are designed for commercial scalability and compliance with the cGMP regulations

EXAMPLE 9 pH Dependency of Conjugation

To evaluate whether incubating the virus at an acidic pH results in high quality conjugation, an experiment was performed using the same batches of virus, antigen, buffers, and esters, but changing only the formulation of the virus. In reaction 1, TMV was formulated into 1× MES Conjugation Buffer at pH 5.50 at a concentration of 3.1 mg/ml, according to multiple embodiments and alternatives. In reaction 2, TMV was concentrated to 11.0 mg/ml in phosphate buffer and added directly as 15% of the conjugation reaction volume. After these steps, the conjugation process was monitoring by SEC wherein an ordered decrease in free TMV from zero minutes (indicated by T=0) would indicate successful conjugation.

As shown in Tables 7 and 8, reaction 1 exhibited successful conjugation (due to the ordered decrease in free TMV from zero minutes) while reaction 2 was unsuccessful as shown by the percent remaining free TMV.

TABLE 7

Reaction 1, Successful Conjugation - TMV Formulated in Acidic pH

| Sample | Reaction 1 (TMV Formulated in MES at 3.1 mg/mL) | Free TMV Peak Area by SEC | Remaining % Free TMV |
|---|---|---|---|
| Free NtK | 284.8 nm | 11104 | N/A |
| T = 0 | 154.9 nm | 9732 | 100% |
| T = 5' | 139.8 nm | 3909 | 40% |
| T = 15' | 142.8 nm | 1815 | 19% |
| T = 30' | 149.4 nm | 1039 | 11% |
| T = 45' | 155.6 nm | 769 | 8% |
| T = 60' | 153.2 nm | 777 | 8% |

TABLE 8

Reaction 2, Unsuccessful Conjugation - TMV Formulated in Phosphate Buffer

| Sample | Reaction 2 (TMV at 11.0 mg/mL in Phosphate Buffer) | Free TMV Peak Area by SEC | Remaining % Free TMV |
|---|---|---|---|
| Free NtK | 64.2 nm | 27590 | N/A |
| T = 0 | 67.5 nm | 14750 | 100% |
| T = 5' | 68.8 nm | 14916 | 101% |
| T = 15' | 66.9 nm | 13046 | 88% |
| T = 30' | 73.3 nm | 11705 | 79% |
| T = 45' | 75.8 nm | 8109 | 55% |
| T = 60' | 80.0 nm | 11020 | 75% |

Accordingly, as shown in Table 7, incubation of the virus in acidic pH results in a conjugation greater than 90%. If the acidic pH incubation step does not occur, then the percent conjugation remains less than 50% (as shown in Table 8).

Figure 22:
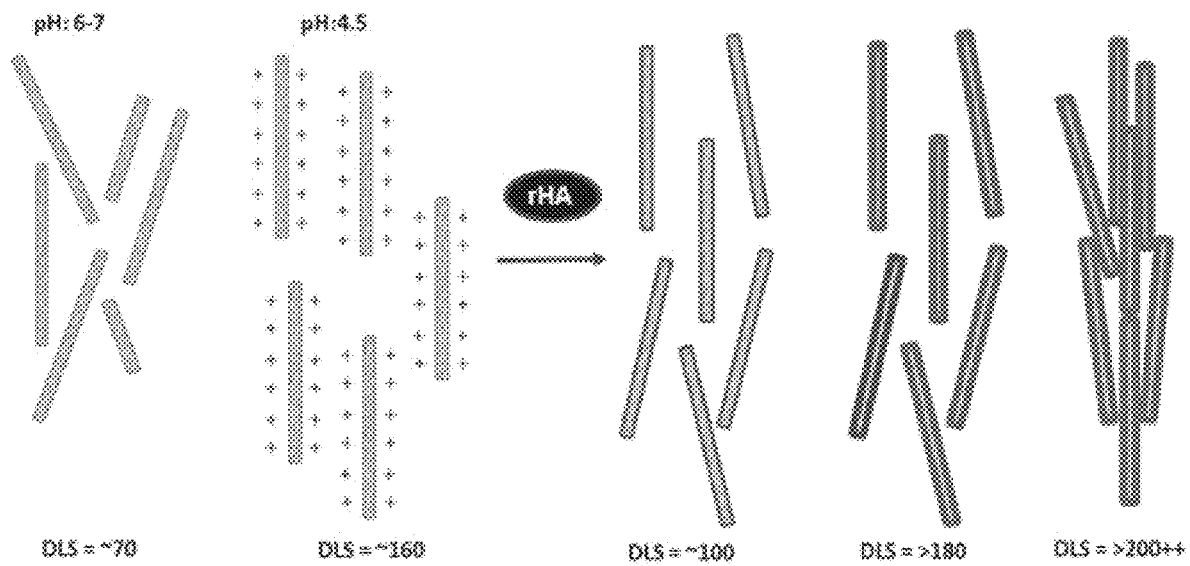
FIG. 22 is an illustration of some of the steps of the conjugation platform of recombinant antigen to a virus, according to multiple embodiments and alternatives.

Based on this experiment, a model for conjugation (shown in FIG. 22) was developed. According to multiple embodiments and alternatives, conjugation between purified virus and purified antigen (denoted by "rHA" in FIG. 22) is greatly enhanced by improving the chemical readiness of the virus to engage the antigen (referred to herein as "activating," "activation," or "activates"). In some embodiments, virus activation occurs by formulating the virus in an acidic pH prior to the conjugation reaction such that positive charge aggregates on the virus surface. In some embodiments, the activating step involves exposing the virus to a pH of about 5.5 or less for a period of time sufficient for activation. In some embodiments, such period is between about 18 and 72 hours. According to multiple embodiments and alternatives, processing the purified virus in an acidic pH activates the virus by charging the coat protein lysine. As a result of this activation step, positive charges aggregate on the virus surface (as shown in FIG. 22) via the clustering of the amine groups and the virus is ready for conjugation with the carboxyl end of the recombinant antigen.

The virus activation steps, according to multiple embodiments and alternatives, are in contrast with traditional approaches in which the pH when storing viruses generally is maintained at or near neutral pH. As shown in FIG. 22, the traditional approach does not aggregate positive charge on the virus surface, and as a result the percent conjugation remains below 50% (see Table 8). Furthermore, the conventional approach utilizes phosphate buffers which promote solubility at the expense of having favorable surface charge.

During the investigation of successful conjugations involving TMV, it was observed that successful conjugations generally occurred when the Dynamic Light Scattering (DLS)-measured radius of the virus increased during the activation step by at least a factor of 2.75 (see Table 9A, compared to Table 9B). In general, successful TMV conjugations (such as discussed with Table 9C) were characterized by an increase in DLS radius from about 70 nm to about 195 nm or higher, as shown in these tables.

Based on the successful conjugation which utilized virus activation, a platform was developed for conjugating purified antigen to purified virus. According to multiple embodiments and alternatives, the steps for preparing the purified antigen for conjugation are as follows:

To ensure pH control of the conjugation reaction, the purified antigen is formulated into a reaction buffer immediately prior to reaction initiation.

Prior to conjugation, purified antigens are stored in phosphate buffered saline at neutral to slightly basic pH.

The antigen pH target typically is pH 5.50 to 6.50, depending upon the nature of the molecule.

To facilitate conjugation to the virus, the storage buffer is replaced with a MES/NaCl buffer at acidic pH using ultrafiltration. The protein concentration is also increased to greater than 3 mg/mL.

The conjugation reaction is then initiated within four hours of antigen preparation completion to prevent destabilizing the protein structure.

According to multiple embodiments and alternatives, the steps for preparing the purified virus for conjugation are as follows:

After storage at neutral pH, the virus is activated at acidic pH prior to conjugation. For successful reactions, the virus is formulated from phosphate buffer at pH 7.4 into acetate buffer at pH 5.50 for a minimum of about 18 hours to a maximum of about 72 hours prior to the conjugation reaction start. In some embodiments, the virus is formulated from phosphate buffer at pH 7.4 into acetate buffer at pH 4.50 for a minimum of about 18 hours to a maximum of 72 hours prior to the conjugation reaction start. It was observed that storage of the virus for greater than 72 hours at acidic pH creates self-association between the viruses which causes virus insolubility and inhibits the efficiency of the conjugation.

Tables 9A and 9B further demonstrate the activation step in terms of increasing the radius of the virus (in this case, TMV) as measured by DLS. Specifically, Table 9A provides data for DLS radius increase of TMV after being activated, and before a successful conjugation occurred, with the antigens listed in the right-hand column. The "Factor by which radius increased" divides the TMV radius after activation by the typical TMV radius at neutral pH, which is about 70 nm. Conversely, Table 9B provides data for DLS radius increase of TMV after an activation step was started, in advance of unsuccessful attempts at conjugation, with the antigens listed in the right-hand column. In Tables 9A and 9B, the left column represents the standard radius of TMV rods at neutral pH and under general storage conditions, i.e., before any activation occurs.

TABLE 9A

Free TMV radii as measured by DLS
(Prior to successful conjugation)

| TMV radius at neutral pH | TMV radius after activation (nm) (DLS results) | Factor by which radius increased | Antigen |
|---|---|---|---|
| 70 nm | 195.2 | 2.789 | SG |
| 70 nm | 207.2 | 2.960 | SG |
| 70 nm | 249.1 | 3.559 | SG |
| 70 nm | 249.1 | 3.559 | SG |
| 70 nm | 228.6 | 3.266 | SG |
| 70 nm | 234.1 | 3.344 | SG |
| 70 nm | 234.1 | 3.344 | SG |
| 70 nm | 441.3 | 6.304 | SG |
| 70 nm | 284.8 | 4.069 | SG |
| 70 nm | 517.6 | 7.394 | SG |
| 70 nm | 574.0 | 8.200 | SG |
| 70 nm | 448.2 | 6.403 | SG |
| 70 nm | 209.7 | 2.966 | PH |
| 70 nm | 220.4 | 3.149 | PH |
| 70 nm | 495.6 | 7.080 | PH |
| 70 nm | 517.6 | 7.394 | PH |
| 70 nm | 266.8 | 3.811 | CO |
| 70 nm | 495.6 | 7.080 | CO |
| 70 nm | 517.6 | 7.394 | CO |
| 70 nm | 295.4 | 4.220 | MI |
| 70 nm | 517.6 | 7.394 | MI |
| 70 nm | 574.0 | 8.200 | MI |
| Average (nm): 413.5 | Average Factor for Increase: 5.176 | | |

TABLE 9A

Free TMV radii as measured by DLS
(Prior to unsuccessful conjugation)

| TMV radius at neutral pH (standard) | TMV radius after activation (nm) (DLS results) | Factor by which radius increased | Antigen |
|---|---|---|---|
| 70 nm | 95.4 | 1.363 | SG |
| 70 nm | 105.4 | 1.506 | SG |
| 70 nm | 156.0 | 2.229 | SG |
| 70 nm | 176.5 | 2.521 | PH |
| Average (nm): 133.3 | Average Factor for Increase: 1.905 | | |

Following these preparation steps, the antigen and virus reactants were mixed and the conjugation progress was monitored using DLS and SDS-PAGE methods. Table 9C illustrates the average molecular radius of the conjugation reaction over time using DLS after the virus was activated using acidic pH. As shown in Table 9C, molecular radius is one indicator of successful coating of the viral rods with antigen molecules.

TABLE 9C

TMV NtK SEC and DLS History

| Soluble NTK SEC Peak Area | DLS Radius (nm) |
|---|---|
| 10750 | 496 |
| 9651 | 518 |
| 7106 | 574 |
| 5538 | 660 |

Figure 23:
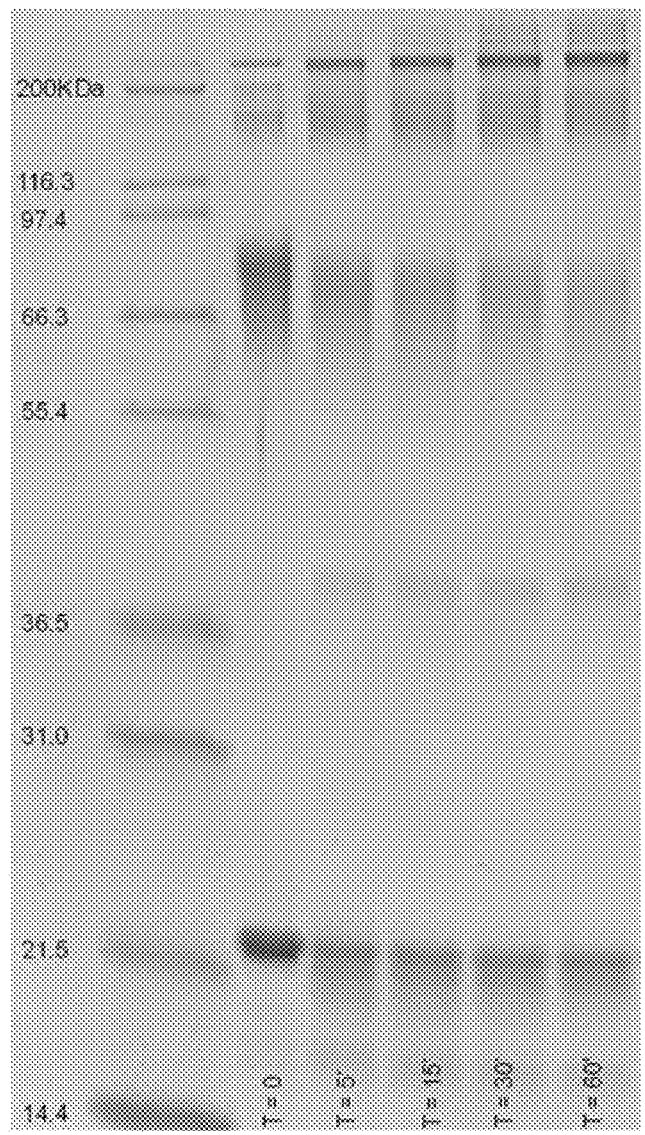
FIG. 23 is a SDS-PAGE analysis of the conjugation of an antigen to a virus, according to multiple embodiments and alternatives.
Figure 24:
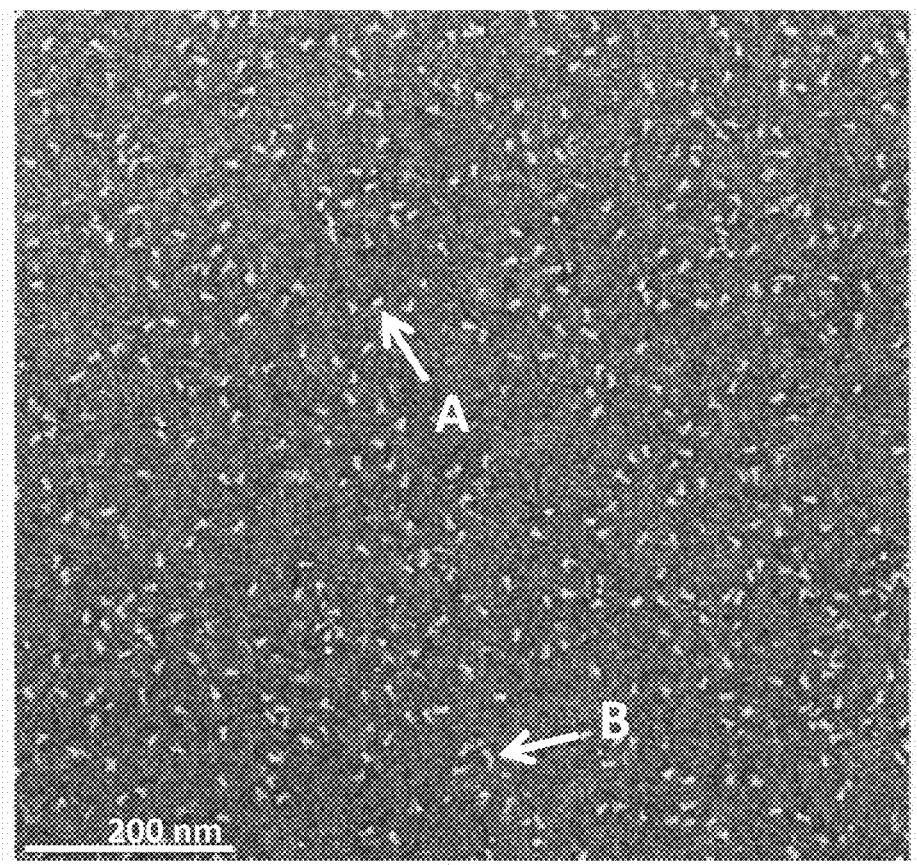
FIG. 24 is a negative stain transmission electron microscopy (TEM) image of recombinant antigen, according to multiple embodiments and alternatives.
Figure 25:
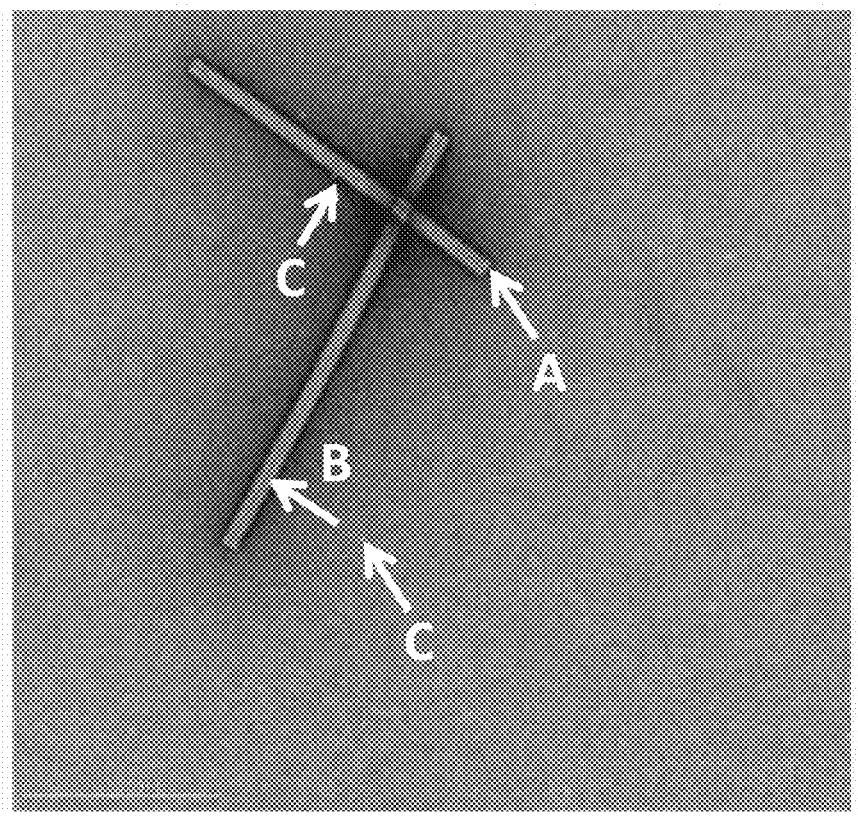
FIG. 25 is a negative stain TEM image of a virus, according to multiple embodiments and alternatives.
Figure 26:
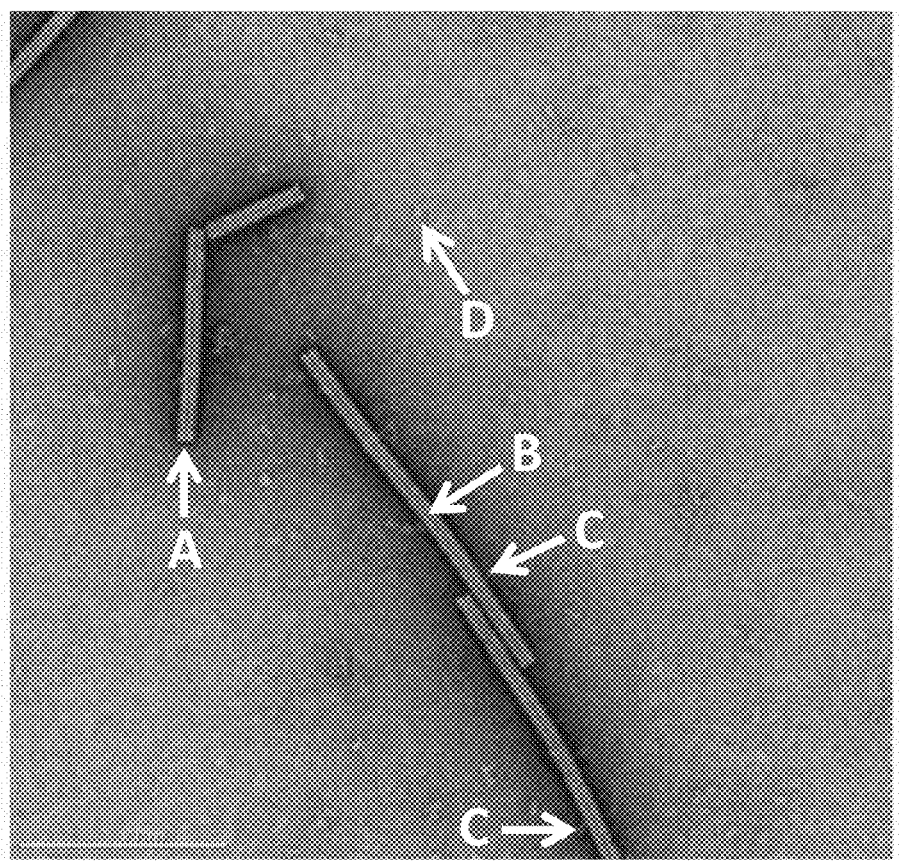
FIG. 26 is a negative stain TEM image of a recombinant antigen conjugated to another recombinant antigen with added virus, according to multiple embodiments and alternatives.
Figure 27:
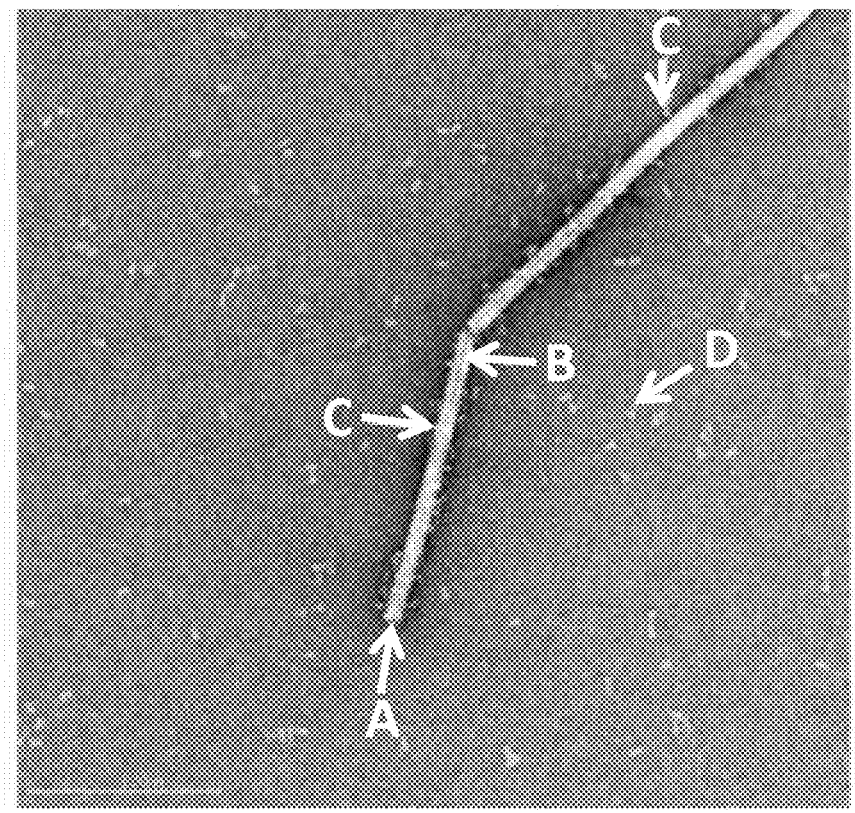
FIG. 27 is a negative stain TEM image of recombinant antigen conjugated to a virus at a virus to recombinant antigen ratio of 1:1, according to multiple embodiments and alternatives.
Figure 28:
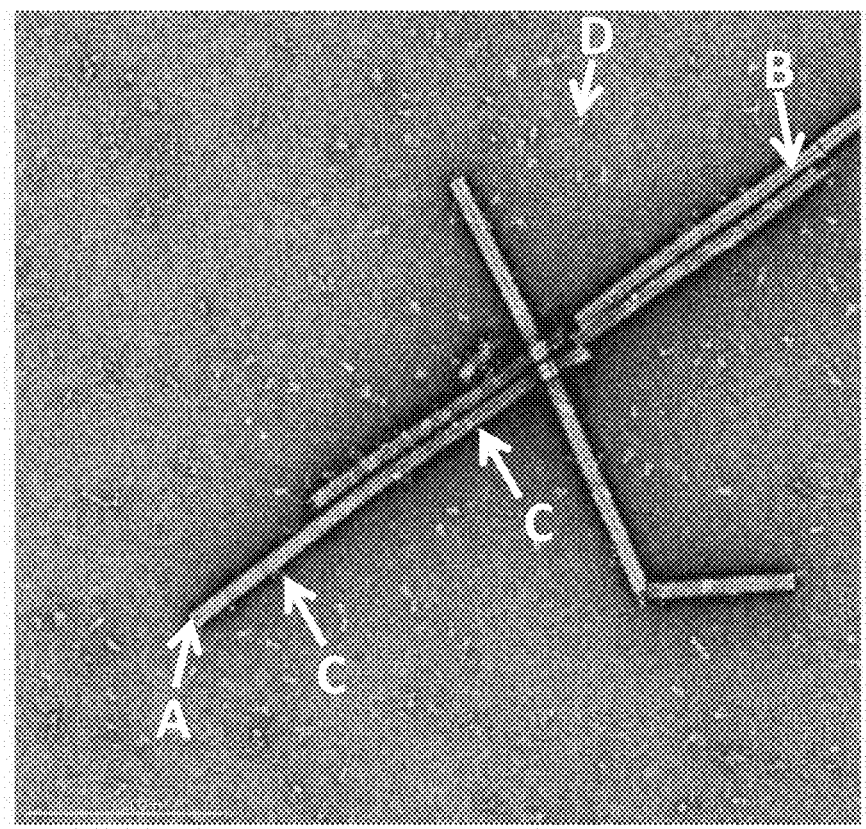
FIG. 28 is a negative stain TEM image of recombinant antigen conjugated to a virus at a virus to recombinant antigen ratio of 1:1, according to multiple embodiments and alternatives.
Figure 29:
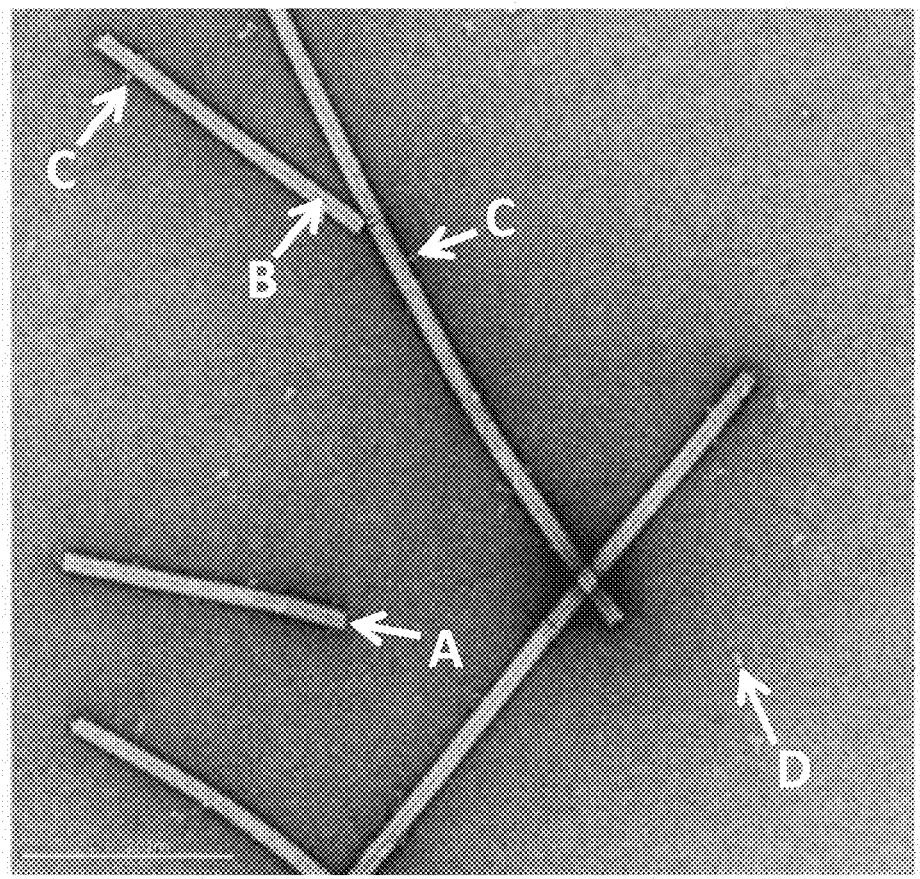
FIG. 29 is a negative stain TEM image of recombinant antigen conjugated to a virus at a virus to recombinant antigen ratio of 4:1, according to multiple embodiments and alternatives.
Figure 30:
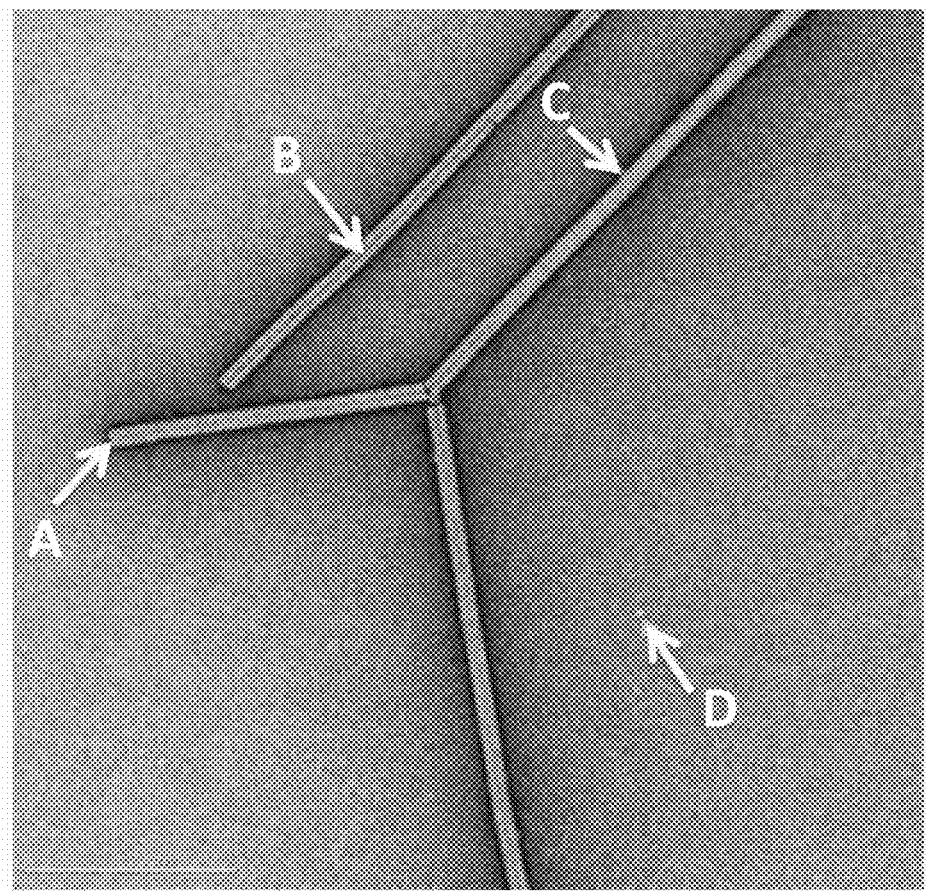
FIG. 30 is a negative stain TEM image of recombinant antigen conjugated to a virus at a virus to recombinant antigen ratio of 16:1, according to multiple embodiments and alternatives.

In turn, FIG. 23 shows an analysis based on the SDS-PAGE of the conjugation between the activated TMV NtK and purified antigen according to multiple embodiments and alternatives. As shown in FIG. 23, the ordered reduction in both free TMV NtK and free antigen over time, coupled with the appearance of protein bands of >200 kDA, indicates successful conjugation.

EXAMPLE 10

TEM Imaging of Different Ratios of Purified Virus to Purified Antigen for Conjugation The desired conjugation reaction between purified virus and purified antigen is represented by the following formula:

$$\text{Virus} + \text{Antigen} \rightarrow \text{Virus-Antigen} \quad \text{(Formula 1)}$$

However, it is well known that antigens are prone to self-conjugation and the desired reaction may not be obtained, as shown by the following formula:

$$\text{Virus} + \text{Antigen} \rightarrow \text{Virus-Antigen} + \text{Antigen-Antigen} \quad \text{(Formula 2)}$$

Self-conjugation of the purified antigen is a problem for the successful development of vaccines because the antigen-antigen conjugates are not removed during the size chromatography step and the result is a minimized or reduced immune response.

To address this self-conjugation problem, various experiments were performed to determine how to consume the unreacted antigens and antigen conjugates. First, the antigens were capped by exposing them to reagents that inhibited self-conjugation. While it was anticipated that this traditional approach would be successful, this approach failed because the reaction occurred too quickly.

Next, the virus to antigen ratios were adjusted to determine suitable conjugation ratios. As shown in Tables 10 and 11 and FIGS. 24-30, seven different samples were analyzed by negative stain transmission electron microscopy (TEM) imaging. Samples 1-3 were control groups and samples 4-7 contained different hemagglutinin (HA) to TMV ratios (at the mixing step of the conjugation platform, as shown at operative step 5 of Table 3).

TABLE 10

TEM Imaging Samples - Control Groups

| Sample | Description | Lot | Apprx. Volume (μl) | Temp. Stored | Concentration |
|---|---|---|---|---|---|
| 1 | HA Alone | 19UL-SG-001 | 100 | 4° C. | 1.01 mg/ml free HA |
| 2 | TMV NtK Alone | 18HA-NTK-001 | 100 | 4° C. | 0.54 mg/ml free TMV NtK |
| 3 | HA:HA Conjugates with added TMV NtK | 19UL-SG-004 | 100 | 4° C. | 2.335 mg/ml |

TABLE 11

TEM Imaging Samples - Conjugates

| Sample | Ratio | Lot | Approx. Volume (μl) | Temp. Stored | Concentration |
|---|---|---|---|---|---|
| 4 | TMV:HA = 1:1 | 18TAP-SG-002 | 100 | 4° C. | 5.2 mg/ml |
| 5 | TMV:HA = 1:1 | 19UL-SG-001 | 100 | 4° C. | 1.688 mg/ml |
| 6 | TMV:HA = 4:1 | 19UL-SG-002 | 100 | 4° C. | 1.387 mg/ml |
| 7 | TMV:HA = 16:1 | 19UL-SG-003 | 100 | 4° C. | 3.479 mg/ml |

FIG. 24 is a TEM image of sample 1 (free HA, lot 19UL-SG-001) at a magnification of 52,000× and a scale bar of 200 nm. In FIG. 24, this sample contained small globular arrows (indicated by arrow A) and elongated particles (indicated by arrow B) that ranged from ~5 nm to ~9 nm in size. The appearance of these particles shows a regular structure consistent with ordered aggregation of HA in keeping with native trimer conformation. In addition, the particles were well dispersed with minimal instances of clumping.

FIG. 25 is a TEM image of sample 2 (TMV NtK alone, lot 18HA-NTK-001) at a magnification of 52,000× and a scale bar of 200 nm. In FIG. 25, rod-shaped particles (arrow A) were observed in sizes ranging from ~125 nm to ~700 nm in length and ~18 nm to ~20.5 nm in width. These dimensions are consistent with the size and shape of TMV particles. In addition, a central ~4 nm channel was observed in the rods (arrow B), which is a known characteristic of TMV. Multiple rods were frequently aligned parallel to their long axis and the surface of the rods were generally smooth. On a few occasions, small ~8 nm to ~10 nm globular particles (arrow C) were observed both associated with the surface of the rods and not associated with the rod-shaped particles in the background. These globular particles (arrow C) did not resemble individual HA trimers.

FIG. 26 is a TEM image of sample 3 (HA:HA Self-Conjugates with added TMV NtK, lot 19UL-SG-004) at a magnification of 52,000× and a scale bar of 200 nm. In FIG. 26, rod-shaped particles were observed that ranged from ~25 nm to ~885 nm in length to ~18 nm to ~20.5 nm in width (arrow A) and a central ~4 nm inner channel (arrow B). The rods were either not decorated at all or sparsely decorated with small, proteinaceous particles of various sizes and shapes (arrow C). Some of the small, proteinaceous particles were also seen in the background, not associated with the rods (arrow D). FIG. 26 illustrates larger clumps of HA particles, but the TMV looks identical to the unconjugated TMV (shown in FIG. 25) as expected.

FIG. 27 is a TEM image of sample 4 (TMV:HA in a 1:1 ratio, lot 18TAP-SG-002) at a magnification of 52,000× and a scale bar of 200 nm. In FIG. 27, rod-shaped particles were observed that ranged in size from ~50 nm to more than ~1000 nm in length and ~18 nm to ~20.5 nm in width (arrow A) with a ~4 nm central inner channel (arrow B). The particle rods were similar in size and shape to the conjugated TMV observed in FIG. 28, with the exception that the majority of the rods were heavily decorated with small proteinaceous densities on their surface (arrow C). Some of the small, proteinaceous particles were also seen in the background, not associated with the rods (arrow D). The sample 5 shown in FIG. 27 looks superior to the other TEM images which is most likely due to the difference in virus treatment prior to conjugation. For this batch, the virus was formulated at pH 5.50, then the pH was reduced to 4.50 for 15 minutes, and brought back up to pH 5.50 at the start of the conjugation reaction. For the batches shown in FIGS. 28-30, the virus was formulated directly into pH 4.50 and held overnight before the conjugation.

FIG. 28 is a TEM image of sample 5 (TMV:HA in a 1:1 ratio, lot 19UL-SG-001) at a magnification of 52,000× and a scale bar of 200 nm. In FIG. 28, many rod-shaped particles were visible that ranged from ~65 nm to ~720 nm in length and ~18 nm to ~20.5 nm in width (arrow A) with a ~4 nm central inner channel (arrow B). The particle rods were similar in size and shape to the free TMV NtK (sample 2) observed in FIG. 25. However, in contrast to the unconjugated virus shown in FIG. 25, the particle rods observed in FIG. 28 were moderately decorated with proteinaceous densities (arrow C). These densities were irregular in shape and size, and appeared to be randomly associated with the surface of the rods with no obvious pattern. Some of the small, proteinaceous particles were also seen in the background, not associated with the rods (arrow D).

FIG. 29 is a TEM image of sample 6 (TMV:HA in a 4:1 ratio, lot 19UL-SG-002) at a magnification of 52,000× and a scale bar of 200 nm. In FIG. 29, rod-shaped particles were observed that ranged from ~25 nm to more than 1000 nm in length, and ~18 nm to ~20.5 nm in width (arrow A) with a ~4 nm central inner channel (arrow B). The particle rods observed in FIG. 29 were similar in dimension to the previously conjugated samples, but the level of surface decoration of the small proteinaceous densities (arrow C) ranged from moderate to sparse. Some of the small, proteinaceous particles were also seen in the background, not associated with the rods (arrow D).

FIG. 30 is a TEM image of sample 7 (TMV:HA in a 16:1 ratio, lot 19UL-SG-003) at a magnification of 52,000× and a scale bar of 200 nm. In FIG. 30, rod-shaped particles were observed that ranged in size from ~30 nm to more than 1000 nm in length and ~18 nm to ~20.5 nm in width (arrow A) with a ~4 nm central inner channel (arrow B). The particle rods observed in FIG. 30 were similar in overall morphology to the previous conjugated samples. However, the rods were only sparsely decorated with protein (arrow C) or not decorated at all. Only a few small, proteinaceous particles were seen in the background, not associated with the rods (arrow D).

FIGS. 24-30 illustrate that the 1:1 ratio exhibited full rod decoration, the 4:1 ratio exhibited moderate decoration, and the 16:1 ratio exhibited sparse decoration. Stated differently, the 1:1 ratio generated virus rods with heavy antigen decoration (i.e. more density) of HA antigen, while the 16:1 ratio generated viral rods with less antigen decoration (i.e. less density) of HA antigen on each rod. As a byproduct of the conjugation reaction, HA-HA self-conjugates were observed, principally in the 1:1 ratio reactions. Furthermore, compared with the 1:1 reactions, there appeared to be less free HA or HA-HA conjugates in the 4:1 reaction and even less with the 16:1 reaction in TEM images as well as SDS-PAGE reaction analyses (data not shown). In other words, there was higher conjugation efficiency of HA to solely TMV rods overall at the 16:1 ratio, but less density of HA per rod than the 1:1 reaction.

EXAMPLE 11

Sedimentation Velocity Analysis of Different Conjugation Conditions

Sedimentation velocity ("SV"), as measured in an analytical ultracentrifuge ("AUC"), is an ideal method for obtaining information about protein heterogeneity and the state of association of aggregation. Specifically, aggregates or different oligomers can be detected on the basis of different sedimentation coefficients. This method also detects aggregates or other minor components at a level below 1% by weight. Furthermore, SV provides high quality quantitation of the relative amounts of species and provides accurate sedimentation coefficients for any aggregates.

In order to measure the amount of self-conjugated and unreacted HA, as well as the amount of HA occupancy on TMV NtK with different conjugation conditions, the total signal associated with the sedimentation of free antigen, free virus, and various TMV:HA ratios were measured using SV-AUC. The following samples and descriptions are provided in Table 12:

TABLE 12

Samples and Descriptions for SV-AUC

| Sample | Description | Lot | Concentration |
|---|---|---|---|
| 1 | HA Alone | 19S-G-001 | 1.01 mg/ml |
| 2 | TMV Ntk Alone | 18HA-NTK-001 | 0.54 mg/ml |
| 3 | TMV:HA = 1:1 | 19UL-SG-004 | 1.0 mg/ml |
| 4 | TMV:HA = 1:1 | 18TAP-SG-002 | 1.0 mg/ml |
| 5 | TMV:HA = 1:1 | 19UL-SG-001 | 0.8 mg/ml |
| 6 | TMV:HA = 4:1 | 19UL-SG-002 | 1.0 mg/ml |
| 7 | TMV:HA = 16:1 | 19UL-SG-003 | 1.0 mg/ml |

These stocks were shipped cold (not frozen) and subsequently stored at 2-8° C. until analyzed. 1× PBS from Corning was used for sample dilution and as a reference blank. Sample 1 was diluted 1:1, and samples 2-7 were diluted 1:3 with 1× PBS to create the sedimentation velocity samples. These dilutions were carried out to bring the total absorbance of the sample within the linear range of the absorbance detection system.

Methods—The diluted samples were loaded into cells with 2-channel charcoal-epon centerpieces with 12 mm optical pathlength. 1× PBS was loaded into the reference channel of each cell. The loaded cells were placed into an analytical rotor, loaded into an analytical ultracentrifuge, and brought to 20° C. The rotor was then brought to 3000 rpm and the samples were scanned (at 280 nm) to confirm proper cell loading. For samples 2-7, the rotor was brought to the final run speed of 9,000 rpm. Scans were recorded at this rotor speed as fast as possible (every 3 min) for ~11 hours (250 total scans for each sample). For sample 1 (the free HA), the rotor was brought to 35,000 rpm and scans were recorded every 4 min for 5.3 hours. The data was then analyzed using the c(s) method described in Schuck, P. (2000), "Size-distribution analysis of macromolecules by sedimentation velocity ultracentrifugation and Lamm equation modeling," *Biophys.* 1 78, 1606-1619. Using this method, raw scans were directly fitted to derive the distribution of sedimentation coefficients, while modeling the influence of diffusion on the data to enhance the resolution.

Results and Discussion—The high-resolution sedimentation coefficient distributions for samples 1-7 are shown in FIGS. 31-37. In these figures, the vertical axis provides the concentration and the horizontal axis provides the separation on the basis of sedimentation coefficient. Each distribution has been normalized by setting the total area under the curve to 1.0 (100%) to ensure the area under each peak provides the fraction of that species. Since samples 2-7 contain material sedimenting over a broad range of sedimentation coefficients, the data analysis has been pushed to cover species sedimenting as fast as 2000 Svedburg units (S), and therefore the horizontal axis is on a log scale. To compensate for the effect that log scaling could distort the visible area of the peaks, the vertical axis has been multiplied by the sedimentation coefficient, which correctly scales the relative peak areas. The data for sample 1 (free HA) is presented traditionally using a linear sedimentation coefficient scale.

FIG. 31 is normalized sedimentation coefficient distribution for sample 1 (HA alone, lot 19S-G-001). Since free antigen is much smaller in size than virus, this sample was analyzed at a much faster rotor speed (35,000 rpm) than samples 2-7 (9,000 RPM) in order to adequately characterize the size distribution. As shown in FIG. 31, sample 1 is somewhat homogeneous, providing 73.7% main peak at 8.967 S. This was the expected result for the HA antigen-only sample. This sedimentation coefficient together with the width of the main boundary imply this main peak species has a molar mass of ~222 kDa, which may indicate the main peak corresponds to roughly a HA trimer of the expected ~70 kDa monomer. It is not physically possible for this sedimentation coefficient to correspond to monomer; instead, the main peak corresponds to an oligomeric state larger than monomer. As noted in Table 13 below, SEC HPLC data at HA3 Singapore release, >90% of HA was identified in trimer status, with 3 of the 4 samples analyzed having greater than 50% trimerization.

TABLE 13

Extent of trimerization

| Antigen | Pre-Clinical Lot | HA lot number | SEC Trimer % | SEC Monomer % |
|---|---|---|---|---|
| B/Colorado | 18TAP-CO-001 | 18HA-CO-003 | 55.05% | 44.95% |
| A/Michigan | 18TAP-MH-002 | 18HA-MH-007 | 11.93% | 88.07% |
| B/Phuket | 18TAP-PH-002 | 18HA-PH-003 | 84.51% | 15.49% |
| A/Singapore | 18TAP-SG-002 | 18HA-SG-003 | 94.52% | 3.90% |

As also shown in FIG. 31, seven minor peaks sedimenting faster than the main peak were detected, which together represent 6.2% of the total sedimenting absorbance. Presumably those two peaks represent product aggregates rather than high molecular weight impurities. The principal aggregate species at 12.4 S (4.25%) is sedimenting 1.4 times faster than the monomer, a ratio that falls within the range of 1.4 to 1.5 usually observed for dimers. While that ratio suggests that this species is a dimer of the main peak material (possibly a hexamer of the ~70 kDa monomer), its sedimentation coefficient could also suggest that it is a highly extended or partially-unfolded trimer of the main peak material (possibly a nonamer of the ~70 kDa monomer).

Figure 31:
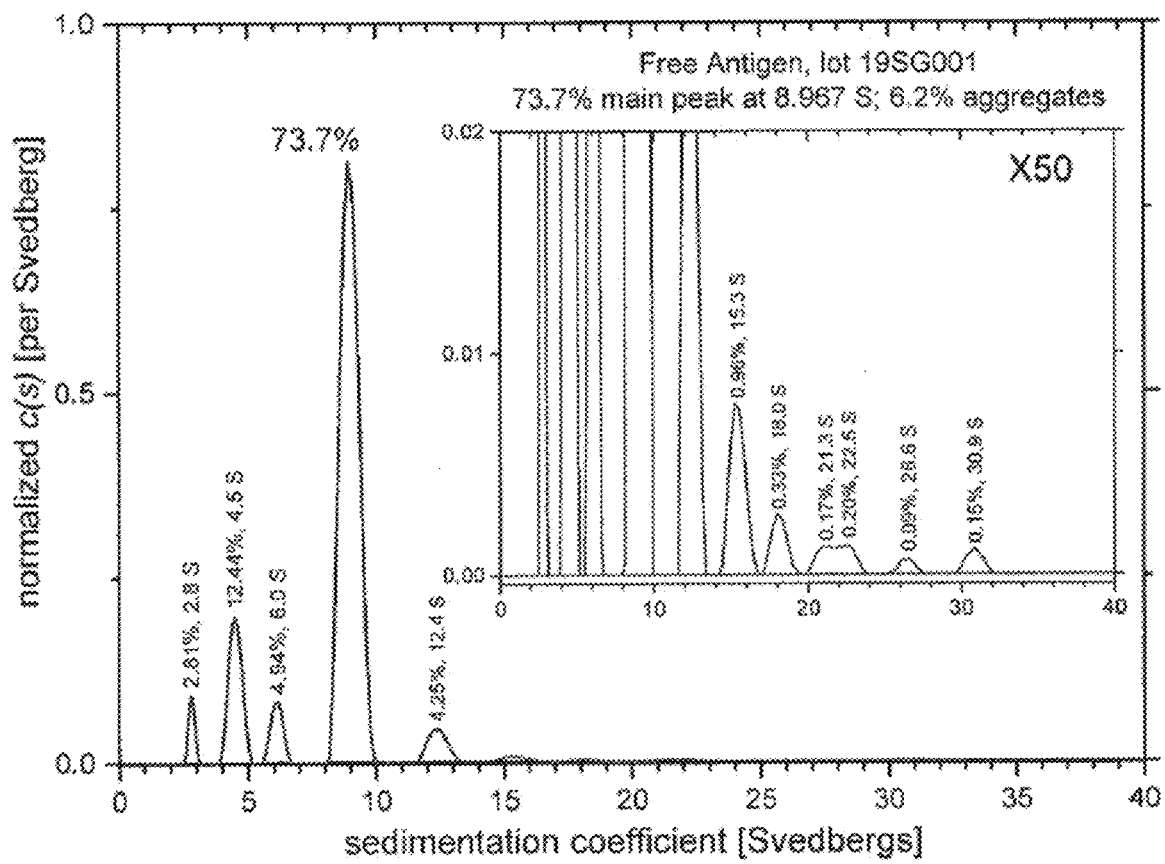
FIG. 31 is a normalized sedimentation coefficient distribution of an antigen, according to multiple embodiments and alternatives.

In FIG. 31, the next peak at 15.3 S (0.96%) is sedimenting 1.7× faster than monomer which suggests a trimer of the main peak material. No absorbance was detected for any sedimentation coefficients larger than 30.9 S. Also, three minor peaks sedimenting more slowly than the main peak were also detected at 2.8 S (2.81%), 4.5 S (12.44%), and 6.0 S (4.94%). Of these minor peaks, the peak at 4.5 S most likely corresponds to antigen monomer.

Figure 32:
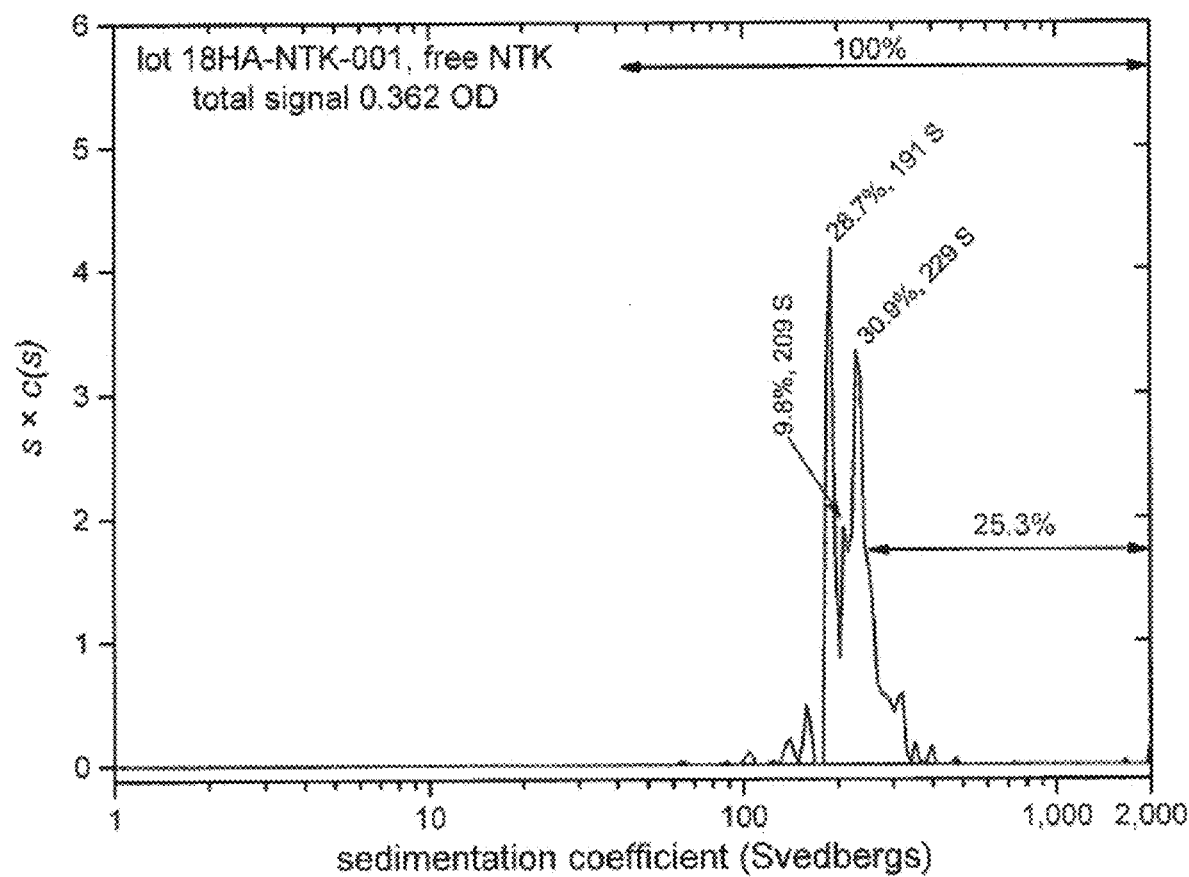
FIG. 32 is a normalized sedimentation coefficient distribution of a virus, according to multiple embodiments and alternatives.

FIG. 32 is the normalized sedimentation coefficient distribution for sample 2 (free TMV NtK, lot 18HA-NTK-001). As shown in FIG. 32, no sedimenting material was detected below ~60 S. This sample appeared quite heterogeneous, with the most abundant peak sedimenting at 229 S (30.9%). The second most abundant peak was detected at 191 S (28.7%). It is not clear which peak corresponds to fully assembled virus. In addition, 25.3% of the total signal was observed sedimenting from 229 S to 2,000 S, the largest sedimentation coefficient allowed in this Example 11. It is unclear what the partially-resolved peaks from ~60 S to 2000 S represent.

FIGS. 33-37 show the normalized sedimentation coefficient distribution for virus-antigen conjugates. Each of these figures shows a significant absorbance of about 0.15 OD that did not sediment. This was established by increasing the rotor speed to 35,000 RPM after the completion of each run, in order to pelletize all remaining material. This material was not observed in either the free antigen or the free TMV NtK samples. However, since this material did not sediment, it did not affect the results of the measured size distributions.

Figure 33:
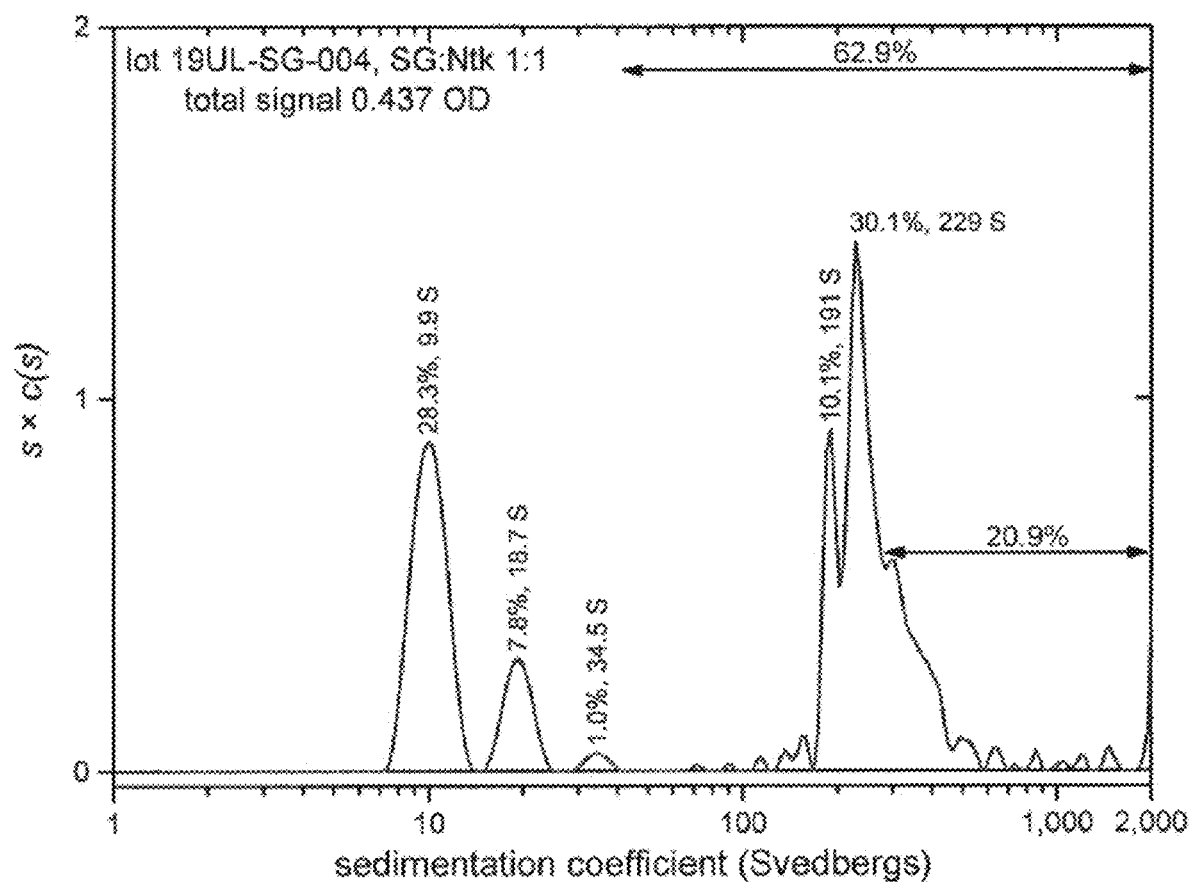
FIG. 33 is a normalized sedimentation coefficient distribution of recombinant antigen conjugated to a virus at a virus to recombinant antigen ratio of 1:1, according to multiple embodiments and alternatives.

FIG. 33 is the normalized sedimentation coefficient distribution for sample 3 (TMV to HA at 1:1 Ratio, lot 19UL-SG-004). As illustrated in FIG. 33, the results in the sedimentation coefficient range from about 40 S to 2000 S, and are similar to those observed for free virus (shown in FIG. 33). Three peaks were also observed in the sedimentation coefficient range of 1-40 S: 9.9 S (28.3%), 18.7 S (7.8%), and 34.5 S (1.0%). The peak observed at 9.9 S may correspond to the main peak observed in the free HA sample (shown in FIG. 32). The variety of smaller peaks may reflect HA-HA self-conjugation events.

Figure 34:
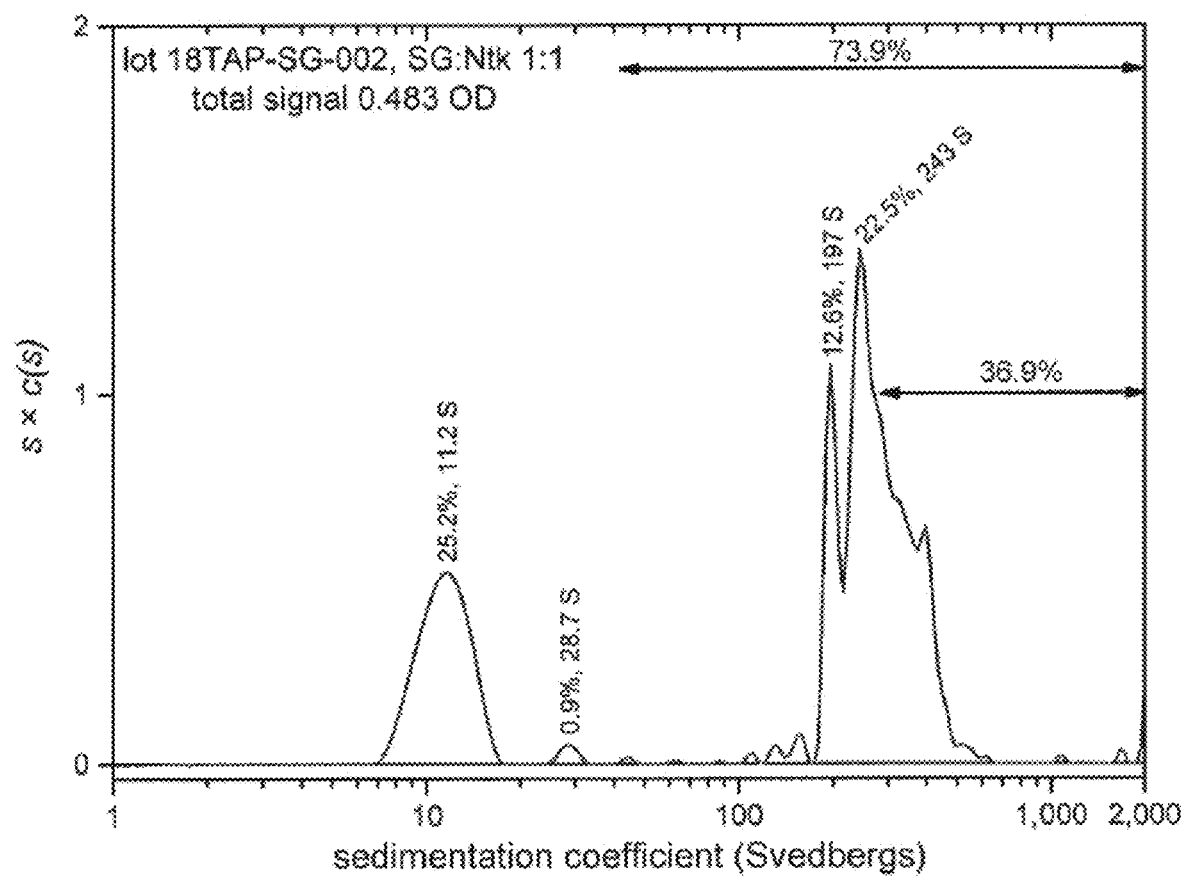
FIG. 34 is a normalized sedimentation coefficient distribution of recombinant antigen conjugated to a virus at a virus to recombinant antigen ratio of 1:1, according to multiple embodiments and alternatives.
Figure 35:
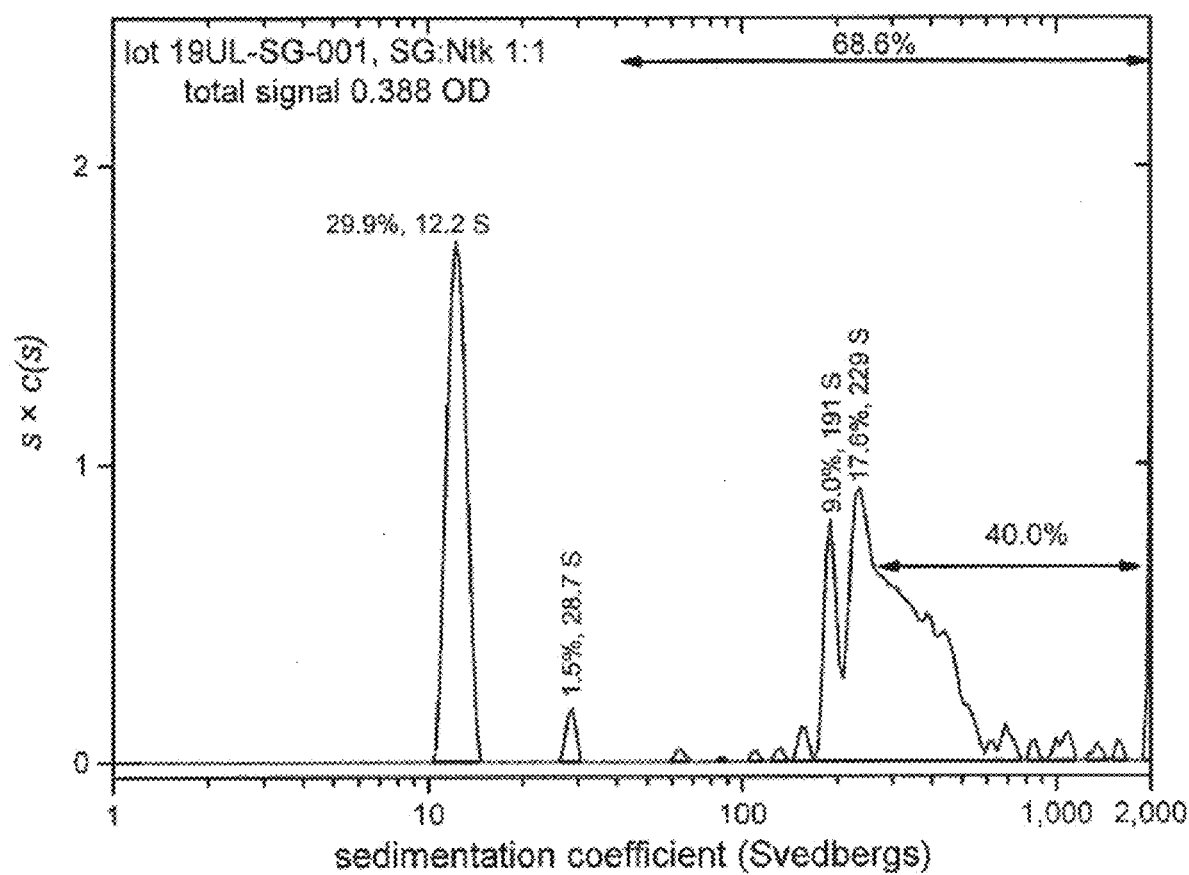
FIG. 35 is a normalized sedimentation coefficient distribution of recombinant antigen conjugated to a virus at a virus to recombinant antigen ratio of 1:1, according to multiple embodiments and alternatives.

FIG. 34 is the normalized sedimentation coefficient distribution for sample 4 (TMV to HA at 1:1 Ratio, lot 18TAP-SG-002) and FIG. 35 is the normalized sedimentation coefficient distribution for sample 5 (TMV to HA at 1:1 Ratio, lot 19UL-SG-001). The results shown in FIGS. 34 and 35 are similar to those discussed for sample 3 (and shown in FIG. 33). However, some notable differences were observed. First, it is difficult to comment on differences observed for the free antigen sample (from 1-40 S) because of poor resolution at this rotor speed. Nevertheless, FIGS. 34 and 35 show more total signal present from 40 S-2,000 S (which is indicative of virus associated material) than sample 3.

Figure 36:
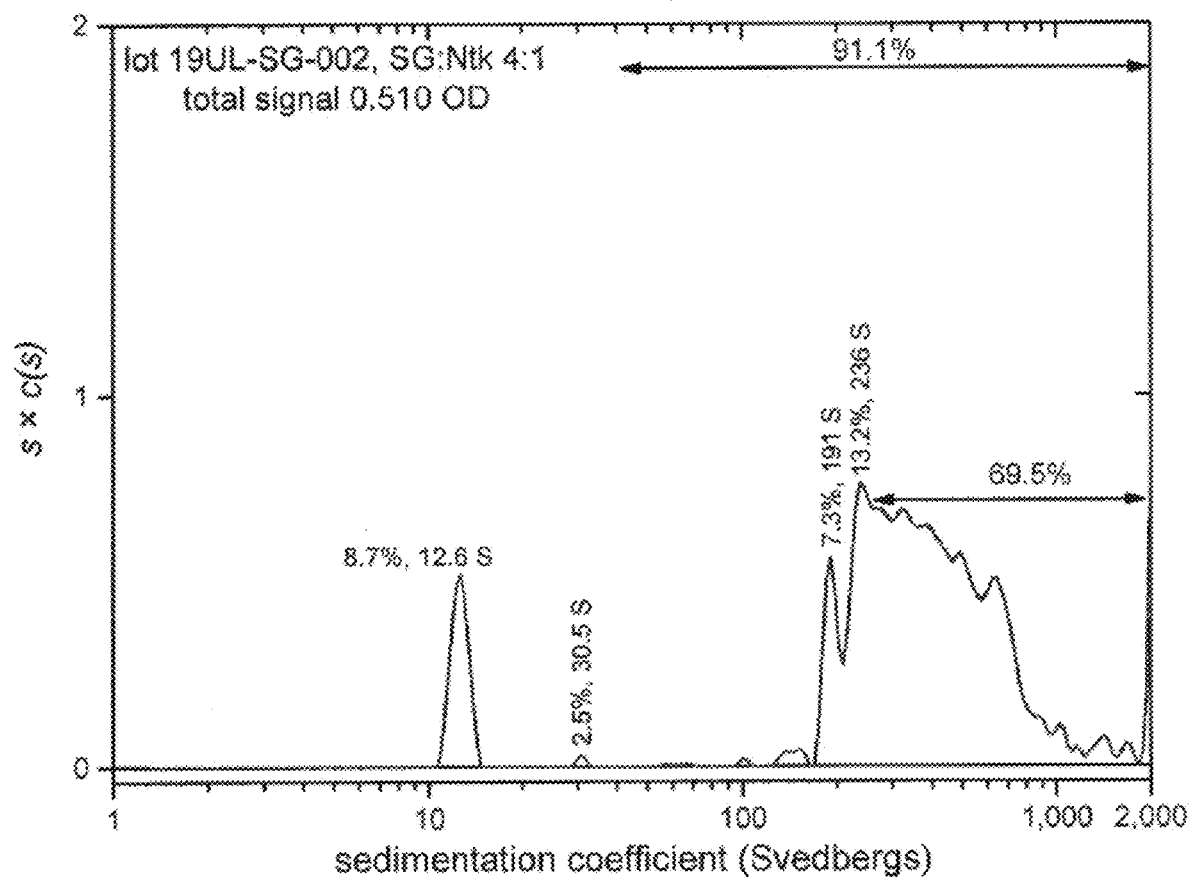
FIG. 36 is a normalized sedimentation coefficient distribution of recombinant antigen conjugated to a virus at a virus to recombinant antigen ratio of 4:1, according to multiple embodiments and alternatives.
Figure 37:
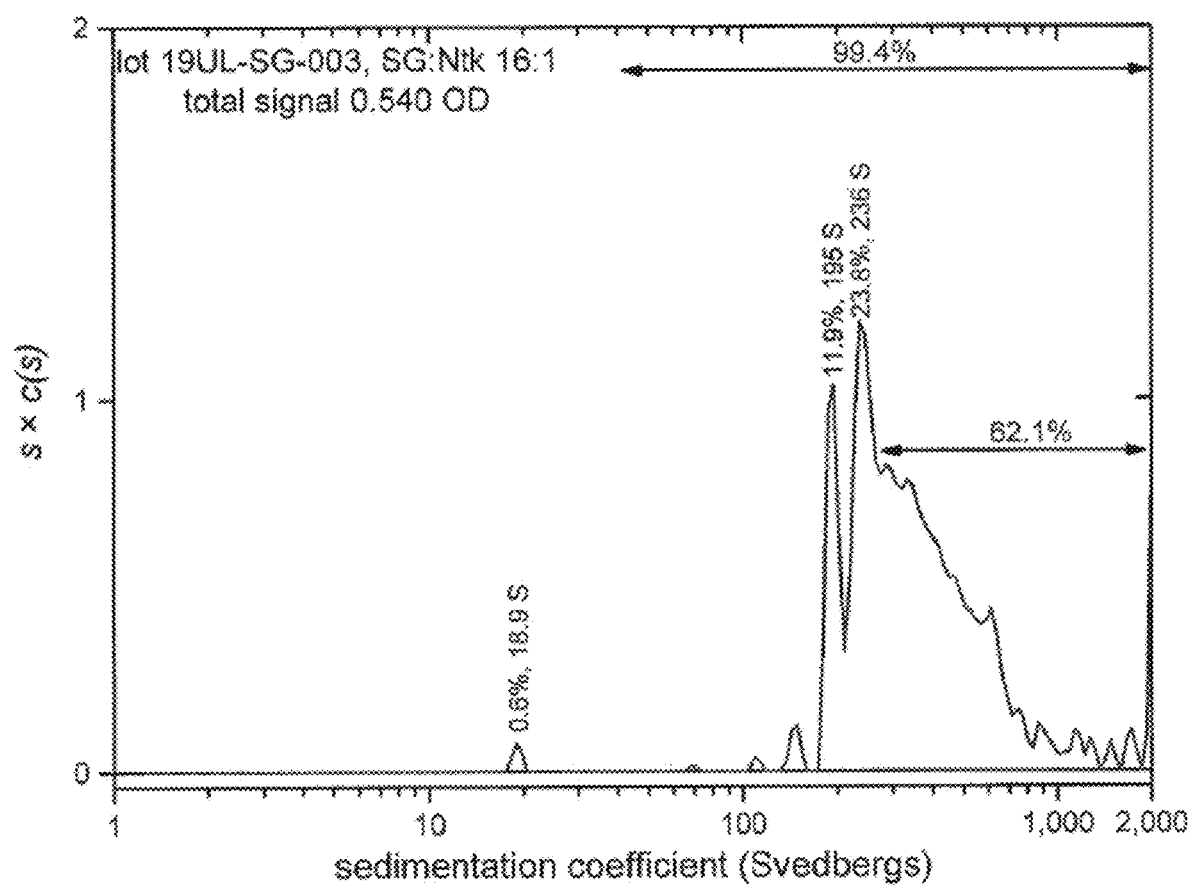
FIG. 37 is a normalized sedimentation coefficient distribution of recombinant antigen conjugated to a virus at a virus to recombinant antigen ratio of 16:1, according to multiple embodiments and alternatives.

FIG. 36 is the normalized sedimentation coefficient distribution for sample 6 (TMV to HA at a 4:1 ratio, lot 19UL-SG-002), and FIG. 37 is the normalized sedimentation coefficient for sample 7 (TMV to HA at a 16:1 ratio, lot 19UL-SG-003). FIG. 36 shows 91.1% total virus-associated material (i.e. virus-antigen conjugates) and FIG. 37 shows 99.4% virus-associated material (i.e. virus-antigen conjugates).

The results for the virus-antigen normalized sedimentation coefficient distribution, as shown in FIGS. 33-37, are set forth in Table 14. As previously noted, the fraction between 1-40 S indicates the percent HA monomer/trimer, and the fraction between 40-2000 S indicates the percent TMV NtK-HA conjugate, according to multiple embodiments and alternatives.

TABLE 14

SV-AUC Results of the Different Virus-Antigen Conjugates

| Sample | Lot | Ratio | Fraction Between 1-40 S (%) (HA monomer/trimer) | Fraction Between 40-2000 S (%) (TMV NtK-HA Conjugate) |
|---|---|---|---|---|
| 3 | 19UL-SG-004 | 1:1 | 37.1 | 62.9 |
| 4 | 18TAP-SG-002 | 1:1 | 26.1 | 73.9 |
| 5 | 19UL-SG-001 | 1:1 | 31.4 | 68.6 |
| 6 | 19UL-SG-002 | 4:1 | 11.2 | 91.1 |
| 7 | 19UL-SG-003 | 16:1 | 0.6 | 99.4 |

The results in Table 14 indicate that a 1:1 ratio has more self-conjugation of HA and HA products, as compared to the 4:1 and 16:1 ratios. In addition, increasing the TMV:HA ratio results in virtually complete engagement of HA products in TMV-conjugation events (approaching almost 100% conjugation in sample 7).

According to multiple embodiments and alternatives, decreasing the amount of HA in a conjugation reaction, by increasing the TMV NtK to HA ratio from 1:1 to 16:1, results in: (1) reducing the aggregation of HA antigen on each TMV rod, as observed by Example 10 and FIGS. 24-30; (2) decreasing the amount of self-conjugation and unreacted HA events to nearly zero, as shown by FIGS. 31-37 and Table 14; and (3) increasing the association of HA (as a percentage) to TMV compared with self-conjugation and unreacted HA events, as shown by FIGS. 31-37 and Table 14.

EXAMPLE 12

Immune Response in Mice

To determine immune response following administration of the inventive virus-antigen conjugates, mice were administered the conjugates as vaccines via intramuscular injection. Each vaccine was a TMV:HA conjugate produced at a 1:1 (TMV:HA) ratio as described herein, administered to most of the animals on Day 0 and 14 of the study (control animals were administered buffer alone, TMV alone, or HA alone). Those administered vaccine received either 15, 7.5, or 3.75 mcg (micrograms) of antigen, as shown below in Table 15. One cohort had samples drawn on Day 7, another at Days 14 and 21, and a third at Days 28, 42, and 90, with the samples then subjected to hemagglutination inhibition (HAI) assay.

Based on the assay, no measurable response from any animal for any vaccine occurred at Days 7 or 14. However, initial responses were seen in some animals on Day 21. Specifically, 10/27 animals showed low level responses (only 1 of them >80 HAI titers) for H1N1 vaccine (Influenza A/Michigan/45/2015 (H1N1pdm09)). Also, 22/27 showed low level responses (only 2 of them >80) for H3N2 vaccine (Influenza A/Singapore/INFIMH-16-0019/2016). On Day 28, the number of animals within this cohort responding measurably to H1N1 vaccine was 8/29 with a single animal at 80 HAI titers and all others less. For H3N2 vaccine, the number responding measurably was 14/29, also with a single animal at 80 HAI titers and all others less.

The most pronounced results were observed from blood samples taken at Day 42 and Day 90, which are presented in Table 15, below. In this table, a standard error of the mean (SEM) is provided with the average and the fraction of animals responding (Fr. Resp.). It will be noted that in each cohort, some of the mice received vaccines for Influenza B viruses (B/Colorado/06/2017 (V) and B/Phuket/3073/2013 (Y), respectively). No response was detected in these animals on any of the days, as expected because B-type influenza viruses and corresponding HA immunogens are known to not generate HAI titers in mice with the efficiency and effectiveness as A-type HA immunogens.

TABLE 16

TMV:HA ratio study - A-type influenza HA.

| Grouping | Vaccine | Conjugation ratio (TMV:Antigen) | Average ELISA Ab Titer |
|---|---|---|---|
| 1. | Phosphate-buffered saline | n/a | 0 |
| 2. | TMV-H3 | H3 HA:HA | 0 |
| 3. | TMV-H3 | 1:1 | 0 |
| 4. | TMV-H3 | 4:1 | 120 |
| 5. | TMV-H3 | 16:1 | 200 |

Figure 38:
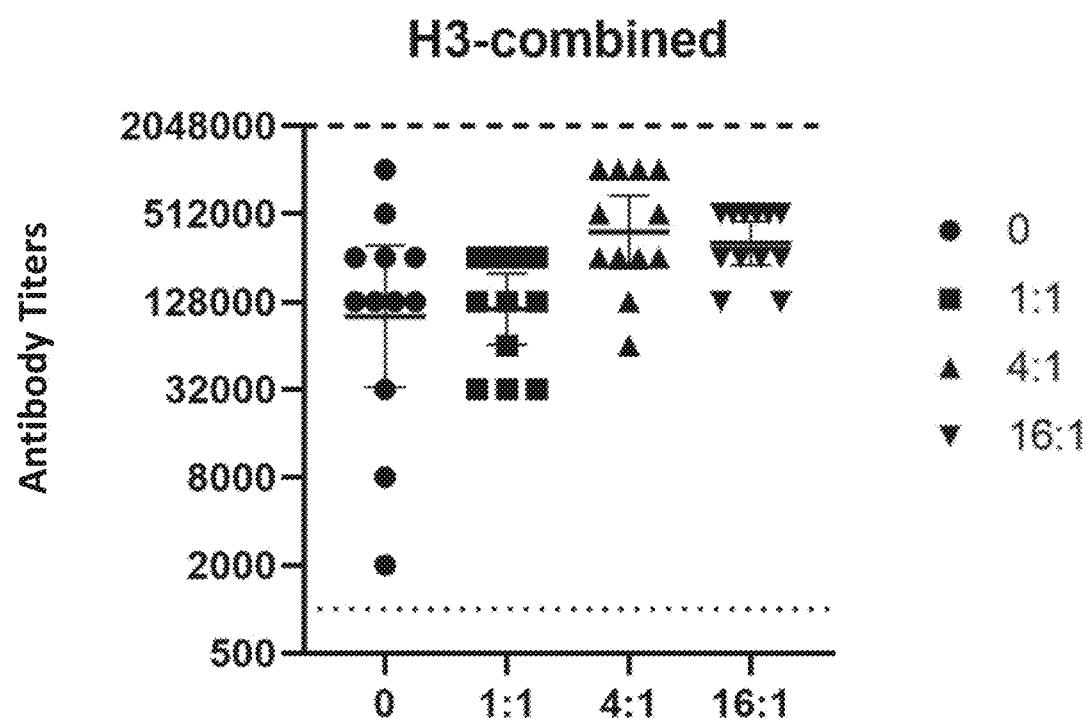
FIG. 38 is a scatterplot of antigen-relevant titers in a source organism following administration of virus-antigen products at various virus to recombinant ratios, according to multiple embodiments and alternatives.
Figure 39:
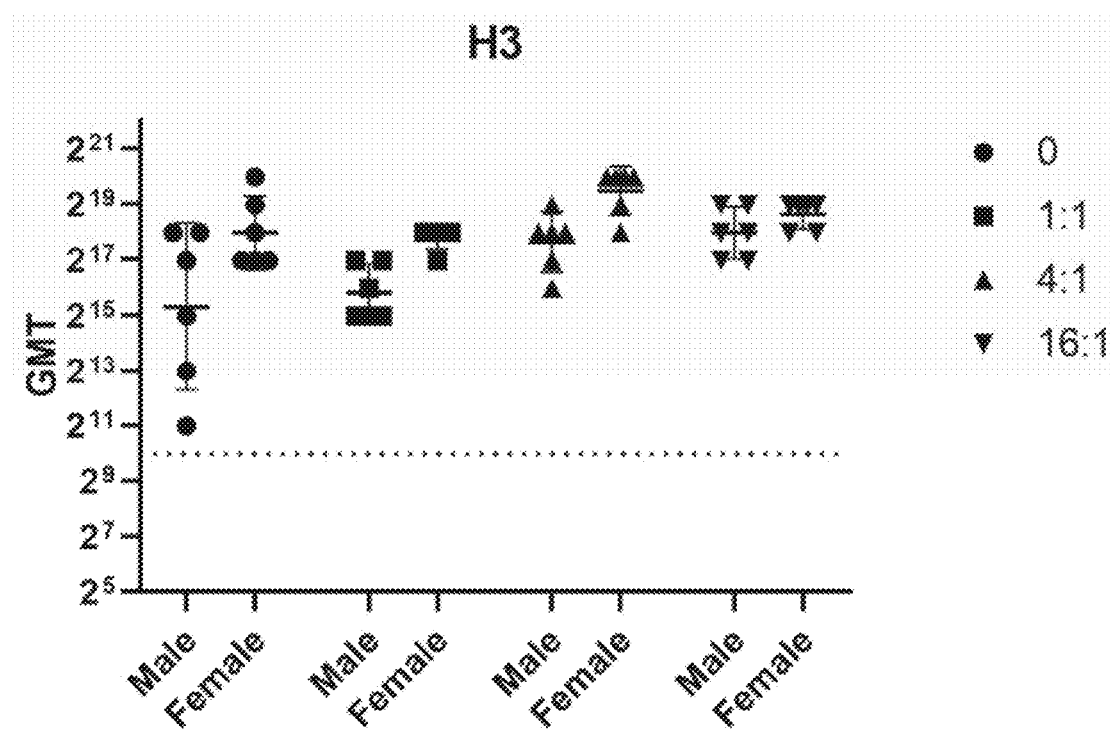
FIG. 39 is a geometric mean testing illustrating the antigen-relevant titers in a source organism following administration of virus-antigen products at various virus to recombinant ratios, according to multiple embodiments and alternatives.

FIG. 38 is a scatterplot associated with Table 16, which provides graphical analysis of H3:HA Ab titers following administration of vaccine at ratios of 0, 1:1, 4:1, and 16:1 (TMV:HA). FIG. 39 also illustrates graphically the results of geometric mean testing of antigen-relevant Ab titers, using recombinant H3 antigen (Table 17) as coating or capture H3 virus as capture protein (Table 17) that binds with anti Influenza A H3 Antigen antibody. In terms of density (surface area of TMV occupied by HA), the trend for the three ratios progresses from 1:1 (most dense) >4:1>16:1 (least dense), as demonstrated by TEM and AUC analyses. In these figures representing ELISA results obtained with H3 antigen, the highest immune response was observed with the least dense conjugate. That is, the trend for immune response

TABLE 15

Immune response based on dose and time post-vaccination

| | Day 42 Average HAI Titers | | | | Day 90 Average HAI Titers | | | |
|---|---|---|---|---|---|---|---|---|
| Immunogen | H1N1 | Fr. Resp | H3N2 | Fr. Resp | H1N1 | Fr. Resp | H3N2 | Fr. Resp |
| 1. Vehicle alone | 0 | 0 | 0 | 0 | 0 | 0 | 0 | 0 |
| 2. TMV alone: 15 mcg | 0 | 0 | 0 | 0 | 0 | 0 | 0 | 0 |
| 3. HA Quad 15 mcg | 0 | 0 | 0 | 0 | 0 | 0 | 0 | 0 |
| 4. HA Quad 7.5 mcg | 0 | 0 | 0 | 0 | 0 | 0 | 0 | 0 |
| 5. HA Quad 3.75 mcg | 0 | 0 | 0 | 0 | 0 | 0 | 0 | 0 |
| 6. V-HA Quad 15 mcg | 20 ± 5.477 | 7/10 | 27 ± 7.218 | 8/10 | 274 ± 66.336 | 10/10 | 136 ± 33.442 | 10/10 |
| 7. V-HA Quad 7.5 mcg | 26 ± 4.733 | 9/10 | 22 ± 9.466 | 6/10 | 174 ± 40.797 | 9/10 | 84 ± 45.77 | 6/10 |
| 8. V-HA Quad 3.75 mcg | 19 ± 4.566 | 7/9 | 17 ± 4.969 | 6/9 | 224 ± 62.993 | 8/9 | 40 ± 10.423 | 7/9 |

Separate from the previously described immune response study, and to further evaluate the inventive system in terms of suitable virus to antigen ratios, the humoral immune response in mice was evaluated following vaccination at various TMV:HA conjugate ratios (i.e., 1:1, 4:1, 16:1) of both Influenza A Antigen and Influenza B Antigen along with controls as noted below. In this manner, various conjugation ratios and their effect on immune response were studied. The mice receiving vaccination were administered 15 mcg HA via injection on Day 0 and Day 14 of the study, in a subcutaneous region dorsally The serum antibody responses to the vaccination were then analyzed for HA-specific activity. Tables 15 (H3 influenza virus used as capture protein) and 16 (recombinant H3 protein used as capture protein) show the groupings of mice (12 mice per grouping), and the agents that were administered, with the right-hand column in each table presenting ELISA antibody (Ab) titers results.

was 16:1>4:1>1:1 and went in reverse of the trend for density. Thus, surprisingly it was found at these ratios for TMV:HA, lesser density of conjugation tended to provide better immune response. Possible explanations for this surprising finding that antigenicity does not correlate with maximum HA conjugation events include: (1) more uniform antigen with less to no-unreacted or self-conjugated protein when the density is comparatively lower; (2) there could be more efficient processing of conjugated antigen and more preserved/uniform antigen conformation; and (3) the TMV rods (by way of example) may stimulate more antigen presenting cells to migrate to the injection site and stimulate processing of attached antigen, or some combination of these factors. Note, however, that just the presence of TMV particles does not replace the need for conjugation (see, e.g., Tables 14 and 15).

In addition to Influenza A H3 Antigen, Influenza B Antigen also was studied (B-Phuket HA) using the binding propensity of recombinant Influenza B Phuket Antigen and its corresponding antibody. Table 17, below, presents the results of this part of the study that was there is not as clear of a showing of 16:1>4:1>1:1 based on the results of average ELISA Ab titers.

TABLE 17

TMV:HA ratio study - B-type influenza HA.

| Grouping | Vaccine | Conjugation ratio (TMV:Antigen) | Average ELISA Ab Titer |
|---|---|---|---|
| 1. | Phosphate-buffered saline | n/a | 0 |
| 2. | TMV-B | B Phuket HA:HA | 283± |
| 3. | TMV-B | 1:1 | 211± |
| 4. | TMV-B | 4:1 | 56± |
| 5. | TMV-B | 16:1 | 329± |

Even so, the 16:1 ratio demonstrated the highest average antibody titer. Thus, the inventors believe it is reasonable to predict the same relationship between density and immune response applies to the study of the Influenza B Antigen (B-Phuket HA). That is, as with the results of H3 antigen, immune response will be higher for less dense forms of the conjugates. Additionally, there is reason to believe the conjugation reaction for the 4:1 ratio did not proceed as the reactions for the other ratios because of possible abnormalities during conjugation, and the fact that neither electron microscopy nor ultracentrifugation analysis were performed on this sample. In any case, the data here show immune response at all three ratios. The fact that immune response was achieved at multiple ratios underscores the robustness of the system for not being tied to any one particular ratio. This flexibility as seen with the particular TMV-conjugated vaccines probably gives further indication that the system will work well both when other antigens are conjugated to TMV besides the H3 and H1 antigens included in these studies, as well as when other virus carriers besides TMV are used for the carrier.

In terms of clinical utility, a product conjugated in accordance with any of multiple embodiments and alternatives described herein may be utilized as a vaccine by delivering the purified antigen via a purified virus, such as but not limited to the virus-antigen conjugates described in Examples 7, 9, 10, 11, and 12. Still further, embodiments of the present disclosure include any vaccine products packaged in any number of forms (e.g., vial) with appropriate buffers and additives, being manufactured from any virus-protein conjugate compositions, the conjugation of which is provided for herein. In this respect, embodiments include those wherein such vaccine products are amenable to delivery in the form of unit doses provided to a human or animal patient, such as but not limited to administration by syringe or spray through routes that include, but are not limited to, subcutaneous, intramuscular, intradermal administration, and nasal, as well as administration orally by mouth and/or topically, to the extent clinically indicated. By way of non-limiting example, and without detracting from the breadth and scope of the embodiments herein, the size of TMV (typically 18 nm×300 nm) and its rod-like shape promotes antigen uptake by antigen presenting cells (APCs), and thus serves to enhance immunity of T cells (such as Th1 and Th2) and provides adjuvant activity to surface conjugated subunit proteins. This activity is also stimulated through viral RNA/TLR7 interaction. As a result, the combined effect of vaccine uptake directly stimulates activation of the APCs. Humoral immunity is typically balanced between IgG1 and IgG2 subclasses through subcutaneous and intranasal delivery. Upon mucosal vaccine delivery, responses also include substantial systemic and mucosal IgA. Cellular immunity is also very robust, inducing antigen-specific secretion, similar to a live virus infection response. Whole antigen fusions allow for native cytotoxic T lymphocyte (CTL) epitope processing, without concern for human leukocyte antigen (HLA) variance.

The broad (humoral and cellular) and augmented (amplitude and effectiveness) immune responses associated with the multi-set purification platform according to current embodiments are in sharp contrast to subunit proteins tested without TMV conjugation, which induce little or no cellular or humoral immunity. The impact of these immune responses is that vaccines created via the multi-set platform, according to current embodiments, promotes highly protective responses as single dose vaccines and offers speed and safety not offered by other conventional vaccine platforms. Indeed, the conjugation platform is shown to work on a wide array of viruses and proteins (including antigens), combined within a broad range of ratios and successfully administered at various doses, which again are indicative of the robustness of the system. Additional advantages of the multi-set platform for producing vaccines in current embodiments include: a proactive antigen-stimulating approach for systemic immune protection against pathogen challenge, the platform is highly adaptable to produce antigenic domains from disease pathogens (including virus glycoproteins or non-secreted pathogen antigens), and the platform serves as an efficacious vaccine platform for both virus and bacterial pathogens.

In addition to advantages regarding vaccine applications, plant virus particles purified via the multi-set platform according to current embodiments can be formulated for various drug delivery purposes. These different purposes may include: 1) immune therapy—through the conjugation of therapeutic antibodies to the surface of virus particles and their delivery to enhance cytotoxic effect; 2) gene therapy—through loading specific nucleic acids for introduction into particular cell types for genetic modification, and 3) drug delivery—through loading chemotherapeutic agents into virus particles for targeted tumor delivery.

As a brief example of the many advantages of the methods discussed herein, the multi-set platform according to multiple embodiments could be utilized as a drug delivery tool by first causing the purified virus to swell by exposing it to a pH shift as discussed above. Subsequently, the virus in this condition would be incubated with a solution of concentrated chemotherapeutic agent, such as doxorubicin, and the pH is then reverted to neutral thereby causing the virus to return to its pre-swollen state and thereby entrapping the chemotherapeutic molecules. Next, the virus particle could be delivered to an organism by a delivery mechanism chosen from a group that includes, but is not necessarily limited to, injection for targeted treatment of tumors.

Accordingly, the above descriptions offer multiple embodiments and a number of alternative approaches for (i) the plant-based manufacture and purification of viruses; (ii) the plant-based manufacture and purification of antigens; and (iii) the formation of virus-antigen conjugates outside the plant that are therapeutically beneficial as vaccines and antigen carriers; and (iv) the delivery of therapeutic vaccines comprising a purified virus and purified antigen.

It will be understood that the embodiments described herein are not limited in their application to the details of the teachings and descriptions set forth, or as illustrated in the accompanying figures. Rather, it will be understood that the present embodiments and alternatives, as described and claimed herein, are capable of being practiced or carried out in various ways. Also, it is to be understood that words and phrases used herein are for the purpose of description and should not be regarded as limiting. The use herein of "including," "comprising," "e.g.," "containing," or "having" and variations of those words is meant to encompass the items listed thereafter, and equivalents of those, as well as additional items.

Accordingly, the foregoing descriptions of several embodiments and alternatives are meant to illustrate, rather than to serve as limits on the scope of what has been disclosed herein. The descriptions herein are not intended to be exhaustive, nor are they meant to limit the understanding of the embodiments to the precise forms disclosed. It will be understood by those having ordinary skill in the art that modifications and variations of these embodiments are reasonably possible in light of the above teachings and descriptions.

What is claimed is:

1. A method for purifying at least one antigen harvested from a source organism, comprising:
   extracting cellular debris from the at least one antigen by adding an extraction buffer to an extract at a ratio of the extraction buffer and the extract expressed as extraction buffer:extract by wt;
   after the extracting step, concentrating the at least one antigen by passing the at least one antigen through a tangential flow filtration apparatus; and
   performing separations comprising sub-steps of separating host cell contaminants from the at least one antigen, subjecting the at least one antigen to affinity chromatography to elute the at least one antigen, and after the separating host cell contaminants and affinity chromatograph sub-steps, subjecting the at least one antigen to multi-modal chromatography to separate residual impurities from the at least one antigen.

2. The method of claim 1, wherein the source organism is a plant.

3. The method of claim 2, further comprising harvesting the at least one antigen from the plant.

4. The method of clam 1, further comprising harvesting the at least one antigen from the source organism, wherein the source organism is selected from the group consisting of bacterial, algal, yeast, insect, and mammalian organisms.

5. The method of claim 1, wherein extracting cellular debris from the at least one antigen comprises passing the at least one antigen through a membranous filtration device comprising a porous membrane.

6. The method of claim 5, wherein the method further comprises maintaining a feed pressure of less than thirty pounds per square inch across the porous membrane.

7. The method of claim 1, wherein said ratio is in a range between 1:1 and 2:1.

8. The method of claim 1, wherein the method further comprises establishing a transmembrane pressure across the filter between about 10-20 psi.

9. The method of claim 1, wherein separating host cell contaminants from the at least one antigen comprises subjecting the at least one antigen to ion-exchange chromatography.

10. The method of claim 1, wherein subjecting the at least one antigen to affinity chromatography comprises subjecting the at least one antigen to cobalt immobilized metal affinity chromatography.

11. The method of claim 1, wherein subjecting the at least one antigen to multi-modal chromatography comprises subjecting the at least one antigen to a ceramic hydroxyapatite chromatography column.

* * * * *